(12) United States Patent
Barnes et al.

(10) Patent No.: US 8,252,820 B2
(45) Date of Patent: *Aug. 28, 2012

(54) 1-ORTHOFLUOROPHENYL SUBSTITUTED 1,2,5-THIAZOLIDINEDIONE DERIVATIVES AS PTP-AS INHIBITORS

(75) Inventors: David Barnes, Waban, MA (US); Gary Mark Coppola, Budd Lake, NJ (US); Travis Stams, Stow, MA (US); Sidney Wolf Topiol, Fair Lawn, NJ (US)

(73) Assignee: Novartis AG, Basel (CH)

( * ) Notice: Subject to any disclaimer, the term of this patent is extended or adjusted under 35 U.S.C. 154(b) by 915 days.

This patent is subject to a terminal disclaimer.

(21) Appl. No.: 12/096,432

(22) PCT Filed: Dec. 6, 2006

(86) PCT No.: PCT/US2006/046542
§ 371 (c)(1),
(2), (4) Date: Oct. 17, 2008

(87) PCT Pub. No.: WO2007/067612
PCT Pub. Date: Jun. 14, 2007

(65) Prior Publication Data
US 2010/0035942 A1  Feb. 11, 2010

Related U.S. Application Data

(60) Provisional application No. 60/748,492, filed on Dec. 8, 2005.

(51) Int. Cl.
*A61K 31/433* (2006.01)
*C07D 285/10* (2006.01)

(52) U.S. Cl. ............................... 514/362; 548/135
(58) Field of Classification Search ............ 514/362; 548/135
See application file for complete search history.

(56) References Cited

U.S. PATENT DOCUMENTS

| | | | |
|---|---|---|---|
| 6,861,431 B2 * | 3/2005 | Gudkov et al. | 514/252.1 |
| 7,291,635 B2 * | 11/2007 | Coppola et al. | 514/362 |
| 7,700,633 B2 * | 4/2010 | Barnes et al. | 514/362 |
| 7,799,782 B2 * | 9/2010 | Munson et al. | 514/234.5 |
| 2008/0262050 A1 | 10/2008 | Barnes et al. | |
| 2008/0293776 A1 | 11/2008 | Barnes et al. | |
| 2008/0293782 A1 | 11/2008 | Barnes et al. | |
| 2009/0181928 A1 | 7/2009 | Neubert et al. | |

FOREIGN PATENT DOCUMENTS

| | | |
|---|---|---|
| WO | 03082841 A | 10/2003 |
| WO | 04041799 A | 5/2004 |
| WO | 2004050646 A | 6/2004 |

OTHER PUBLICATIONS

Biack, et al. "Structure-based design of protein tyrosine phosphatase-I 6 inhibitors." Bioorganic and medicinal chemistry letters, vol. 15, No. 10, Apr. 16, 2006, pp. 2503-2507. p. 2504, Scheme 1.
Elchebly, et at. "Increased Insulin Sensitivity and Obesity Resistance in Mice Lacking the Protein Tyrosine phosphatase-IB Gene" Science, vol. 283, Mar. 5, 1999, pp. 1544-1548.
Johnson, et al. "Protein Tyrosine Phosphatase 1 B Inhibitors for Diabetes" Nature, vol. 1, Sep. 2002, pp. 696-709.
Unpublished U.S. Appl. No. 12/515,519, filed Nov. 30, 2007, in the name of Novartis AG.
Unpublished U.S. Appl. No. 12/602,709, filed Jun. 3, 2008, in the name of Novartis AG.

* cited by examiner

*Primary Examiner* — Rei-tsang Shiao
(74) *Attorney, Agent, or Firm* — Joshua Roth

(57) ABSTRACT

Compounds of the formula

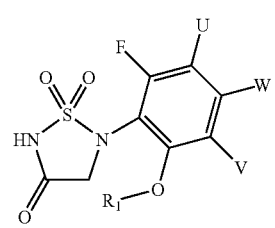

(I)

are inhibitors of protein tyrosine phosphatases (PTPases) and, thus, may be employed for the treatment of conditions mediated by PTPase activity. The compounds of the present invention may also be employed as inhibitors of other enzymes characterized with a phosphotyrosine binding region such as the SH2 domain. Accordingly, the compounds of formula (I) may be employed for prevention and/or treatment of insulin resistance associated with obesity, glucose intolerance, diabetes mellitus, hypertension and ischemic diseases of the large and small blood vessels, conditions that accompany type-2 diabetes, including hyperlipidemia, hypertriglyceridemia, atherosclerosis, vascular restenosis, irritable bowel syndrome, pancreatitis, adipose cell tumors and carcinomas such as liposarcoma, dyslipidemia, and other disorders where insulin resistance is indicated. In addition, the compounds of the present invention may be employed to treat and/or prevent cancer, osteoporosis, neurodegenerative and infectious diseases, and diseases involving inflammation and the immune system.

30 Claims, No Drawings

1-ORTHOFLUOROPHENYL SUBSTITUTED 1,2,5-THIAZOLIDINEDIONE DERIVATIVES AS PTP-AS INHIBITORS

This application is the National Stage of Application No. PCT/US2006/046542, filed on Dec. 6, 2006, which claims benefit under 35 U.S.C. §119(e) of U.S. Provisional Application No. 60/748,492, filed Dec. 8, 2005, the contents of which are incorporated herein by reference in their entirety.

The present invention relates to thiadiazolidinone derivatives, pharmaceutical compositions containing such compounds, methods of making such and methods of treating conditions mediated by protein tyrosine phosphatases by employing such compounds.

Accordingly, the present invention provides compounds of the formula

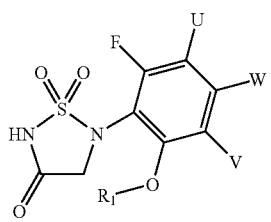

(I)

wherein
  $R_1$ is hydrogen, —C(O)$R_2$, —C(O)N$R_3R_4$ or —C(O)O$R_5$
  in which
    $R_2$ and $R_3$ are, independently from each other, hydrogen, cycloalkyl, aryl, heterocyclyl, aralkyl, heteroaralkyl or alkyl optionally substituted with one to four substituents selected from the group consisting of halogen, cycloalkyl, cycloalkoxy, alkoxy, alkyloxyalkoxy, amino, alkylamino, dialkylamino, aryl, aryloxy and heterocyclyl;
    $R_4$ and $R_5$ are, independently from each other, cycloalkyl, aryl, heterocyclyl, aralkyl, heteroaralkyl or alkyl optionally substituted with one to four substituents selected from the group consisting of halogen, cycloalkyl, cycloalkoxy, alkoxy, alkyloxyalkoxy, amino, alkylamino, dialkylamino, aryl, aryloxy and heterocyclyl;
  U, W and V are, independently from each other, hydrogen, hydroxy, halogen, cyano, nitro, alkoxy, alkylthio, alkylthiono, sulfonyl, free or esterified carboxy, carbamoyl, sulfamoyl, optionally substituted amino, cycloalkyl, aryl, aryloxy, arylthio, heterocyclyl, heterocycloyloxy, alkenyl, alkynyl or ($C_{1-8}$)alkyl optionally substituted with one to four substituents selected from the group consisting of halogen, hydroxy, cycloalkyl, cycloalkoxy, acyl, acyloxy, alkoxy, alkyloxyalkoxy, amino, alkylamino, dialkylamino, acylamino, carbamoyl, thiol, alkylthio, alkylthiono, sulfonyl, sulfonamido, sulfamoyl, nitro, cyano, free or esterified carboxy, aryl, aryloxy, arylthio, alkenyl, alkynyl, aralkoxy, heteroaralkoxy, heterocyclyl and heterocyclyloxy; or
  U and W combined together with the carbon atoms to which they are attached form an optionally substituted aromatic, or a partially or fully saturated nonaromatic 5- to 8-membered carbocyclic or heterocyclic ring; or
  W and V combined together with the carbon atoms to which they are attached form an optionally substituted aromatic, or partially or fully saturated nonaromatic 5- to 8-membered carbocyclic or heterocyclic ring;
or a pharmaceutically acceptable salt thereof.

The compounds of the present invention are inhibitors of protein tyrosine phosphatases (PTPases), in particular, the compounds of formula (I) inhibit PTPase-1B (PTP-1B) and T-cell PTPase (TC PTP) and, thus, may be employed for the treatment of conditions mediated by PTPase activity. Accordingly, the compounds of formula (I) may be employed for treatment of insulin resistance, glucose intolerance, obesity, diabetes mellitus, hypertension and ischemic diseases of the large and small blood vessels, conditions accompanying type 2 diabetes including dyslipidemia, e.g., hyperlipidemia and hypertriglyceridemia, atherosclerosis, vascular restenosis, irritable bowel syndrome, pancreatitis, adipose cell tumors and carcinomas such as liposarcoma, dyslipidemia, and other disorders where insulin resistance is indicated. In addition, the compounds of the present invention may be employed to treat cancer (such as prostate or breast cancer), osteoporosis, neurodegenerative and infectious diseases, and diseases involving inflammation and the immune system.

The present invention also concerns the use of the compounds of formula (I) may be employed for treatment of insulin resistance, glucose intolerance, type 2 diabetes, renal insufficiency (diabetic and non-diabetic), diabetic nephropathy, glomerulonephritis, glomerular sclerosis, proteinuria of primary renal disease, diabetic retinopathy, obesity, all types of heart failures including acute and chronic congestive heart failure, left ventricular dysfunction and hypertrophic cardiomyopathy, diabetic cardiac myopathy, supraventricular and ventricular arrhythmias, atrial fibrillation and atrial flutter, hypertension, primary and secondary pulmonary hypertension, renal vascular hypertension, dyslipidemia, atherosclerosis, ischemic diseases of the large and small blood vessels, angina pectoris (whether unstable or stable), myocardial infarction and its sequelae, ischemia/reperfusion injury, detrimental vascular remodeling including vascular restenosis, management of other vascular disorders including migraine, peripheral vascular disease and Raynaud's disease, irritable bowel syndrome, pancreatitis, cancer (such as prostate or breast cancer), osteoporosis, multiple sclerosis, stroke, spinal cord injury, neurodegenerative diseases such as Alzheimer's, Parkinson's and polyglutamine disorders such as Huntington's and spinocerebellar ataxia, infectious diseases, and diseases involving inflammation and the immune system and diseases involving muscle degeneration.

Listed below are definitions of various terms used to describe the compounds of the instant invention. These definitions apply to the terms as they are used throughout the specification unless they are otherwise limited in specific instances either individually or as part of a larger group. In general, whenever an alkyl group is referred to as a part of the structure, an optionally substituted alkyl is also indended.

Accordingly, the term "optionally substituted alkyl" refers to unsubstituted or substituted straight or branched chain hydrocarbon groups having 1 to 20 carbon atoms, preferably 1 to 8 carbon atoms. Exemplary unsubstituted alkyl groups include methyl, ethyl, propyl, isopropyl, n-butyl, t-butyl, isobutyl, pentyl, hexyl, isohexyl, heptyl, 4,4-dimethylpentyl, octyl and the like. Substituted alkyl groups include, but are not limited to, alkyl groups substituted by one or more of the following groups: halogen, hydroxy, cycloalkyl, cycloalkoxy, acyl, acyloxy, alkoxy, alkyloxyalkoxy, alkanoyloxy, amino, alkylamino, dialkylamino, acylamino, carbamoyl, thiol, alkylthio, alkylthiono, sulfonyl, sulfonamido, sulfamoyl, nitro, cyano, free or esterified carboxy, aryl, aryloxy, arylthio, alkenyl, alkynyl, aralkoxy, heteroaraloxy, heterocyclyl and heterocyclyloxy including indolyl, imidazolyl, furyl, thienyl, thiazolyl, pyrrolidyl, pyridyl, pyrimidyl, piperidyl, morpholinyl and the like.

The term "lower alkyl" refers to any of the above alkyl groups as described above having 1 to 7, preferably 1 to 4 carbon atoms.

The term "halogen" or "halo" refers to fluorine, chlorine, bromine and iodine.

The term "alkenyl" refers to any of the above alkyl groups having at least 2 carbon atoms and containing a carbon to carbon double bond at the point of attachment. Groups having 2 to 8 carbon atoms are preferred.

The term "alkynyl" refers to any of the above alkyl groups having at least two carbon atoms and containing a carbon to carbon triple bond at the point of attachment. Groups having 2 to 8 carbon atoms are preferred.

The term "alkylene" refers to a straight-chain bridge of 1-6 carbon atoms connected by single bonds, e.g., —(CH$_2$)x-, wherein x is 1-6, which may be interrupted with one or more heteroatoms selected from O, S, S(O), S(O)$_2$ or NR", wherein R" may be hydrogen, alkyl, cycloalkyl, aryl, heterocyclyl, aralkyl, heteroaralkyl, acyl, carbamoyl, sulfonyl, alkoxycarbonyl, aryloxycarbonyl or aralkoxycarbonyl and the like; and the alkylene may further be substituted with one or more substituents selected from hydroxy, halogen, cyano, nitro, alkoxy, alkylthio, alkylthiono, sulfonyl, free or esterified carboxy, carbamoyl, sulfamoyl, optionally substituted amino, cycloalkyl, aryl, heterocyclyl, alkenyl, alkynyl or (C$_{1-8}$)alkyl optionally substituted with one to four substituents selected from the group consisting of halogen, hydroxy, cycloalkyl, cycloalkoxy, acyl, acyloxy, alkoxy, alkyloxyalkoxy, amino, alkylamino, dialkylamino, acylamino, carbamoyl, thiol, alkylthio, alkylthiono, sulfonyl, sulfonamido, sulfamoyl, nitro, cyano, free or esterified carboxy, aryl, aryloxy, arylthio, alkenyl, alkynyl, aralkoxy, heteroaralkoxy, heterocyclyl, heterocyclyloxy and the like.

The term "cycloalkyl" refers to optionally substituted monocyclic, bicyclic or tricyclic hydrocarbon groups of 3 to 12 carbon atoms, each of which may be substituted by one or more substituents such as alkyl, halo, oxo, hydroxy, alkoxy, alkanoyl, acylamino, carbamoyl, alkylamino, dialkylamino, thiol, alkylthio, nitro, cyano, carboxy, carboxyalkyl, alkoxycarbonyl, sulfonyl, sulfonamido, sulfamoyl, heterocyclyl and the like.

Exemplary monocyclic hydrocarbon groups include but are not limited to cyclopropyl, cyclobutyl, cyclopentyl, cyclopentenyl, cyclohexyl and cyclohexenyl and the like.

Exemplary bicyclic hydrocarbon groups include bornyl, indyl, hexahydroindyl, tetrahydronaphthyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, bicyclo[2.2.2]octyl and the like.

Exemplary tricyclic hydrocarbon groups include adamantyl and the like.

The term "alkoxy" refers to alkyl-O—.
The term "alkanoyl" refers to alkyl-C(O)—.
The term "alkanoyloxy" refers to alkyl-C(O)—O—.
The terms "alkylamino" and "dialkylamino" refer to alkyl-NH— and (alkyl)$_2$N—, respectively.
The term "alkanoylamino" refers to alkyl-C(O)—NH—.
The term "alkylthio" refers to alkyl-S—.
The term "alkylaminothiocarbonyl" refers to alkyl-NHC(S)—.
The term "trialkylsilyl" refers to (alkyl)$_3$Si—.
The term "trialkylsilyloxy" refers to (alkyl)$_3$SiO—.
The term "alkylthiono" refers to alkyl-S(O)—.
The term "alkylsulfonyl" refers to alkyl-S(O)$_2$—.

The term "alkoxycarbonyl" refers to alkyl-O—C(O)—.
The term "alkoxycarbonyloxy" refers to alkyl-O—C(O)O—.
The term "carboxycarbonyl" refers to HO—C(O)C(O)—.
The term "carbamoyl" refers to H$_2$NC(O)—, alkyl-NHC(O)—, (alkyl)$_2$NC(O)—, aryl-NHC(O)—, alkyl(aryl)-NC(O)—, heteroaryl-NHC(O)—, alkyl(heteroaryl)-NC(O)—, aralkyl-NHC(O)—, alkyl(aralkyl)-NC(O)— and the like.

The term "sulfamoyl" refers to H$_2$NS(O)$_2$—, alkyl-NHS(O)$_2$—, (alkyl)$_2$NS(O)$_2$—, aryl-NHS(O)$_2$—, alkyl(aryl)-NS(O)$_2$—, (aryl)$_2$NS(O)$_2$—, heteroaryl-NHS(O)$_2$—, aralkyl-NHS(O)$_2$—, heteroaralkyl-NHS(O)$_2$— and the like.

The term "sulfonamido" refers to alkyl-S(O)$_2$—NH—, aryl-S(O)$_2$—NH—, aralkyl-S(O)$_2$—NH—, heteroaryl-S(O)$_2$—NH—, heteroaralkyl-S(O)$_2$—NH—, alkyl-S(O)$_2$—N(alkyl)-, aryl-S(O)$_2$—N(alkyl)-, aralkyl-S(O)$_2$—N(alkyl)-, heteroaryl-S(O)$_2$—N(alkyl)-, heteroaralkyl-S(O)$_2$—N(alkyl)- and the like.

The term "sulfonyl" refers to alkylsulfonyl, arylsulfonyl, heteroarylsulfonyl, aralkylsulfonyl, heteroaralkylsulfonyl and the like.

The term "sulfonate" or "sulfonyloxy" refers to alkyl-S(O)$_2$—O—, aryl-S(O)$_2$—O—, aralkyl-S(O)$_2$—O—, heteroaryl-S(O)$_2$—O—, heteroaralkyl-S(O)$_2$—O— and the like.

The term "optionally substituted amino" refers to a primary or secondary amino group which may optionally be substituted by a substituent such as acyl, sulfonyl, alkoxycarbonyl, cycloalkoxycarbonyl, aryloxycarbonyl, heteroaryloxycarbonyl, aralkoxycarbonyl, heteroaralkoxycarbonyl, carboxycarbonyl, carbamoyl, alkylaminothiocarbonyl, arylaminothiocarbonyl and the like.

The term "aryl" refers to monocyclic or bicyclic aromatic hydrocarbon groups having 6 to 12 carbon atoms in the ring portion, such as phenyl, naphthyl, tetrahydronaphthyl, biphenyl and diphenyl groups, each of which may optionally be substituted by one to five substituents such as hydroxy, halogen, cyano, nitro, alkoxy, alkylthio, alkylthiono, sulfonyl, sulfonate, free or esterified carboxy, carbamoyl, sulfamoyl, optionally substituted amino, cycloalkyl, aryl, heterocyclyl, alkenyl, alkynyl or (C$_{1-8}$)alkyl optionally substituted with one to four substituents selected from the group consisting of halogen, hydroxy, cycloalkyl, cycloalkoxy, acyl, acyloxy, alkoxy, alkyloxyalkoxy, amino, alkylamino, dialkylamino, acylamino, carbamoyl, thiol, alkylthio, alkylthiono, sulfonyl, sulfonamido, sulfamoyl, nitro, cyano, free or esterified carboxy, aryl, aryloxy, arylthio, alkenyl, alkynyl, aralkoxy, heteroaralkoxy, heterocyclyl, heterocyclyloxy and the like.

The term "monocyclic aryl" refers to optionally substituted phenyl as described under aryl.

The term "aralkyl" refers to an aryl group bonded directly through an alkyl group, such as benzyl.

The term "aralkanoyl" refers to aralkyl-C(O)—.
The term "aralkylthio" refers to aralkyl-S—.
The term "aralkoxy" refers to an aryl group bonded directly through an alkoxy group.
The term "arylsulfonyl" refers to aryl-S(O)$_2$—.
The term "arylthio" refers to aryl-S—.
The term "aroyl" refers to aryl-C(O)—.
The term "aroylamino" refers to aryl-C(O)—NH—.
The term "aryloxycarbonyl" refers to aryl-O—C(O)—.

The term "heterocyclyl" or "heterocyclo" refers to an optionally substituted, aromatic, or a partially or fully saturated nonaromatic cyclic group, for example, which is a 4- to 7-membered monocyclic, 7- to 12-membered bicyclic, or 10- to 15-membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized. The heterocyclic group may be attached at a heteroatom or a carbon atom.

Exemplary monocyclic heterocyclic groups include pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, 1,1,4-trioxo-1,2,5-thiadiazolidin-2-yl and the like.

Exemplary bicyclic heterocyclic groups include indolyl, dihydroidolyl, benzothiazolyl, benzoxazinyl, benzoxazolyl, benzothienyl, benzothiazinyl, quinuclidinyl, quinolinyl, tetrahydroquinolinyl, decahydroquinolinyl, isoquinolinyl, tetrahydroisoquinolinyl, decahydroisoquinolinyl, benzimidazolyl, benzopyranyl, indolizinyl, benzofuryl, chromonyl, coumarinyl, benzopyranyl, benzodiazepinyl, cinnolinyl, quinoxalinyl, indazolyl, pyrrolopyridyl, furopyridinyl (such as furo[2,3-c]pyridinyl, furo[3,2-b]-pyridinyl] or furo[2,3-b]pyridinyl), dihydroisoindolyl, 1,3-dioxo-1,3-dihydroisoindol-2-yl, dihydroquinazolinyl (such as 3,4-dihydro-4-oxo-quinazolinyl), phthalazinyl and the like.

Exemplary tricyclic heterocyclic groups include carbazolyl, dibenzoazepinyl, dithienoazepinyl, benzindolyl, phenanthrolinyl, acridinyl, phenanthridinyl, phenoxazinyl, phenothiazinyl, xanthenyl, carbolinyl and the like.

The term "heterocyclyl" includes substituted heterocyclic groups. Substituted heterocyclic groups refer to heterocyclic groups that are substituted with 1, 2 or 3 substituents selected from the group consisting of the following:

(a) optionally substituted alkyl;
(b) hydroxy (or protected hydroxy);
(c) halo;
(d) oxo (i.e. =O);
(e) optionally substituted amino, alkylamino or dialkylamino;
(f) alkoxy;
(g) cycloalkyl;
(h) carboxy;
(i) heterocyclooxy;
(j) alkoxycarbonyl, such as unsubstituted lower alkoxycarbonyl;
(k) mercapto;
(l) nitro;
(m) cyano;
(n) sulfamoyl or sulfonamido;
(o) alkylcarbonyloxy;
(p) arylcarbonyloxy;
(q) arylthio;
(r) aryloxy;
(s) alkylthio;
(t) formyl;
(u) carbamoyl;
(v) aralkyl; and
(w) aryl substituted with alkyl, cycloalkyl, alkoxy, hydroxy, amino, acylamino, alkylamino, dialkylamino or halo.

The term "heterocyclooxy" denotes a heterocyclic group bonded through an oxygen bridge.

The term "heteroaryl" refers to an aromatic heterocycle, for example monocyclic or bicyclic aryl, such as pyrrolyl, pyrazolyl, imidazolyl, oxazolyl, isoxazolyl, thiazolyl, isothiazolyl, furyl, thienyl, pyridyl, pyrazinyl, pyrimidinyl, pyridazinyl, indolyl, benzothiazolyl, benzoxazolyl, benzothienyl, quinolinyl, isoquinolinyl, benzimidazolyl, benzofuryl, and the like, optionally substituted by e.g. lower alkyl, lower alkoxy or halo.

The term "heteroarylsulfonyl" refers to heteroaryl-$S(O)_2$—.

The term "heteroaroyl" refers to heteroaryl-C(O)—.

The term "heteroaroylamino" refers to heteroaryl-C(O)NH—

The term "heteroaralkyl" refers to a heteroaryl group bonded through an alkyl group.

The term "heteroaralkanoyl" refers to heteroaralkyl-C(O)—.

The term "heteroaralkanoylamino" refers to heteroaralkyl-C(O)NH—.

The term "acyl" refers to alkanoyl, cycloalkanoyl, aroyl, heteroaroyl, aralkanoyl, heteroaralkanoyl and the like.

The term "acyloxy" refers to alkanoyloxy, cycloalkanoyloxy, aroyloxy, heteroaroyloxy, aralkanoyloxy, heteroaralkanoyloxy and the like.

The term "acylamino" refers to alkanoylamino, cycloalkanoylamino, aroylamino, heteroaroylamino, aralkanoylamino, heteroaralkanoylamino and the like.

The term "esterified carboxy" refers to optionally substituted alkoxycarbonyl, cycloalkoxycarbonyl, aryloxycarbonyl, aralkoxycarbonyl, heterocyclooxycarbonyl and the like.

Pharmaceutically acceptable salts of any compound of the present invention refer to salts formed with bases, namely cationic salts such as alkali and alkaline earth metal salts, such as sodium, lithium, potassium, calcium, magnesium, as well as ammonium salts, such as ammonium, trimethylammonium, diethylammonium, and tris(hydroxymethyl)-methyl-ammonium salts, and salts with amino acids.

Similarly acid addition salts, such as those formed with mineral acids, organic carboxylic acids and organic sulfonic acids e.g. hydrochloric acid, maleic acid and methanesulfonic acid, are possible provided a basic group, such as pyridyl, constitutes part of the structure.

As described herein above, the present invention provides 1,1-dioxo-1,2,5-thiadiazolidin-3-one derivatives of formula (I), pharmaceutical compositions containing the same, methods for preparing such compounds and methods of treating and/or preventing conditions associated with PTPase activity, in particular, PTP-1B and TC PTP activity, by administration of a therapeutically effective amount of a compound of the present invention, or a pharmaceutical composition thereof.

Preferred are the compounds of formula (I) wherein
U and W combined together with the carbon atoms to which they are attached form an optionally substituted aromatic, or a partially or fully saturated nonaromatic 5- to 8-membered carbocyclic or heterocyclic ring;
V is hydrogen;
or a pharmaceutically acceptable salt thereof.

Further preferred are the compounds of formula (I) having the formula

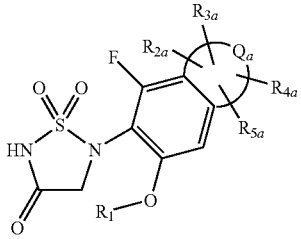

(Ia)

wherein
- $Q_a$ combined together with the carbon atoms to which it is attached form an aromatic, or a partially or fully saturated nonaromatic 5- to 8-membered carbocyclic or heterocyclic ring;
- $R_1$ is hydrogen, —C(O)R$_2$, —C(O)NR$_3$R$_4$ or —C(O)OR$_5$ in which
  - $R_2$ and $R_3$ are, independently from each other, hydrogen, cycloalkyl, aryl, heterocyclyl, aralkyl, heteroaralkyl or alkyl optionally substituted with one to four substituents selected from the group consisting of halogen, cycloalkyl, cycloalkoxy, alkoxy, alkyloxyalkoxy, amino, alkylamino, dialkylamino, aryl, aryloxy and heterocyclyl;
  - $R_4$ and $R_5$ are, independently from each other, cycloalkyl, aryl, heterocyclyl, aralkyl, heteroaralkyl or alkyl optionally substituted with one to four substituents selected from the group consisting of halogen, cycloalkyl, cycloalkoxy, alkoxy, alkyloxyalkoxy, amino, alkylamino, dialkylamino, aryl, aryloxy and heterocyclyl;
- $R_{2a}$, $R_{3a}$, $R_{4a}$ and $R_{5a}$ are, independently from each other, hydrogen, hydroxy, halogen, cyano, nitro, alkoxy, alkylthio, alkylthiono, sulfonyl, free or esterified carboxy, carbamoyl, sulfamoyl, optionally substituted amino, cycloalkyl, aryl, heterocyclyl, alkenyl, alkynyl or (C$_{1-8}$) alkyl optionally substituted with one to four substituents selected from the group consisting of halogen, hydroxy, cycloalkyl, cycloalkoxy, acyl, acyloxy, alkoxy, alkyloxyalkoxy, amino, alkylamino, dialkylamino, acylamino, carbamoyl, thiol, alkylthio, alkylthiono, sulfonyl, sulfonamido, sulfamoyl, nitro, cyano, free or esterified carboxy, aryl, aryloxy, arylthio, alkenyl, alkynyl, aralkoxy, heteroaralkoxy, heterocyclyl and heterocyclyloxy; or
- $R_{2a}$ and $R_{3a}$ combined are alkylene which together with the ring atoms to which they are attached form a 3- to 7-membered fused ring; or
- $R_{2a}$ and $R_{3a}$ combined are alkylene which together with the carbon atom to which they are attached form a 3- to 7-membered spirocyclic ring;

or a pharmaceutically acceptable salt thereof.

Preferred are compounds of formula (Ia), designated as the A group, wherein
- $Q_a$ combined together with the carbon atoms to which it is attached form an aromatic, or a partially or fully saturated 5- to 6-membered carbocyclic ring;

or a pharmaceutically acceptable salt thereof.

Preferred are compounds in the A group having the formula

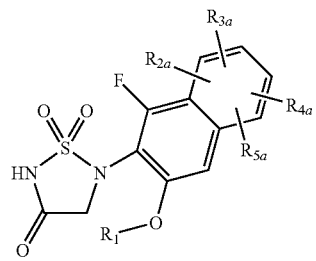

(Ia$_1$)

wherein
- $R_1$ is hydrogen, —C(O)R$_2$, —C(O)NR$_3$R$_4$ or —C(O)OR$_5$ in which
  - $R_2$ and $R_3$ are, independently from each other, hydrogen, cycloalkyl, aryl, heterocyclyl, aralkyl, heteroaralkyl or alkyl optionally substituted with one to four substituents selected from the group consisting of halogen, cycloalkyl, cycloalkoxy, alkoxy, alkyloxyalkoxy, amino, alkylamino, dialkylamino, aryl, aryloxy and heterocyclyl;
  - $R_4$ and $R_5$ are, independently from each other, cycloalkyl, aryl, heterocyclyl, aralkyl, heteroaralkyl or alkyl optionally substituted with one to four substituents selected from the group consisting of halogen, cycloalkyl, cycloalkoxy, alkoxy, alkyloxyalkoxy, amino, alkylamino, dialkylamino, aryl, aryloxy and heterocyclyl;
- $R_{2a}$, $R_{3a}$, $R_{4a}$ and $R_{5a}$ are, independently from each other, hydrogen, hydroxy, halogen, cyano, nitro, alkoxy, alkylthio, alkylthiono, sulfonyl, free or esterified carboxy, carbamoyl, sulfamoyl, optionally substituted amino, cycloalkyl, aryl, heterocyclyl, alkenyl, alkynyl or (C$_{1-8}$) alkyl optionally substituted with one to four substituents selected from the group consisting of halogen, hydroxy, cycloalkyl, cycloalkoxy, acyl, acyloxy, alkoxy, alkyloxyalkoxy, amino, alkylamino, dialkylamino, acylamino, carbamoyl, thiol, alkylthio, alkylthiono, sulfonyl, sulfonamido, sulfamoyl, nitro, cyano, free or esterified carboxy, aryl, aryloxy, arylthio, alkenyl, alkynyl, aralkoxy, heteroaralkoxy, heterocyclyl and heterocyclyloxy; or
- $R_{2a}$ and $R_{3a}$ combined are alkylene which together with the ring atoms to which they are attached form a 5- to 7-membered fused ring; or or a pharmaceutically acceptable salt thereof.

Preferred are compounds of formula (Ia$_1$) wherein
$R_{4a}$ and $R_{5a}$ are hydrogen;
or a pharmaceutically acceptable salt thereof.

Further preferred are compounds of formula (Ia$_1$) having the formula

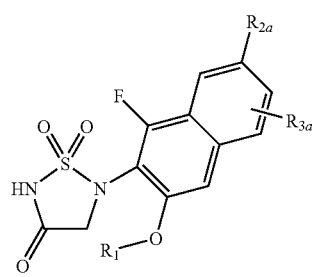

(Ia$_2$)

wherein
R₁ is hydrogen, —C(O)R₂, —C(O)NR₃R₄ or —C(O)OR₅ in which
R₂ and R₃ are, independently from each other, hydrogen, cycloalkyl, aryl, heterocyclyl, aralkyl, heteroaralkyl or alkyl optionally substituted with one to four substituents selected from the group consisting of halogen, cycloalkyl, cycloalkoxy, alkoxy, alkyloxyalkoxy, amino, alkylamino, dialkylamino, aryl, aryloxy and heterocyclyl;
R₄ and R₅ are, independently from each other, cycloalkyl, aryl, heterocyclyl, aralkyl, heteroaralkyl or alkyl optionally substituted with one to four substituents selected from the group consisting of halogen, cycloalkyl, cycloalkoxy, alkoxy, alkyloxyalkoxy, amino, alkylamino, dialkylamino, aryl, aryloxy and heterocyclyl;
R$_{2a}$ and R$_{3a}$ are, independently from each other, hydrogen, hydroxy, halogen, cyano, nitro, alkoxy, alkylthio, alkylthiono, sulfonyl, free or esterified carboxy, carbamoyl, sulfamoyl, optionally substituted amino, cycloalkyl, aryl, heterocyclyl, alkenyl, alkynyl or (C$_{1-8}$)alkyl optionally substituted with one to four substituents selected from the group consisting of halogen, hydroxy, cycloalkyl, cycloalkoxy, acyl, acyloxy, alkoxy, alkyloxyalkoxy, amino, alkylamino, dialkylamino, acylamino, carbamoyl, thiol, alkylthio, alkylthiono, sulfonyl, sulfonamido, sulfamoyl, nitro, cyano, free or esterified carboxy, aryl, aryloxy, arylthio, alkenyl, alkynyl, aralkoxy, heteroaralkoxy, heterocyclyl and heterocyclyloxy;

or a pharmaceutically acceptable salt thereof.

Preferred are compounds of formula (Ia₂) wherein
R$_{2a}$ is —Y$_a$—(CH₂)$_n$—CR$_{6a}$R$_{7a}$—(CH₂)$_m$—X$_a$ in which
Y$_a$ is oxygen or S(O)$_q$ in which q is zero or an integer of 1 or 2; or
Y$_a$ is trans CH=CH; or
Y$_a$ is absent;
n is an integer from 1 to 6;
R$_{6a}$ and R$_{7a}$ are, independently from each other, hydrogen or lower alkyl; or
R$_{6a}$ and R$_{7a}$ combined are alkylene which together with the carbon atom to which they are attached form a 3- to 7-membered ring;
m is zero or an integer of 1 or 2;
X$_a$ is hydroxy, alkoxy, cycloalkyl, cycloalkoxy, acyl, acyloxy, carbamoyl, cyano, trifluoromethyl, free or esterified carboxy, monocyclic aryl or heterocyclyl;

or a pharmaceutically acceptable salt thereof.

Further preferred are compounds of formula (Ia₂) wherein
R$_{3a}$ is hydrogen;

or a pharmaceutically acceptable salt thereof.

Further preferred are also compounds of formula (Ia₂) wherein
n is an integer of 2 or 3;
R$_{6a}$ and R$_{7a}$ are, independently from each other, hydrogen or lower alkyl;
m is zero or 1;
X$_a$ is hydroxy, carbamoyl, cyano, trifluoromethyl, free or esterified carboxy, monocyclic aryl or heterocyclyl;

or a pharmaceutically acceptable salt thereof.

More preferred are compounds of formula (Ia₂) wherein
Y$_a$ is absent;

or a pharmaceutically acceptable salt thereof.

Even more preferred are compounds of formula (Ia₂) wherein
n is 3;
R$_{6a}$ and R$_{7a}$ are lower alkyl;
m is zero or 1;
X$_a$ is hydroxy, cyano or free or esterified carboxy;

or a pharmaceutically acceptable salt thereof.

Most preferred are compounds of formula (Ia₂) wherein
R$_{6a}$ and R$_{7a}$ are methyl;

or a pharmaceutically acceptable salt thereof.

Especially preferred are compounds of formula (Ia₂) wherein
R₁ is hydrogen or —C(O)R₂ in which R₂ is monocyclic aryl;

or a pharmaceutically acceptable salt thereof.

Preferred are also compounds in the A group having the formula

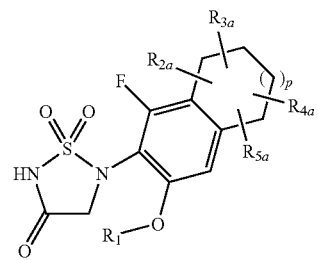

(Ia₃)

wherein
R₁ is hydrogen, —C(O)R₂, —C(O)NR₃R₄ or —C(O)OR₅ in which
R₂ and R₃ are, independently from each other, hydrogen, cycloalkyl, aryl, heterocyclyl, aralkyl, heteroaralkyl or alkyl optionally substituted with one to four substituents selected from the group consisting of halogen, cycloalkyl, cycloalkoxy, alkoxy, alkyloxyalkoxy, amino, alkylamino, dialkylamino, aryl, aryloxy and heterocyclyl;
R₄ and R₅ are, independently from each other, cycloalkyl, aryl, heterocyclyl, aralkyl, heteroaralkyl or alkyl optionally substituted with one to four substituents selected from the group consisting of halogen, cycloalkyl, cycloalkoxy, alkoxy, alkyloxyalkoxy, amino, alkylamino, dialkylamino, aryl, aryloxy and heterocyclyl;
R$_{2a}$, R$_{3a}$, R$_{4a}$ and R$_{5a}$ are, independently from each other, hydrogen, hydroxy, halogen, cyano, nitro, alkoxy, alkylthio, alkylthiono, sulfonyl, free or esterified carboxy, carbamoyl, sulfamoyl, optionally substituted amino, cycloalkyl, aryl, heterocyclyl, alkenyl, alkynyl or (C$_{1-8}$) alkyl optionally substituted with one to four substituents selected from the group consisting of halogen, hydroxy, cycloalkyl, cycloalkoxy, acyl, acyloxy, alkoxy, alkyloxyalkoxy, amino, alkylamino, dialkylamino, acylamino, carbamoyl, thiol, alkylthio, alkylthiono, sulfonyl, sulfonamido, sulfamoyl, nitro, cyano, free or esterified carboxy, aryl, aryloxy, arylthio, alkenyl, alkynyl, aralkoxy, heteroaralkoxy, heterocyclyl and heterocyclyloxy; or
R$_{2a}$ and R$_{3a}$ combined are alkylene which together with the ring atoms to which they are attached form a 3- to 7-membered fused ring; or $R_{2a}$ and $R_{3a}$ combined are alkylene which together with the carbon atom to which they are attached form a 3- to 7-membered spirocyclic ring;

p is zero or 1;

or a pharmaceutically acceptable salt thereof.

Preferred are compounds of formula (Ia$_3$) wherein $R_{4a}$ and $R_{5a}$ are hydrogen;

or a pharmaceutically acceptable salt thereof.

Preferred are also compounds of formula (Ia$_3$) wherein $R_{2a}$ and $R_{3a}$ are, independently from each other, hydrogen, halogen or $(C_{1-4})$alkyl optionally substituted by at least one halogen;

or a pharmaceutically acceptable salt thereof.

Preferred are also compounds of formula (Ia$_3$) wherein p is 1;

or a pharmaceutically acceptable salt thereof.

Further preferred are compounds of formula (Ia$_3$) having the formula

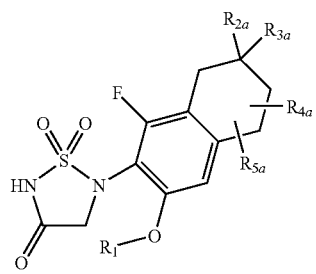

(Ia$_4$)

wherein $R_1$ is hydrogen, —C(O)R$_2$, —C(O)NR$_3$R$_4$ or —C(O)OR$_5$ in which $R_2$ and $R_3$ are, independently from each other, hydrogen, cycloalkyl, aryl, heterocyclyl, aralkyl, heteroaralkyl or alkyl optionally substituted with one to four substituents selected from the group consisting of halogen, cycloalkyl, cycloalkoxy, alkoxy, alkyloxyalkoxy, amino, alkylamino, dialkylamino, aryl, aryloxy and heterocyclyl;

$R_4$ and $R_5$ are, independently from each other, cycloalkyl, aryl, heterocyclyl, aralkyl, heteroaralkyl or alkyl optionally substituted with one to four substituents selected from the group consisting of halogen, cycloalkyl, cycloalkoxy, alkoxy, alkyloxyalkoxy, amino, alkylamino, dialkylamino, aryl, aryloxy and heterocyclyl;

$R_{2a}$, $R_{3a}$, $R_{4a}$ and $R_{5a}$ are, independently from each other, hydrogen, hydroxy, halogen, cyano, nitro, alkoxy, alkylthio, alkylthiono, sulfonyl, free or esterified carboxy, carbamoyl, sulfamoyl, optionally substituted amino, cycloalkyl, aryl, heterocyclyl, alkenyl, alkynyl or $(C_{1-8})$ alkyl optionally substituted with one to four substituents selected from the group consisting of halogen, hydroxy, cycloalkyl, cycloalkoxy, acyl, acyloxy, alkoxy, alkyloxyalkoxy, amino, alkylamino, dialkylamino, acylamino, carbamoyl, thiol, alkylthio, alkylthiono, sulfonyl, sulfonamido, sulfamoyl, nitro, cyano, free or esterified carboxy, aryl, aryloxy, arylthio, alkenyl, alkynyl, aralkoxy, heteroaralkoxy, heterocyclyl and heterocyclyloxy; or $R_{2a}$ and $R_{3a}$ combined are alkylene which together with the carbon atom to which they are attached form a 3- to 7-membered spirocyclic ring;

or a pharmaceutically acceptable salt thereof.

Preferred are compounds of formula (Ia$_4$) wherein $R_{4a}$ and $R_{5a}$ are hydrogen;

or a pharmaceutically acceptable salt thereof.

Preferred are also compounds of formula (Ia$_4$), designated as the B group, wherein $R_{2a}$ and $R_{3a}$ are, independently from each other, hydrogen, halogen or $(C_{1-4})$alkyl optionally substituted by at least one halogen;

or a pharmaceutically acceptable salt thereof.

Preferred are compounds in the B group wherein $R_1$ is hydrogen or —C(O)R$_2$ in which R$_2$ is monocyclic aryl;

or a pharmaceutically acceptable salt thereof.

Preferred are also compounds of formula (Ia$_4$), designated as the C group, wherein $R_{2a}$ and $R_{3a}$ combined are alkylene which together with the carbon atom to which they are attached form a 3- to 5-membered spirocyclic ring;

or a pharmaceutically acceptable salt thereof.

Preferred are compounds in the C group, wherein $R_1$ is hydrogen or —C(O)R$_2$ in which R$_2$ is monocyclic aryl;

or a pharmaceutically acceptable salt thereof.

Preferred are also compounds of formula (Ia$_4$), designated as the D group, wherein $R_{2a}$ is —$Y_a$—(CH$_2$)$_n$—CR$_{6a}$R$_{7a}$—(CH$_2$)$_m$—$X_a$ in which $Y_a$ is oxygen or S(O)$_q$ in which q is zero or an integer of 1 or 2; or $Y_a$ is trans CH=CH; or $Y_a$ is absent;

n is an integer from 1 to 6;

$R_{6a}$ and $R_{7a}$ are, independently from each other, hydrogen or lower alkyl; or $R_{6a}$ and $R_{7a}$ combined are alkylene which together with the carbon atom to which they are attached form a 3- to 7-membered ring;

m is zero or an integer of 1 or 2;

$X_a$ is hydroxy, alkoxy, cycloalkyl, cycloalkoxy, acyl, acyloxy, carbamoyl, cyano, trifluoromethyl, free or esterified carboxy, monocyclic aryl or heterocyclyl;

or a pharmaceutically acceptable salt thereof.

Preferred are compounds in the D group wherein $R_{3a}$ is hydrogen;

or a pharmaceutically acceptable salt thereof.

Further preferred are compounds in the D group wherein n is an integer of 2 or 3;

$R_{6a}$ and $R_{7a}$ are, independently from each other, hydrogen or lower alkyl;

m is zero or 1;

$X_a$ is hydroxy, carbamoyl, cyano, trifluoromethyl, free or esterified carboxy, monocyclic aryl or heterocyclyl;

or a pharmaceutically acceptable salt thereof.

More preferred are compounds in the D group wherein $Y_a$ is absent;

or a pharmaceutically acceptable salt thereof.

Even more preferred are compounds in the D group wherein n is 3;

$R_{6a}$ and $R_{7a}$ are lower alkyl;

m is zero or 1;

$X_a$ is hydroxy, cyano or free or esterified carboxy;
or a pharmaceutically acceptable salt thereof.

Most preferred are compounds in the D group wherein $R_{6a}$ and $R_{7a}$ are methyl;
or a pharmaceutically acceptable salt thereof.

Especially preferred are compounds in the D group wherein
$R_1$ is hydrogen or —C(O)$R_2$ in which $R_2$ is monocyclic aryl;
or a pharmaceutically acceptable salt thereof.

Preferred are also the compounds of formula (I), wherein
U and V are hydrogen;
W is aryloxy, arylthio or methyl substituted with monocyclic aryl;
or a pharmaceutically acceptable salt thereof.

Further preferred are also the compounds of formula (I) having the formula

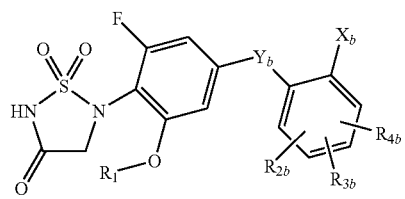

(Ib)

wherein
$R_1$ is hydrogen, —C(O)$R_2$, —C(O)NR$_3$R$_4$ or —C(O)OR$_5$ in which
$R_2$ and $R_3$ are, independently from each other, hydrogen, cycloalkyl, aryl, heterocyclyl, aralkyl, heteroaralkyl or alkyl optionally substituted with one to four substituents selected from the group consisting of halogen, cycloalkyl, cycloalkoxy, alkoxy, alkyloxyalkoxy, amino, alkylamino, dialkylamino, aryl, aryloxy and heterocyclyl;
$R_4$ and $R_5$ are, independently from each other, cycloalkyl, aryl, heterocyclyl, aralkyl, heteroaralkyl or alkyl optionally substituted with one to four substituents selected from the group consisting of halogen, cycloalkyl, cycloalkoxy, alkoxy, alkyloxyalkoxy, amino, alkylamino, dialkylamino, aryl, aryloxy and heterocyclyl;
$R_{2b}$, $R_{3b}$ and $R_{4b}$ are, independently from each other, hydrogen, hydroxy, halogen, cyano, nitro, alkoxy, alkylthio, alkylthiono, sulfonyl, free or esterified carboxy, carbamoyl, sulfamoyl, optionally substituted amino, cycloalkyl, aryl, heterocyclyl, alkenyl, alkynyl or (C$_{1-8}$) alkyl optionally substituted with one to four substituents selected from the group consisting of halogen, hydroxy, cycloalkyl, cycloalkoxy, acyl, acyloxy, alkoxy, alkyloxyalkoxy, amino, alkylamino, dialkylamino, acylamino, carbamoyl, thiol, alkylthio, alkylthiono, sulfonyl, sulfonamido, sulfamoyl, nitro, cyano, free or esterified carboxy, aryl, aryloxy, arylthio, alkenyl, alkynyl, aralkoxy, heteroaralkoxy, heterocyclyl and heterocyclyloxy; or
$R_{2b}$ and $R_{3b}$ combined are alkylene which together with the ring atoms to which they are attached form a 5- to 7-membered fused ring provided $R_2$ and $R_3$ are attached to carbon atoms adjacent to each other; or
$R_{2b}$ and $R_{3b}$ combined together with the carbon atom to which they are attached form a fused 5- to 6-membered aromatic or heteroaromatic ring provided $R_2$ and $R_3$ are attached to carbon atoms adjacent to each other;
$X_b$ is hydrogen, fluoro, cyano, or free or esterified carboxy; or
$X_b$ is —NR$_{5b}$C(O)R$_{6b}$, —NR$_{5b}$C(O)OR$_{7b}$, —NR$_{5b}$S(O)$_2$R$_{8b}$, —(CH$_2$)$_r$S(O)$_2$R$_{9b}$, —OS(O)$_2$R$_{10b}$ or —O$_s$C(O)NR$_{11b}$R$_{12b}$, in which
$R_{5b}$ is hydrogen, lower alkyl, acyl, alkoxycarbonyl or sulfonyl;
$R_{6b}$, $R_{7b}$, $R_{8b}$, $R_{9b}$ and $R_{10b}$ are, independently from each other, cycloalkyl, aryl, heterocyclyl, aralkyl, heteroaralkyl or (C$_{1-8}$)alkyl optionally substituted with one to four substituents selected from the group consisting of halogen, hydroxy, cycloalkyl, cycloalkoxy, acyl, acyloxy, alkoxy, alkyloxyalkoxy, amino, alkylamino, dialkylamino, acylamino, carbamoyl, thiol, alkylthio, alkylthiono, sulfonyl, sulfonamido, sulfamoyl, nitro, cyano, free or esterified carboxy, aryl, aryloxy, arylthio, alkenyl, alkynyl, aralkoxy, heteroaralkoxy, heterocyclyl and heterocyclyloxy; or
$R_{6b}$, $R_{8b}$ and $R_{9b}$ are, independently from each other, —NR$_{13b}$R$_{14b}$ in which
$R_{13b}$ and $R_{14b}$ are, independently from each other, hydrogen, alkyl, cycloalkyl, aralkyl, aryl or heterocyclyl; or
$R_{13b}$ and $R_{14b}$ combined are alkylene which together with the nitrogen atom to which they are attached form a 4- to 7-membered ring;
$R_{11b}$ and $R_{12b}$ are, independently from each other, hydrogen, alkyl, cycloalkyl, aralkyl, aryl or heterocyclyl; or
$R_{11b}$ and $R_{12b}$ combined are alkylene which together with the nitrogen atom to which they are attached form a 4- to 7-membered ring;
r and s are, independently from each other, zero or an integer of 1; or
C—$X_b$ is replaced by nitrogen;
$Y_b$ is O, S or CH$_2$;
or a pharmaceutically acceptable salt thereof.

Preferred are the compounds of formula (Ib) wherein
$Y_b$ is CH$_2$;
or a pharmaceutically acceptable salt thereof.

Further preferred are the compounds of formula (Ib) having the formula

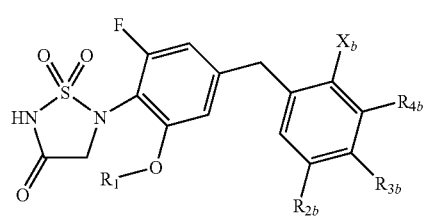

(Ib$_1$)

wherein
$R_1$ is hydrogen, —C(O)$R_2$, —C(O)NR$_3$R$_4$ or —C(O)OR$_5$ in which
$R_2$ and $R_3$ are, independently from each other, hydrogen, cycloalkyl, aryl, heterocyclyl, aralkyl, heteroaralkyl or alkyl optionally substituted with one to four substituents selected from the group consisting of halogen, cycloalkyl, cycloalkoxy, alkoxy, alkyloxyalkoxy, amino, alkylamino, dialkylamino, aryl, aryloxy and heterocyclyl;

R$_4$ and R$_5$ are, independently from each other, cycloalkyl, aryl, heterocyclyl, aralkyl, heteroaralkyl or alkyl optionally substituted with one to four substituents selected from the group consisting of halogen, cycloalkyl, cycloalkoxy, alkoxy, alkyloxyalkoxy, amino, alkylamino, dialkylamino, aryl, aryloxy and heterocyclyl;

R$_{2b}$, R$_{3b}$ and R$_{4b}$ are, independently from each other, hydrogen, hydroxy, halogen, cyano, nitro, alkoxy, alkylthio, alkylthiono, sulfonyl, free or esterified carboxy, carbamoyl, sulfamoyl, optionally substituted amino, cycloalkyl, aryl, heterocyclyl, alkenyl, alkynyl or (C$_{1-8}$)alkyl optionally substituted with one to four substituents selected from the group consisting of halogen, hydroxy, cycloalkyl, cycloalkoxy, acyl, acyloxy, alkoxy, alkyloxyalkoxy, amino, alkylamino, dialkylamino, acylamino, carbamoyl, thiol, alkylthio, alkylthiono, sulfonyl, sulfonamido, sulfamoyl, nitro, cyano, free or esterified carboxy, aryl, aryloxy, arylthio, alkenyl, alkynyl, aralkoxy, heteroaralkoxy, heterocyclyl and heterocyclyloxy; or R$_{2b}$ and R$_{3b}$ combined are alkylene which together with the ring atoms to which they are attached form a 5- to 7-membered fused ring; or R$_{2b}$ and R$_{3b}$ combined together with the carbon atom to which they are attached form a fused 5- to 6-membered aromatic or heteroaromatic ring;

X$_b$ is cyano; or

X$_b$ is —NR$_{5b}$C(O)R$_{6b}$, —NR$_{5b}$C(O)OR$_{7b}$, —NR$_{5b}$S(O)$_2$R$_{8b}$, —(CH$_2$)$_r$S(O)$_2$R$_{9b}$ or —OS(O)$_2$R$_{10b}$ in which R$_{5b}$ is hydrogen or lower alkyl;

R$_{6b}$, R$_{7b}$, R$_{8b}$, R$_{13}$ and R$_{10b}$ are, independently from each other, cycloalkyl, aryl, heterocyclyl, aralkyl, heteroaralkyl or (C$_{1-8}$)alkyl optionally substituted with one to four substituents selected from the group consisting of halogen, hydroxy, cycloalkyl, cycloalkoxy, acyl, acyloxy, alkoxy, alkyloxyalkoxy, amino, alkylamino, dialkylamino, acylamino, carbamoyl, thiol, alkylthio, alkylthiono, sulfonyl, sulfonamido, sulfamoyl, nitro, cyano, free or esterified carboxy, aryl, aryloxy, arylthio, alkenyl, alkynyl, aralkoxy, heteroaralkoxy, heterocyclyl and heterocyclyloxy; or R$_{6b}$, R$_{8b}$ and R$_{9b}$ are, independently from each other, —NR$_{13b}$R$_{14b}$ in which R$_{13b}$ and R$_{14b}$ are, independently from each other, hydrogen, alkyl, cycloalkyl, aralkyl, aryl or heterocyclyl; or R$_{13b}$ and R$_{14b}$ combined are alkylene which together with the nitrogen atom to which they are attached form a 4- to 7-membered ring;

r is zero; or

C—X$_b$ is replaced by nitrogen;

or a pharmaceutically acceptable salt thereof.

Preferred are the compounds of formula (Ib$_1$) wherein

X$_b$ is cyano; or

X$_b$ is —NR$_{5b}$S(O)$_2$R$_{8b}$ or —OS(O)$_2$R$_{10b}$ in which

R$_{5b}$ is hydrogen or lower alkyl;

R$_{8b}$ and R$_{10b}$ are, independently from each other, cycloalkyl, aryl, heterocyclyl, aralkyl, heteroaralkyl or (C$_{1-8}$)alkyl optionally substituted with one to four substituents selected from the group consisting of halogen, hydroxy, cycloalkyl, cycloalkoxy, acyl, acyloxy, alkoxy, alkyloxyalkoxy, amino, alkylamino, dialkylamino, acylamino, carbamoyl, thiol, alkylthio, alkylthiono, sulfonyl, sulfonamido, sulfamoyl, nitro, cyano, free or esterified carboxy, aryl, aryloxy, arylthio, alkenyl, alkynyl, aralkoxy, heteroaralkoxy, heterocyclyl and heterocyclyloxy;

or a pharmaceutically acceptable salt thereof.

Especially preferred are the compounds of formula (Ib$_1$), designated as the E group, wherein R$_{5b}$ is hydrogen;

or a pharmaceutically acceptable salt thereof.

Preferred are the compounds in the E group wherein

R$_{8b}$ and R$_{10b}$ are, independently from each other, monocyclic aryl or C$_{(1-4)}$alkyl;

or a pharmaceutically acceptable salt thereof.

Further preferred are the compounds in the E group wherein

R$_1$ is hydrogen or —C(O)R$_2$ in which R$_2$ is monocyclic aryl;

or a pharmaceutically acceptable salt thereof.

Especially preferred are also the compounds of formula (Ib$_1$), designated as the F group, wherein R$_{2b}$, R$_{3b}$ and R$_{4b}$ are, independently from each other, hydrogen, halogen, hydroxy, monocyclic aryl, C$_{(1-4)}$alkoxy or C$_{(1-4)}$alkyl optionally substituted with at least one halogen;

or a pharmaceutically acceptable salt thereof.

Preferred are the compounds in the F group wherein

R$_{5b}$ is hydrogen;

or a pharmaceutically acceptable salt thereof.

Further preferred are the compounds in the F group wherein

R$_{8b}$ and R$_{10b}$ are, independently from each other, monocyclic aryl or C$_{(1-4)}$alkyl;

or a pharmaceutically acceptable salt thereof.

More preferred are the compounds in the F group wherein

R$_1$ is hydrogen or —C(O)R$_2$ in which R$_2$ is monocyclic aryl;

or a pharmaceutically acceptable salt thereof.

Preferred are also the compound of formula (I), designated as the G group, wherein R$_1$ is hydrogen, —C(O)R$_2$, —C(O)NR$_3$R$_4$ or —C(O)OR$_5$ in which R$_2$ and R$_3$ are, independently from each other, hydrogen, cycloalkyl, aryl, heterocyclyl, aralkyl, heteroaralkyl or alkyl optionally substituted with one to four substituents selected from the group consisting of halogen, cycloalkyl, cycloalkoxy, alkoxy, alkyloxyalkoxy, amino, alkylamino, dialkylamino, aryl, aryloxy and heterocyclyl;

R$_4$ and R$_5$ are, independently from each other, cycloalkyl, aryl, heterocyclyl, aralkyl, heteroaralkyl or alkyl optionally substituted with one to four substituents selected from the group consisting of halogen, cycloalkyl, cycloalkoxy, alkoxy, alkyloxyalkoxy, amino, alkylamino, dialkylamino, aryl, aryloxy and heterocyclyl;

U is alkoxy, alkylthio, alkylthiono, sulfonyl, cycloalkyl, aryl, aryloxy, heterocyclyl, alkenyl, alkynyl or (C$_{1-8}$)alkyl optionally substituted with one to four substituents selected from the group consisting of halogen, hydroxy, cycloalkyl, cycloalkoxy, acyl, acyloxy, alkoxy, alkyloxyalkoxy, optionally substituted amino, carbamoyl, thiol, alkylthio, alkylthiono, sulfonyl, sulfamoyl, nitro, cyano, free or esterified carboxy, aryl, aryloxy, arylthio, alkenyl, alkynyl, aralkoxy, heteroaralkoxy, heterocyclyl and heterocyclyloxy;

W and V are, independently from each other, hydrogen, halogen, (C$_{1-3}$)alkyl or (C$_{1-3}$)alkoxy;

or a pharmaceutically acceptable salt thereof.

Preferred are the compounds in the G group, designated as the H group, wherein
U is —$Y_c$—$(CH_2)_p$—$CR_{2c}R_{3c}$—$(CH_2)_t$—$X_c$ in which
$Y_c$ is oxygen or $S(O)_v$ in which v is zero or an integer of 1 or 2; or
$Y_c$ is C≡C; or
$Y_c$ is absent;
p and t are, independently from each other, zero or an integer from 1 to 8;
$R_{2c}$ and $R_{3c}$ are, independently from each other, hydrogen or lower alkyl; or
$R_{2c}$ and $R_{3c}$ combined are alkylene which together with the carbon atom to which they are attached form a 3- to 7-membered ring;
$X_c$ is hydroxy, alkoxy, cycloalkyl, cycloalkoxy, acyl, acyloxy, carbamoyl, optionally substituted amino, cyano, trifluoromethyl, free or esterified carboxy, heterocyclyl, monocyclic aryl or monocyclic aryloxy;
or a pharmaceutically acceptable salt thereof.

Preferred are the compounds in the H group wherein
$R_{2c}$ and $R_{3c}$ are hydrogen;
or a pharmaceutically acceptable salt thereof.

Further preferred are the compounds in the H group wherein
p is zero or an integer from 1 to 3;
t is zero or 1;
$R_{2c}$ and $R_{3c}$ are, independently from each other, hydrogen or lower alkyl;
$X_c$ is hydroxy, carbamoyl, cyano, trifluoromethyl, free or esterified carboxy, heterocyclyl, monocyclic aryl or monocyclic aryloxy;
or a pharmaceutically acceptable salt thereof.

Especially preferred are the compounds in the H group, designated as the I group, wherein
$Y_c$ is C≡C; or
$Y_c$ is absent;
or a pharmaceutically acceptable salt thereof.

Preferred are the compounds in the I group wherein
$Y_c$ is absent;
p is an integer of 5 or 6;
t is zero or 1;
$R_{2c}$ and $R_{3c}$ are lower alkyl;
$X_c$ is hydroxy, cyano or free or esterified carboxy;
or a pharmaceutically acceptable salt thereof.

Further preferred are the compounds in the I group wherein
$R_{2c}$ and $R_{3c}$ are methyl;
or a pharmaceutically acceptable salt thereof.

Especially preferred are the compounds in the I group wherein
$R_1$ is hydrogen or —$C(O)R_2$ in which $R_2$ is monocyclic aryl;
or a pharmaceutically acceptable salt thereof.

Preferred are also the compounds in the I group, designated as the J group, wherein
$Y_c$ is absent;
p is an integer of 4 or 5;
t is zero;
$R_{2c}$ and $R_{3c}$ are hydrogen;
$X_c$ is monocyclic aryloxy;
or a pharmaceutically acceptable salt thereof.

Preferred are the compounds in the J group wherein
$R_1$ is hydrogen or —$C(O)R_2$ in which $R_2$ is monocyclic aryl;
or a pharmaceutically acceptable salt thereof.

Preferred are also the compounds in the J group, designated as the K group, wherein
$Y_c$ is C≡C;
p is an integer of 2 or 3;
t is zero;
$R_{2c}$ and $R_{3c}$ are hydrogen;
$X_c$ is hydroxy, cyano or free or esterified carboxy;
or a pharmaceutically acceptable salt thereof.

Preferred are the compounds in the K group wherein
$R_1$ is hydrogen or —$C(O)R_2$ in which $R_2$ is monocyclic aryl;
or a pharmaceutically acceptable salt thereof.

Preferred are also the compounds in the G group, designated as the L group, wherein
$Q_c$ is monocyclic aryl or 5- to 6-membered heterocyclic ring;
or a pharmaceutically acceptable salt thereof.

Preferred are also the compounds in the G group, designated as the L1 group, wherein
U is —$Y_c$—$(CH_2)_p$—$CR_{2c}R_{3c}$—$(CH_2)_t$—$X_c$ in which
$Y_c$ is oxygen or $S(O)_v$ in which v is zero or an integer of 1 or 2; or
$Y_c$ is C≡C; or
$Y_c$ is absent;
p and t are, independently from each other, zero or an integer from 1 to 8;
$R_{2c}$ and $R_{3c}$ are, independently from each other, hydrogen or lower alkyl; or
$R_{2c}$ and $R_{3c}$ combined are alkylene which together with the carbon atom to which they are attached form a 3- to 7-membered ring;
$X_c$ is monocyclic aryl or 5- to 6-membered heterocyclic ring;
or a pharmaceutically acceptable salt thereof.

Preferred are also the compounds in the G group, designated as the M1 group, wherein
U is monocyclic aryl or 5- to 6-membered heterocyclic ring;
or a pharmaceutically acceptable salt thereof.

Preferred are the compounds in the L group or L1 group, designated as the M group, wherein
$R_{2c}$ and $R_{3c}$ are hydrogen;
or a pharmaceutically acceptable salt thereof.

Preferred are the compounds in the M group or M1 group having the formula (Ic)

[Chemical structure showing a bicyclic aromatic system with $R_{5c}$, $R_{6c}$, $R_{4c}$ substituents on one ring, F substituent, and a sulfonyl-containing heterocyclic ring with HN, N, O, and $R_1$—O groups]

wherein
$R_1$ is hydrogen, —$C(O)R_2$, —$C(O)NR_3R_4$ or —$C(O)OR_5$ in which
$R_2$ and $R_3$ are, independently from each other, hydrogen, cycloalkyl, aryl, heterocyclyl, aralkyl, heteroaralkyl or alkyl optionally substituted with one to four substituents selected from the group consisting of halogen, cycloalkyl, cycloalkoxy, alkoxy, alkyloxyalkoxy, amino, alkylamino, dialkylamino, aryl, aryloxy and heterocyclyl;

$R_4$ and $R_5$ are, independently from each other, cycloalkyl, aryl, heterocyclyl, aralkyl, heteroaralkyl or alkyl optionally substituted with one to four substituents selected from the group consisting of halogen, cycloalkyl, cycloalkoxy, alkoxy, alkyloxyalkoxy, amino, alkylamino, dialkylamino, aryl, aryloxy and heterocyclyl;

$R_{4c}$, $R_{5c}$ and $R_{6c}$ are, independently from each other, hydrogen, hydroxy, halogen, cyano, nitro, alkoxy, alkylthio, alkylthiono, sulfonyl, free or esterified carboxy, carbamoyl, sulfamoyl, optionally substituted amino, cycloalkyl, aryl, heterocyclyl, alkenyl, alkynyl or $(C_{1-8})$alkyl optionally substituted with one to four substituents selected from the group consisting of halogen, hydroxy, cycloalkyl, cycloalkoxy, acyl, acyloxy, alkoxy, alkyloxyalkoxy, optionally substituted amino, carbamoyl, thiol, alkylthio, alkylthiono, sulfonyl, sulfamoyl, nitro, cyano, free or esterified carboxy, aryl, aryloxy, arylthio, alkenyl, alkynyl, aralkoxy, heteroaralkoxy, heterocyclyl and heterocyclyloxy; or C—$R_{4c}$, C—$R_{5c}$ and C—$R_{6c}$ are, independently from each other, replaced by nitrogen;

or a pharmaceutically acceptable salt thereof.

Preferred are the compounds of formula (Ic) wherein
$R_{4c}$ and $R_{5c}$ are hydrogen;

or a pharmaceutically acceptable salt thereof.

Preferred are also the compounds of formula (Ic) wherein
$R_1$ is hydrogen or —C(O)$R_2$ in which $R_2$ is monocyclic aryl;

or a pharmaceutically acceptable salt thereof.

Preferred are also the compounds in the M group having the formula

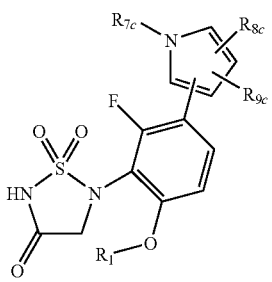

(Ic$_1$)

wherein
$R_1$ is hydrogen, —C(O)$R_2$, —C(O)NR$_3$R$_4$ or —C(O)OR$_5$
in which
$R_2$ and $R_3$ are, independently from each other, hydrogen, cycloalkyl, aryl, heterocyclyl, aralkyl, heteroaralkyl or alkyl optionally substituted with one to four substituents selected from the group consisting of halogen, cycloalkyl, cycloalkoxy, alkoxy, alkyloxyalkoxy, amino, alkylamino, dialkylamino, aryl, aryloxy and heterocyclyl;

$R_4$ and $R_5$ are, independently from each other, cycloalkyl, aryl, heterocyclyl, aralkyl, heteroaralkyl or alkyl optionally substituted with one to four substituents selected from the group consisting of halogen, cycloalkyl, cycloalkoxy, alkoxy, alkyloxyalkoxy, amino, alkylamino, dialkylamino, aryl, aryloxy and heterocyclyl;

$R_{7c}$ is hydrogen, sulfonyl, cycloalkyl, aryl, heterocyclyl or $(C_{1-8})$alkyl optionally substituted with one to four substituents selected from the group consisting of halogen, hydroxy, cycloalkyl, cycloalkoxy, acyl, acyloxy, alkoxy, alkyloxyalkoxy, optionally substituted amino, carbamoyl, thiol, alkylthio, alkylthiono, sulfonyl, sulfamoyl, nitro, cyano, free or esterified carboxy, aryl, aryloxy, arylthio, alkenyl, alkynyl, aralkoxy, heteroaralkoxy, heterocyclyl and heterocyclyloxy;

$R_{8c}$ and $R_{9c}$ are, independently from each other, hydrogen or lower alkyl; or C—$R_{8c}$ and C—$R_{9c}$ are, independently from each other, replaced by nitrogen;

or a pharmaceutically acceptable salt thereof.

Preferred are the compounds of formula (Ic$_1$) wherein
C—$R_{8c}$ is replaced by nitrogen;
$R_{9c}$ is hydrogen;

or a pharmaceutically acceptable salt thereof.

Further preferred are the compounds of formula (Ic$_1$) having the formula

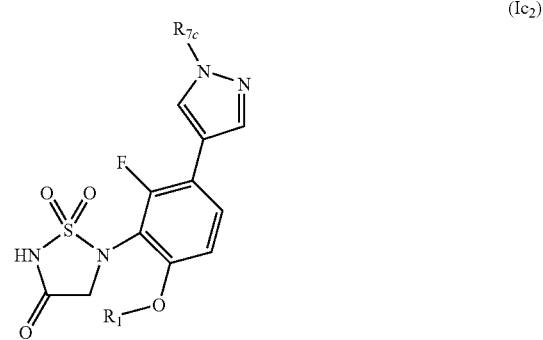

(Ic$_2$)

wherein
$R_1$ is hydrogen, —C(O)$R_2$, —C(O)NR$_3$R$_4$ or —C(O)OR$_5$
in which
$R_2$ and $R_3$ are, independently from each other, hydrogen, cycloalkyl, aryl, heterocyclyl, aralkyl, heteroaralkyl or alkyl optionally substituted with one to four substituents selected from the group consisting of halogen, cycloalkyl, cycloalkoxy, alkoxy, alkyloxyalkoxy, amino, alkylamino, dialkylamino, aryl, aryloxy and heterocyclyl;

$R_4$ and $R_5$ are, independently from each other, cycloalkyl, aryl, heterocyclyl, aralkyl, heteroaralkyl or alkyl optionally substituted with one to four substituents selected from the group consisting of halogen, cycloalkyl, cycloalkoxy, alkoxy, alkyloxyalkoxy, amino, alkylamino, dialkylamino, aryl, aryloxy and heterocyclyl;

$R_{7c}$ is hydrogen, sulfonyl, cycloalkyl, aryl, heterocyclyl or $(C_{1-8})$alkyl optionally substituted with one to four substituents selected from the group consisting of halogen, hydroxy, cycloalkyl, cycloalkoxy, acyl, acyloxy, alkoxy, alkyloxyalkoxy, optionally substituted amino, carbamoyl, thiol, alkylthio, alkylthiono, sulfonyl, sulfamoyl, nitro, cyano, free or esterified carboxy, aryl, aryloxy, arylthio, alkenyl, alkynyl, aralkoxy, heteroaralkoxy, heterocyclyl and heterocyclyloxy;

or a pharmaceutically acceptable salt thereof.

Preferred are the compounds of formula (Ic$_2$) wherein
R$_{7c}$ is —(CH$_2$)$_p$—CR$_{10c}$R$_{11c}$—(CH$_2$)$_t$—Z$_c$ in which
  p and t are, independently from each other, zero or an integer from 1 to 6;
  R$_{10c}$ and R$_{11c}$ are, independently from each other, hydrogen or lower alkyl; or
  R$_{10c}$ and R$_{11c}$ combined are alkylene which together with the carbon atom to which they are attached form a 3- to 7-membered ring;
  Z$_c$ is hydroxy, alkoxy, cycloalkyl, cycloalkoxy, acyl, acyloxy, carbamoyl, optionally substituted amino, cyano, trifluoromethyl, free or esterified carboxy, heterocyclyl, monocyclic aryl or monocyclic aryloxy;
or a pharmaceutically acceptable salt thereof.

Further preferred are the compounds of formula (Ic$_2$) wherein
  p is an integer from 1 to 3;
  t is zero or 1;
  R$_{10c}$ and R$_{11c}$ are, independently from each other, hydrogen or lower alkyl;
  Z$_c$ is hydroxy, carbamoyl, cyano, trifluoromethyl, free or esterified carboxy, heterocyclyl, monocyclic aryl or monocyclic aryloxy;
or a pharmaceutically acceptable salt thereof.

More preferred are the compounds of formula (Ic$_2$) wherein
  R$_{10c}$ and R$_{11c}$ are hydrogen;
  Z$_c$ is hydroxy, cyano or free or esterified carboxy;
or a pharmaceutically acceptable salt thereof.

Most preferred are the compounds of formula (Ic$_2$) wherein
  R$_1$ is hydrogen or —C(O)R$_2$ in which R$_2$ is monocyclic aryl;
or a pharmaceutically acceptable salt thereof.

Particular embodiments of the invention are:
Methanesulfonic acid 2-[3-fluoro-5-hydroxy-4-(1,1,4-trioxo-1,2,5-thiadiazolidin-2-yl)-benzyl]-4-methylphenyl ester;
Methanesulfonic acid 2-[3-fluoro-5-hydroxy-4-(1,1,4-trioxo-1,2,5-thiadiazolidin-2-yl)-benzyl]-5-methylphenyl ester;
Methanesulfonic acid 2-[3-fluoro-5-hydroxy-4-(1,1,4-trioxo-1,2,5-thiadiazolidin-2-yl)-benzyl]-6-methylphenyl ester;
Methanesulfonic acid 2-[3-fluoro-5-hydroxy-4-(1,1,4-trioxo-1,2,5-thiadiazolidin-2-yl)-benzyl]-phenyl ester;
N-{2-[3-Fluoro-5-hydroxy-4-(1,1,4-trioxo-1,2,5-thiadiazolidin-2-yl)-benzyl]-5-methylphenyl}-methanesulfonamide;
N-{2-[3-Fluoro-5-hydroxy-4-(1,1,4-trioxo-1,2,5-thiadiazolidin-2-yl)-benzyl]-4-methylphenyl}-methanesulfonamide;
N-{2-[3-Fluoro-5-hydroxy-4-(1,1,4-trioxo-1,2,5-thiadiazolidin-2-yl)-benzyl]-phenyl}-methanesulfonamide;
5-(4-Benzyl-2-fluoro-6-hydroxy-phenyl)-1,1-dioxo-1,2,5-thiadiazolidin-3-one;
5-(2-Fluoro-6-hydroxy-4-methylphenyl)-1,1-dioxo-1,2,5-thiadiazolidin-3-one;
Benzoic acid 5-benzyl-3-fluoro-2-(1,1,4-trioxo-1,2,5-thiadiazolidin-2-yl)-phenyl ester;
Benzoic acid 3-fluoro-5-methyl-2-(1,1,4-trioxo-1,2,5-thiadiazolidin-2-yl)-phenyl ester;
5-(4-Cyclobutylmethyl-2-fluoro-6-hydroxyphenyl)-1,1-dioxo-1,2,5-thiadiazolidin-3-one potassium salt;
5-(4-Cyclohexylmethyl-2-fluoro-6-hydroxyphenyl)-1,1-dioxo-1,2,5-thiadiazolidin-3-one;
7-[2-Fluoro-4-hydroxy-3-(1,1,4-trioxo-1,2,5-thiadiazolidin-2-yl)-phenyl]-2,2-dimethylheptanenitrile;
5-(2,4-Difluoro-6-hydroxyphenyl)-1,1-dioxo-1,2,5-thiadiazolidin-3-one;
5-(1-Fluoro-3-hydroxy-7-methylnaphthalen-2-yl)-1,1-dioxo-1,2,5-thiadiazolidin-3-one;
5-(1-Fluoro-3-hydroxynaphthalen-2-yl)-1,1-dioxo-1,2,5-thiadiazolidin-3-one;
5-(7-Ethyl-1-fluoro-3-hydroxy-5,6,7,8-tetrahydronaphthalen-2-yl)-1,1-dioxo-1,2,5-thiadiazolidin-3-one;
5-[1-Fluoro-3-hydroxy-7-(5-hydroxy-4,4-dimethylpentyl)-naphthalen-2-yl]-1,1-dioxo-1,2,5-thiadiazolidin-3-one;
5-[8-Fluoro-6-hydroxy-7-(1,1,4-trioxo-1,2,5-thiadiazolidin-2-yl)-naphthalen-2-yl]-2,2-dimethyl-pentanoic acid;
Benzoic acid 4-fluoro-6-methyl-3-(1,1,4-trioxo-1,2,5-thiadiazolidin-2-yl)-naphthalen-2-yl ester;
Benzoic acid 6-ethyl-4-fluoro-3-(1,1,4-trioxo-1,2,5-thiadiazolidin-2-yl)-5,6,7,8-tetrahydronaphthalen-2-yl ester;
Benzoic acid 4-fluoro-3-(1,1,4-trioxo-1,2,5-thiadiazolidin-2-yl)-naphthalen-2-yl ester;
Benzoic acid 4-fluoro-6-(5-hydroxy-4,4-dimethylpentyl)-3-(1,1,4-trioxo-1,2,5-thiadiazolidin-2-yl)-naphthalen-2-yl ester;
Benzoic acid 3-fluoro-5-(2-methanesulfonyloxy-5-methylbenzyl)-2-(1,1,4-trioxo-1,2,5-thiadiazolidin-2-yl)-phenyl ester;
Benzoic acid 3-fluoro-5-(2-methanesulfonyloxy-4-methylbenzyl)-2-(1,1,4-trioxo-1,2,5-thiadiazolidin-2-yl)-phenyl ester;
Benzoic acid 4-(6-cyano-6,6-dimethylhexyl)-3-fluoro-2-(1,1,4-trioxo-1,2,5-thiadiazolidin-2-yl)-phenyl ester;
Benzoic acid 3-fluoro-5-(2-methanesulfonylamino-5-methylbenzyl)-2-(1,1,4-trioxo-1,2,5-thiadiazolidin-2-yl)-phenyl ester;
Benzoic acid 3-fluoro-5-(2-methanesulfonylamino-4-methylbenzyl)-2-(1,1,4-trioxo-1,2,5-thiadiazolidin-2-yl)-phenyl ester;
Benzoic acid 3-fluoro-5-(2-methanesulfonyloxy-3-methylbenzyl)-2-(1,1,4-trioxo-1,2,5-thiadiazolidin-2-yl)-phenyl ester;
5-(4-Ethyl-2-fluoro-6-hydroxyphenyl)-1,1-dioxo-1-[1,2,5]thiadiazolidin-3-one;
5-(4-Cyclopentylmethyl-2-fluoro-6-hydroxyphenyl)-1,1-dioxo-1-[1,2,5]thiadiazolidin-3-one;
5-(2,3-Difluoro-6-hydroxy-4-methylphenyl)-1,1-dioxo-1,2,5]thiadiazolidin-3-one;
5-(2,3-Difluoro-6-hydroxyphenyl)-1,1-dioxo-1,2,5]thiadiazolidin-3-one;
1,1-Dioxo-5-(2,3,5-trifluoro-6-hydroxy-phenyl)-1,2,5]thiadiazolidin-3-one potassium salt;
1,1-Dioxo-5-(2,3,5-trifluoro-6-hydroxy-phenyl)-1,2,5]thiadiazolidin-3-one;
5-(2-Fluoro-6-hydroxyphenyl)-1,1-dioxo-[1,2,5]thiadiazolidin-3-one potassium salt;
5-(2-Fluoro-6-hydroxyphenyl)-1,1-dioxo-[1,2,5]thiadiazolidin-3-one;
2-(4-{3-[3-Fluoro-5-hydroxy-4-(1,1,4-trioxo-1-[1,2,5]thiadiazolidin-2-yl)-phenyl]-propionylamino}-butoxy)-6-hydroxy-benzoic acid methyl ester potassium salt;
2-(4-{3-[3-Fluoro-5-hydroxy-4-(1,1,4-trioxo-1-[1,2,5]thiadiazolidin-2-yl)-phenyl]-propionylamino}-butoxy)-6-hydroxy-benzoic acid methyl ester;
7-[2-Fluoro-4-hydroxy-3-(1,1,4-trioxo-1-[1,2,5]thiadiazolidin-2-yl)-phenyl]-2,2-dimethylheptanoic acid dipotassium salt;
7-[2-Fluoro-4-hydroxy-3-(1,1,4-trioxo-1-[1,2,5]thiadiazolidin-2-yl)-phenyl]-2,2-dimethylheptanoic acid;

5-(7-Bromo-1-fluoro-3,6-dihydroxynaphthalen-2-yl)-1,1-dioxo-[1,2,5]thiadiazolidin-3-one;

5-[8-Fluoro-6-hydroxy-7-(1,1,4-trioxo-1-[1,2,5]thiadiazolidin-2-yl)-naphthalen-2-yl]-2,2-dimethylpentanoic acid isopropyl ester potassium salt;

5-[8-Fluoro-6-hydroxy-7-(1,1,4-trioxo-1-[1,2,5]thiadiazolidin-2-yl)-naphthalen-2-yl]-2,2-dimethylpentanoic acid isopropyl ester;

5-[8-Fluoro-6-hydroxy-7-(1,1,4-trioxo-[1,2,5]thiadiazolidin-2-yl)-naphthalen-2-yl]-2,2-dimethyl-pentanoic acid methyl ester;

5-[8-Fluoro-6-hydroxy-7-(1,1,4-trioxo-[1,2,5]thiadiazolidin-2-yl)-naphthalen-2-yl]-2,2-dimethyl-pentanoic acid ethyl ester;

5-[8-Fluoro-6-hydroxy-7-(1,1,4-trioxo-[1,2,5]thiadiazolidin-2-yl)-naphthalen-2-yl]-2,2-dimethyl-pentanoic acid butyl ester;

(S)-5-[8-Fluoro-6-hydroxy-7-(1,1,4-trioxo-[1,2,5]thiadiazolidin-2-yl)-naphthalen-2-yl]-2-methyl-pentanoic acid;

(R)-5-[8-Fluoro-6-hydroxy-7-(1,1,4-trioxo-[1,2,5]thiadiazolidin-2-yl)-naphthalen-2-yl]-2-methyl-pentanoic acid;

5-[1-Fluoro-3-hydroxy-7-(4-hydroxy-4-methyl-pentyl)-naphthalen-2-yl]-1,1-dioxo-[1,2,5]thiadiazolidin-3-one;

5-[8-Fluoro-6-hydroxy-7-(1,1,4-trioxo-[1,2,5]thiadiazolidin-2-yl)-naphthalen-2-yl]-pentanoic acid;

4-[8-Fluoro-6-hydroxy-7-(1,1,4-trioxo-[1,2,5]thiadiazolidin-2-yl)-naphthalen-2-yl]-butyric acid;

5-[8-Fluoro-6-hydroxy-7-(1,1,4-trioxo-[1,2,5]thiadiazolidin-2-yl)-naphthalen-2-yl]-pentanoic acid ethyl ester;

3-{3-[8-Fluoro-6-hydroxy-7-(1,1,4-trioxo-[1,2,5]thiadiazolidin-2-yl)-naphthalen-2-yl]-phenyl}-propionic acid ethyl ester;

3-{3-[8-Fluoro-6-hydroxy-7-(1,1,4-trioxo-[1,2,5]thiadiazolidin-2-yl)-naphthalen-2-yl]-phenyl}-propionic acid;

3-[8-Fluoro-6-hydroxy-7-(1,1,4-trioxo-[1,2,5]thiadiazolidin-2-yl)-naphthalen-2-yl]-benzonitrile;

3-[8-Fluoro-6-hydroxy-7-(1,1,4-trioxo-[1,2,5]thiadiazolidin-2-yl)-naphthalen-2-yl]-benzoic acid; and 5-[1-Fluoro-3-hydroxy-7-(4-formyl-4-methyl-pentyl)-naphthalen-2-yl]-1,1-dioxo-[1,2,5]thiadiazolidin-3-one;

5-[8-Fluoro-6-hydroxy-7-(1,1,4-trioxo-[1,2,5]thiadiazolidin-2-yl)-naphthalen-2-yl]-pentanoic acid methyl ester;

5-[7-(4,4-Dimethyl-pentyl)-1-fluoro-3-hydroxy-naphthalen-2-yl]-1,1-dioxo-[1,2,5]thiadiazolidin-3-one;

or a pharmaceutically acceptable salt thereof.

The compounds of the invention depending on the nature of the substituents, may possess one or more asymmetric centers. The resulting diastereoisomers, enantiomers and geometric isomers are encompassed by the instant invention.

Compounds of formula (I) may be prepared starting, e.g., by cyclizing compounds of the formula

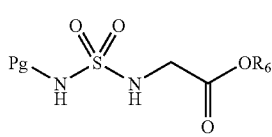

(II)

wherein Pg is an appropriate N-protecting group such as 4-methoxybenzyl, 2,4-dimethoxybenzyl or 2-trimethylsilyl-ethyl, and $R_6$ is hydrogen to afford compounds of the formula

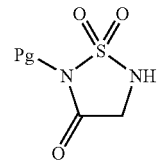

(III)

wherein Pg has a meaning as defined herein above, by treatment with a coupling agent such as diisopropyl carbodiimide (DIC) or 1-ethyl-3-(3-dimethylaminopropyl)carbodiimide hydrochloride (EDCl) in the presence a base such as triethylamine (TEA) or N-methyl-morpholine (NMM) in an organic solvent such as tetrahydrofuran (THF), N,N-dimethyl-formamide (DMF) or dichoromethane (DCM). The reaction may be carried out in the presence of an additive such as of hydroxybenzotriazole (HOBt).

Compounds of formula (II) wherein $R_6$ is hydrogen may be obtained from compounds of formula (II) wherein $R_6$ is an alkyl group according to methods well known in the art, e.g. compounds of formula (II) in which $R_6$ is methyl or ethyl can be treated with an aqueous base such as sodium or potassium hydroxide in an organic solvent such as THF, 1,4-dioxane, methanol (MeOH) or ethanol (EtOH) to afford compounds of formula (II) wherein $R_6$ is hydrogen, or compounds of formula (II) in which $R_6$ is t-butyl may be treated with an acid such as hydrochloric acid (HCl) or trifluoroacetic acid (TFA) in an organic solvent such as DCM or ethyl acetate (EtOAc) to afford compounds of formula (II) wherein $R_6$ is hydrogen.

Compounds of formula (II) wherein $R_6$ is an alkyl group such as methyl, ethyl or t-butyl, and the like, may be obtained analogously to a literature procedure described by Ducry et al. in *Helvetica Chimica Acta*, 1999, 82, 2432.

Resulting compounds of formula (III) wherein Pg has a meaning as defined herein can then be coupled with a variety of boronic acid derivatives of the formula

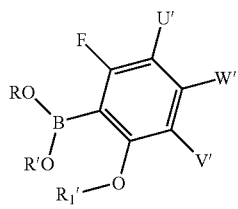

(IV)

wherein $R_1'$, V', W' and U' have meanings as defined herein for $R_1$, V, W and U, or $R_1'$, V', W' and U' are groups convertible to $R_1$, V, W and U, respectively, and R and R' are hydrogen or lower alkyl, or R and R' combined are alkylene which together with the boron and the oxygen atoms form a 5- or 6-membered ring, in the presence of a copper catalyst such as copper(II) acetate and a base such as cesium(II) carbonate ($Cs_2CO_3$) or TEA in an organic solvent such as THF, 1,4-dioxane or DCM to form compounds of the formula

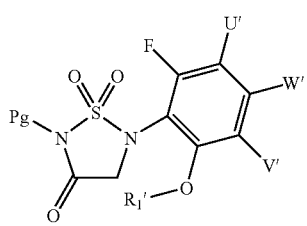

(V)

wherein Pg, $R_1'$, V', W' and U' have meanings as defined herein for $R_1$, V, W and U, or $R_1'$, V', W' and U' are groups convertible to $R_1$, V, W and U, respectively. Alternatively, compounds of formula (III) may be coupled with a boroxine derivative corresponding to a boronic acid derivative of formula (IV) as described, e.g., by Chan et al. in *Tet. Lett.* 2003, 44, 3863.

Compounds of formula (IV) are known, or if they are novel, they may be prepared using methods well known in the art, or as illustrated herein in the Examples, or modifications thereof.

Alternatively, compounds of formula (V) wherein $R_1'$, V', W', $R_4'$ and $R_5'$ have meanings as defined herein for $R_1$, V, W, $R_4$ and $R_5$, or $R_1'$, V', W', $R_4'$ and $R_5'$ are groups convertible to $R_1$, V, W, $R_4$ and $R_5$, respectively, may be obtained by reacting a compound of formula (III) wherein Pg has a meaning as defined herein with compounds of the formula

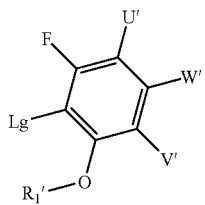

(VI)

wherein Lg represents a leaving group such as halide or trifluoromethanesulfonate, preferably fluoride or chloride, and $R_1'$, V', W' and U' have meanings as defined herein for $R_1$, V, W and U, or $R_1'$, V', W' and U' are groups convertible to $R_1$, V, W and U, respectively, using conditions well know in the art or using methods described herein or modifications thereof, e.g., a compound of formula (III) may be first treated with a base such as $Cs_2CO_3$, or sodium, lithium or potassium bis(trimethylsilyl)amide in an inert organic solvent such as THF or 1,4-dioxane followed by reaction with a compound of formula (VI) at a temperature ranging from room temperature (RT) to 110° C.

Compounds of formula (VI) are known, or if they are novel, they may be prepared using methods well known in the art, or as illustrated herein in the Examples, or modifications thereof.

Compounds of formula (V) wherein Pg, $R_1'$, V', W' and U' have meanings as defined herein for $R_1$, V, W and U, or $R_1'$, V', W' and U' are groups convertible to $R_1$, V, W and U, respectively, can be converted to compounds of the formula

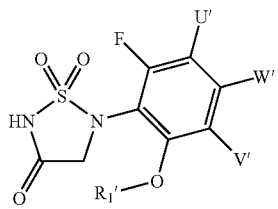

(I')

by removal of the N-protecting group according to methods well known in the art, e.g. in particular when Pg is 4-methoxybenzyl or 2,4-dimethoxybenzyl group using hydrogen in the presence of a catalyst such as palladium on carbon in a polar organic solvent such as MeOH or EtOAc, or by treatment with an acid such as TFA in an organic solvent such as DCM, preferably in the presence of an additive such as t-butyldimethylsilane or triethylsilane, or in particular when Pg is trimethylsilylethyl group using a fluoride reagent such as tetra-n-butylammoniumfluoride in an organic solvent such as THF or 1,4-dioxane.

In addition, compounds of formula (I') wherein $R_1'$, V', W' and U' have meanings as defined herein for $R_1$, V, W and U, or $R_1'$, V', W' and U' are groups convertible to $R_1$, V, W and U, respectively, may be prepared by condensing compounds of the formula

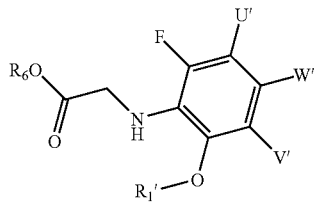

(VII)

wherein $R_6$ has a meaning as defined herein above, with sulfamoyl chloride analogs of the formula $ClS(O)_2NHR_7$ (VIII)

wherein $R_7$ is hydrogen or alkoxycarbonyl such as t-butoxycarbonyl or 2-trimethylsilyl-ethoxycarbonyl in the presence of a base such as TEA or NMM in an organic solvent such as acetonitrile (MeCN), DCM or THF to form compounds of the formula

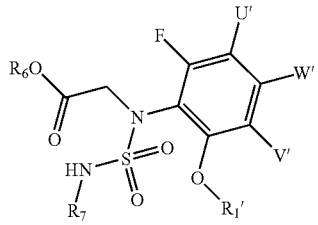

(IX)

wherein $R_6$ and $R_7$ have meanings as defined herein, and $R_1'$, V', W' and U' have meanings as defined herein for $R_1$, V, W and U, or $R_1'$, V', W' and U' are groups convertible to $R_1$, V, W and U, respectively.

Compounds of formula (VIII) wherein $R_7$ is alkoxycarbonyl may be obtained by reacting chlorosulfonyl isocyanate with the appropriate alcohol in an organic solvent such as MeCN, DCM or THF.

Compounds of formula (VII) may be prepared using methods well known in the art or according to methods described herein or modifications thereof, e.g., under conditions of reductive amination, or according to the method described by Tohru Fukuyama et al. in *Tet. Lett.*, 1997, 38 (33), 5831; or by reacting amines of the formula

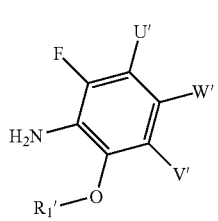

(X)

wherein $R_1'$, V', W' and U' have meanings as defined herein for $R_1$, V, W and U, or $R_1'$, V', W' and U' are groups convertible to $R_1$, V, W and U, respectively, with an acetate of the formula $$\text{Lg'-CH}_2\text{—C(O)—O—R}_6 \quad\quad\quad (XI)$$

wherein Lg' and $R_6$ have meanings as defined herein, in the presence of a base such as TEA or NMM in an inert solvent such as THF or 1,4-dioxane.

Amines of formula (X) are known, or if they are novel, they may be obtained according to methods well known in the art, or as described herein in the illustrative Examples, or using modifications thereof.

Compounds of formula (IX) wherein $R_6$ has a meaning as defined herein, and $R_1'$, V', W' and U' have meanings as defined herein for $R_1$, V, W and U, or $R_1'$, V', W' and U' are groups convertible to $R_1$, V, W and U, respectively, and $R_7$ is alkoxycarbonyl may be converted to compounds of formula (IX) wherein $R_7$ is hydrogen according to methods known in the art or using methods described herein or modifications thereof, e.g., compounds of formula (IX) wherein $R_7$ is t-butoxycarbonyl may be treated with an acid such as TFA, neat or in an extrinsic organic solvent such as DCM, or compounds of formula (IX) wherein $R_7$ is 2-trimethylsilylethoxycarbonyl may be treated with a fluoride reagent such as tetra-n-butylammoniumfluoride in an organic solvent such as THF or 1,4-dioxane to afford compounds of formula (IX) wherein $R_7$ is hydrogen.

Compounds of formula (IX) wherein $R_6$ has a meaning as defined herein, and $R_1'$, V', W' and U' have meanings as defined herein for $R_1$, V, W and U, or $R_1'$, V', W' and U' are groups convertible to $R_1$, V, W and U, respectively, and $R_7$ is hydrogen can be cyclized to form compounds of formula (I') using methods and conditions well known in the art or as illustrated with Examples herein or modifications thereof.

Alternatively, compounds of formula (IX) wherein $R_6$ has a meaning as defined herein; $R_1'$, V', W' and U' have meanings as defined herein for $R_1$, V, W and U, or $R_1'$, V', W' and U' are groups convertible to $R_1$, V, W and U, respectively; and $R_7$ is hydrogen, may be obtained by first condensing amines of formula (X) with sulfamide in an aqueous solution and in the presence of a base such as sodium bicarbonate ($NaHCO_3$) at an elevated temperature, preferably at the boiling point of the solution, to afford compounds of the formula

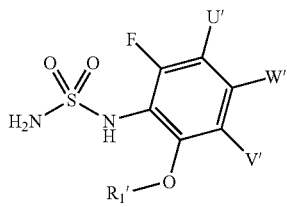

(XII)

wherein $R_1'$, V', W' and U' have meanings as defined herein for $R_1$, V, W and U, or $R_1'$, V', W' and U' are groups convertible to $R_1$, V, W and U, respectively. Compound of formula (XII) may then be converted to compound of formula (IX) in which $R_7$ is hydrogen by the reaction with acetates of formula (XI) in the presence of a base such as sodium hydride in an inert solvent such as THF or DMF.

In starting compounds and intermediates which are converted to the compounds of the invention in a manner described herein, functional groups present, such as amino, thiol, carboxyl, and hydroxy groups, are optionally protected by conventional protecting groups that are common in preparative organic chemistry. Protected amino, thiol, carboxyl, and hydroxyl groups are those that can be converted under mild conditions into free amino thiol, carboxyl and hydroxyl groups without the molecular framework being destroyed or other undesired side reactions taking place.

The purpose of introducing protecting groups is to protect the functional groups from undesired reactions with reaction components under the conditions used for carrying out a desired chemical transformation. The need and choice of protecting groups for a particular reaction is known to those skilled in the art and depends on the nature of the functional group to be protected (hydroxyl group, amino group, etc.), the structure and stability of the molecule of which the substituent is a part and the reaction conditions.

Well known protecting groups that meet these conditions and their introduction and removal are described, for example, in McOmie, "*Protective Groups in Organic Chemistry*", Plenum Press, London, N.Y. (1973); and Greene and Wuts, "*Protective Groups in Organic Synthesis*", John Wiley and Sons, Inc, New York (1999).

The above mentioned reactions are carried out according to standard methods, in the presence or absence of diluent, preferably such as are inert to the reagents and are solvents thereof, of catalysts, condensing or said other agents respectively and/or inert atmospheres, at low temperatures, room temperature or elevated temperatures (preferably at or near the boiling point of the solvents used), and at atmospheric or super-atmospheric pressure. The preferred solvents, catalysts and reaction conditions are set forth in the appended illustrative Examples.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure antipodes.

Compounds of the invention and intermediates can also be converted into each other according to methods generally known per se.

The invention also relates to any novel starting materials, intermediates and processes for their manufacture.

Depending on the choice of starting materials and methods, the new compounds may be in the form of one of the possible isomers or mixtures thereof, for example, as substantially pure geometric (cis or trans) isomers, optical isomers (enantiomers, antipodes), racemates, or mixtures thereof. The aforesaid possible isomers or mixtures thereof are within the purview of this invention.

Any resulting mixtures of isomers can be separated on the basis of the physico-chemical differences of the constituents, into the pure geometric or optical isomers, diastereoisomers, racemates, for example by chromatography and/or fractional crystallization.

Any resulting racemates of final products or intermediates can be resolved into the optical antipodes by known methods, e.g. by separation of the diastereoisomeric salts thereof, obtained with an optically active acid or base, and liberating the optically active acidic or basic compound. The carboxylic acid intermediates can thus be resolved into their optical antipodes e.g. by fractional crystallization of D- or L-(alpha-methylbenzylamine, cinchonidine, cinchonine, quinine, quinidine, ephedrine, dehydroabietylamine, brucine or strychnine)-salts.

Racemic products can also be resolved by chiral chromatography, e.g. high pressure liquid chromatography using a chiral adsorbent.

Finally, compounds of the invention are either obtained in the free form, as a salt thereof if salt forming groups are present or as prodrug derivatives thereof.

In particular, the NH-group of the 1,1-dioxo-1,2,5-thiadiazolidin-3-one moiety, may be converted into salts with pharmaceutically acceptable bases. Salts may be formed using conventional methods, advantageously in the presence of an ethereal or alcoholic solvent, such as a lower alkanol. From the solutions of the latter, the salts may be precipitated with ethers, e.g. diethyl ether. Resulting salts may be converted into the free compounds by treatment with acids. These or other salts can also be used for purification of the compounds obtained.

Compounds of the invention having basic groups can be converted into acid addition salts, especially pharmaceutically acceptable salts. These are formed, for example, with inorganic acids, such as mineral acids, for example sulfuric acid, a phosphoric or hydrohalic acid, or with organic carboxylic acids, such as $(C_{1-4})$alkanecarboxylic acids which, for example, are unsubstituted or substituted by halogen, for example acetic acid, such as saturated or unsaturated dicarboxylic acids, for example oxalic, succinic, maleic or fumaric acid, such as hydroxy-carboxylic acids, for example glycolic, lactic, malic, tartaric or citric acid, such as amino acids, for example aspartic or glutamic acid, or with organic sulfonic acids, such as $(C_{1-4})$alkyl-sulfonic acids (for example methanesulfonic acid) or arylsulfonic acids which are unsubstituted or substituted (for example by halogen). Preferred are salts formed with hydrochloric acid, methanesulfonic acid and maleic acid.

Prodrug derivatives of any compound of the present invention are derivatives of said compounds which following administration release the parent compound in vivo via some chemical or physiological process, e.g., a prodrug on being brought to the physiological pH or through enzyme action is converted to the parent compound. Exemplary prodrug derivatives are, e.g., esters of free carboxylic acids and S-acyl and O-acyl derivatives of thiols, alcohols or phenols, wherein acyl has a meaning as defined herein. Preferred are pharmaceutically acceptable ester derivatives convertible by solvolysis under physiological conditions to the parent carboxylic acid, e.g., lower alkyl esters, cycloalkyl esters, lower alkenyl esters, benzyl esters, mono- or di-substituted lower alkyl esters, such as the ω-(amino, mono- or di-lower alkylamino, carboxy, lower alkoxycarbonyl)-lower alkyl esters, the α-(lower alkanoyloxy, lower alkoxycarbonyl or di-lower alkylaminocarbonyl)-lower alkyl esters, such as the pivaloyloxymethyl ester and the like conventionally used in the art.

In view of the close relationship between the free compounds, the prodrug derivatives and the compounds in the form of their salts, whenever a compound is referred to in this context, a prodrug derivative and a corresponding salt is also intended, provided such is possible or appropriate under the circumstances.

The compounds, including their salts, can also be obtained in the form of their hydrates, or include other solvents used for their crystallization.

As described herein above, the compounds of the present invention are inhibitors of PTPases and, thus, may be employed for the treatment of conditions mediated by the PTPases. Accordingly, the compounds of formula (I) may be employed for treatment of insulin resistance, glucose intolerance, obesity, diabetes mellitus, hypertension and ischemic diseases of the large and small blood vessels, conditions accompanying type 2 diabetes including dyslipidemia, e.g., hyperlipidemia and hypertriglyceridemia, atherosclerosis, vascular restenosis, irritable bowel syndrome, pancreatitis, adipose cell tumors and carcinomas such as liposarcoma, dyslipidemia, and other disorders where insulin resistance is indicated. In addition, the compounds of the present invention may be employed to treat cancer (such as prostate or breast cancer), osteoporosis, neurodegenerative and infectious diseases, and diseases involving inflammation and the immune system.

Accordingly, the compounds of formula (I) may be employed for treatment of insulin resistance, glucose intolerance, type 2 diabetes, renal insufficiency (diabetic and non-diabetic), diabetic nephropathy, glomerulonephritis, glomerular sclerosis, proteinuria of primary renal disease, diabetic retinopathy, obesity, all types of heart failures including acute and chronic congestive heart failure, left ventricular dysfunction and hypertrophic cardiomyopathy, diabetic cardiac myopathy, supraventricular and ventricular arrhythmias, atrial fibrillation and atrial flutter, hypertension, primary and secondary pulmonary hypertension, renal vascular hypertension, dyslipidemia, atherosclerosis, ischemic diseases of the large and small blood vessels, angina pectoris (whether unstable or stable), myocardial infarction and its sequelae, ischemia/reperfusion injury, detrimental vascular remodeling including vascular restenosis, management of other vascular disorders including migraine, peripheral vascular disease and Raynaud's disease, irritable bowel syndrome, pancreatitis, cancer (such as prostate or breast cancer), osteoporosis, multiple sclerosis, stroke, spinal cord injury, neurodegenerative diseases such as Alzheimer's, Parkinson's and polyglutamine disorders such as Huntington's and spinocerebellar ataxia, infectious diseases, and diseases involving inflammation and the immune system and diseases involving muscle degeneration.

The present invention further provides pharmaceutical compositions comprising a therapeutically effective amount of a pharmacologically active compound of the instant invention, alone or in combination with one or more pharmaceutically acceptable carriers.

The pharmaceutical compositions according to the invention are those suitable for enteral, such as oral or rectal; transdermal and parenteral administration to mammals, including man, for the treatment of conditions mediated by PTPase activity, in particular, PTP-1B and TC PTP activity. Such conditions include e.g. insulin resistance, glucose intolerance, obesity, diabetes mellitus, hypertension and ischemic diseases of the large and small blood vessels, conditions accompanying type 2 diabetes including dyslipidemia, e.g., hyperlipidemia and hypertriglyceridemia, atherosclerosis, vascular restenosis, irritable bowel syndrome, pancreatitis, adipose cell tumors and carcinomas such as liposarcoma, dyslipidemia, and other disorders where insulin resistance is indicated. In addition, the compounds of the present invention may be employed to treat cancer (such as prostate or breast cancer), osteoporosis, neurodegenerative and infectious diseases, and diseases involving inflammation and the immune system.

Thus, the pharmacologically active compounds of the invention may be employed in the manufacture of pharmaceutical compositions comprising an effective amount thereof in conjunction or admixture with excipients or carriers suitable for either enteral or parenteral application. Preferred are tablets and gelatin capsules comprising the active ingredient together with:

a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired
d) disintegrants, e.g., starches, agar, alginic acid or its sodium salt, or effervescent mixtures; and/or
e) absorbants, colorants, flavors and sweeteners. Injectable compositions are preferably aqueous isotonic solutions or suspensions, and suppositories are advantageously prepared from fatty emulsions or suspensions.

Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, preferably about 1-50%, of the active ingredient.

Suitable formulations for transdermal application include a therapeutically effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Accordingly, the present invention provides pharmaceutical compositions as described above for the treatment of conditions mediated by PTPases, preferably, insulin resistance, glucose intolerance, obesity, diabetes mellitus, hypertension and ischemic diseases of the large and small blood vessels, conditions accompanying type 2 diabetes including dyslipidemia, e.g., hyperlipidemia and hypertriglyceridemia, atherosclerosis, vascular restenosis, irritable bowel syndrome, pancreatitis, adipose cell tumors and carcinomas such as liposarcoma, dyslipidemia, and other disorders where insulin resistance is indicated. In addition, the compounds of the present invention may be employed to treat cancer (such as prostate or breast cancer), osteoporosis, neurodegenerative and infectious diseases, and diseases involving inflammation and the immune system.

Accordingly, the present invention provides pharmaceutical compositions as described above for the treatment of conditions mediated by PTPases, preferably, insulin resistance, glucose intolerance, type 2 diabetes, renal insufficiency (diabetic and non-diabetic), diabetic nephropathy, glomerulonephritis, glomerular sclerosis, proteinuria of primary renal disease, diabetic retinopathy, obesity, all types of heart failures including acute and chronic congestive heart failure, left ventricular dysfunction and hypertrophic cardiomyopathy, diabetic cardiac myopathy, supraventricular and ventricular arrhythmias, atrial fibrillation and atrial flutter, hypertension, primary and secondary pulmonary hypertension, renal vascular hypertension, dyslipidemia, atherosclerosis, ischemic diseases of the large and small blood vessels, angina pectoris (whether unstable or stable), myocardial infarction and its sequelae, ischemia/reperfusion injury, detrimental vascular remodeling including vascular restenosis, management of other vascular disorders including migraine, peripheral vascular disease and Raynaud's disease, irritable bowel syndrome, pancreatitis, cancer (such as prostate or breast cancer), osteoporosis, multiple sclerosis, stroke, spinal cord injury, neurodegenerative diseases such as Alzheimer's, Parkinson's and polyglutamine disorders such as Huntington's and spinocerebellar ataxia, infectious diseases, and diseases involving inflammation and the immune system and diseases involving muscle degeneration.

The pharmaceutical compositions may contain a therapeutically effective amount of a compound of the invention as defined above, either alone or in a combination with another therapeutic agent, e.g., each at an effective therapeutic dose as reported in the art. Such therapeutic agents include:

a) anti-diabetic agents, such as insulin, insulin derivatives and mimetics; insulin secretagogues such as the sulfonylureas, e.g., Glipizide, glyburide and Amaryl; insulinotropic sulfonylurea receptor ligands such as meglitinides, e.g., nateglinide and repaglinide; thiazolidone derivatives such as glitazones, e.g., pioglitazone and rosiglitazone; glucokinase activators; GSK3 (glycogen synthase kinase-3) inhibitors such as SB-517955, SB-4195052, SB-216763, NN-57-05441 and NN-57-05445; RxR ligands such as GW-0791 and AGN-194204; sodium-dependent glucose co-transporter inhibitors such as T-1095; glycogen phosphorylase A inhibitors such as BAY R3401; biguanides such as metformin; alpha-glucosidase inhibitors such as acarbose; GLP-1 (glucagon like peptide-1), GLP-1 analogs such as Exendin-4 and GLP-1 mimetics; modulators of PPARs (peroxisome proliferator-activated receptors), e.g., non-glitazone type PPARγ agonists such as N-(2-benzoylphenyl)-L-tyrosine analogues, e.g. GI-262570, and JTT501; DPPIV (dipeptidyl peptidase IV) inhibitors such as LAF237, MK-0431, saxagliptin and GSK23A; SCD-1 (stearoyl-CoA desaturase-1) inhibitors; DGAT1 and DGAT2 (diacylglycerol acyltransferase 1 and 2) inhibitors; ACC2 (acetyl CoA carboxylase 2) inhibitors; and breakers of AGE (advanced glycation end products);

b) anti-dyslipidemic agents such as 3-hydroxy-3-methyl-glutaryl coenzyme A (HMG-CoA) reductase inhibitors, e.g., lovastatin, pitavastatin, simvastatin, pravastatin, cerivastatin, mevastatin, velostatin, fluvastatin, dalvastatin, atorvastatin, rosuvastatin and rivastatin; HDL increasing compounds such as cholesterol ester transfer protein (CETP) inhibitors, e.g., JTT705; Apo-A1 analogs and mimetics; squalene synthase inhibitors; FxR (farnesoidxreceptor) and LxR (liverxreceptor) ligands; cholestyramine; fibrates; nicotinic acid; and aspirin;

c) anti-obesity agents such as phentermine, leptin, bromocriptine, dexamphetamine, amphetamine, fenfluramine, dexfenfluramine, sibutramine, orlistat, dexfenfluramine, mazindol, phentermine, phendimetrazine, diethylpropion, fluoxetine, bupropion, topiramate, diethylpropion, benzphetamine, phenylpropanolamine, ecopipam, ephedrine, and pseudoephedrine; cholesterol absorption modulators such as ZETIA® and KT6-971; and cannabinoid receptor antagonists such as rimonabant; and d) anti-hypertensive agents, e.g., loop diuretics such as ethacrynic acid, furosemide and torsemide; angiotensin converting enzyme (ACE) inhibitors such as benazepril, captopril, enalapril, fosinopril, lisinopril, moexipril, perinodopril, quinapril, ramipril and trandolapril; inhibitors of the Na-K-ATPase membrane pump such as digoxin; neutralendopeptidase (NEP) inhibitors; ACE/NEP inhibitors such as omapatrilat, sampatrilat and fasidotril; angiotensin II antagonists such as candesartan, eprosartan, irbesartan, losartan, telmisartan and valsartan, in particular valsartan; renin inhibitors such as ditekiren, zankiren, terlakiren, aliskiren, RO 66-1132 and RO-66-1168; β-adrenergic receptor blockers such as acebutolol, atenolol, betaxolol, bisoprolol, metoprolol, nadolol, propranolol, sotalol and timolol; inotropic agents such as digoxin, dobutamine and milrinone; calcium channel blockers such as amlodipine, bepridil, diltiazem, felodipine, nicardipine, nimodipine, nifedipine, nisoldipine and verapamil;

aldosterone receptor antagonists such as eplerenone; and aldosterone synthase inhibitors such as anastrazole and fadrazole.

Other specific anti-diabetic compounds are described by Patel Mona in *Expert Opin Investig Drugs*, 2003, 12(4), 623-633, in the FIGS. 1 to 7, which are herein incorporated by reference. A compound of the present invention may be administered either simultaneously, before or after the other active ingredient, either separately by the same or different route of administration or together in the same pharmaceutical formulation.

The structure of the therapeutic agents identified by code numbers, generic or trade names may be taken from the actual edition of the standard compendium "The Merck Index" or from databases, e.g., Patents International (e.g. IMS World Publications). The corresponding content thereof is hereby incorporated by reference.

Accordingly, the present invention provides pharmaceutical compositions comprising a therapeutically effective amount of a compound of the invention in combination with a therapeutically effective amount of another therapeutic agent, preferably selected from anti-diabetics, hypolipidemic agents, anti-obesity agents or anti-hypertensive agents, most preferably from antidiabetics or anti-obesity agents as described above.

The present invention further relates to pharmaceutical compositions as described above for use as a medicament.

The present invention further relates to use of pharmaceutical compositions or combinations as described above for the preparation of a medicament for the treatment of conditions mediated by PTPase activity, in particular, PTP-1B and TC PTP activity. Such conditions include insulin resistance, glucose intolerance, obesity, diabetes mellitus, hypertension and ischemic diseases of the large and small blood vessels, conditions accompanying type 2 diabetes including dyslipidemia, e.g., hyperlipidemia and hypertriglyceridemia, atherosclerosis, vascular restenosis, irritable bowel syndrome, pancreatitis, adipose cell tumors and carcinomas such as liposarcoma, dyslipidemia, and other disorders where insulin resistance is indicated. In addition, the compounds of the present invention may be employed to treat cancer (such as prostate or breast cancer), osteoporosis, neurodegenerative and infectious diseases, and diseases involving inflammation and the immune system. Such conditions also include insulin resistance, glucose intolerance, type 2 diabetes, renal insufficiency (diabetic and non-diabetic), diabetic nephropathy, glomerulonephritis, glomerular sclerosis, proteinuria of primary renal disease, diabetic retinopathy, obesity, all types of heart failures including acute and chronic congestive heart failure, left ventricular dysfunction and hypertrophic cardiomyopathy, diabetic cardiac myopathy, supraventricular and ventricular arrhythmias, atrial fibrillation and atrial flutter, hypertension, primary and secondary pulmonary hypertension, renal vascular hypertension, dyslipidemia, atherosclerosis, ischemic diseases of the large and small blood vessels, angina pectoris (whether unstable or stable), myocardial infarction and its sequelae, ischemia/reperfusion injury, detrimental vascular remodeling including vascular restenosis, management of other vascular disorders including migraine, peripheral vascular disease and Raynaud's disease, irritable bowel syndrome, pancreatitis, cancer (such as prostate or breast cancer), osteoporosis, multiple sclerosis, stroke, spinal cord injury, neurodegenerative diseases such as Alzheimer's, Parkinson's and polyglutamine disorders such as Huntington's and spinocerebellar ataxia, infectious diseases, and diseases involving inflammation and the immune system and diseases involving muscle degeneration.

Thus, the present invention also relates to a compound of formula (I) for use as a medicament, to the use of a compound of formula (I) for the preparation of a pharmaceutical composition for treatment of conditions mediated by PTPase activity, in particular, PTP-1B and TC PTP activity, and to a pharmaceutical composition for use in conditions mediated by PTPase activity, in particular, PTP-1B and TC PTP activity, comprising a compound of formula (I), or a pharmaceutically acceptable salt thereof, in association with a pharmaceutically acceptable diluent or carrier therefore.

The present invention further provides a method for the treatment of conditions mediated by PTPase activity, in particular, PTP-1B and TC PTP activity, which method comprises administering a therapeutically effective amount of a compound of the present invention.

A unit dosage for a mammal of about 50 to 70 kg may contain between about 1 mg and 1000 mg, advantageously between about 5 mg to 500 mg of the active ingredient. The therapeutically effective dosage of a compound of formula I is dependent on the species of warm-blooded animal (mammal), the body weight, age and individual condition, on the form of administration, and on the compound involved.

In accordance with the foregoing the present invention also provides a therapeutic combination, e.g., a kit, kit of parts, e.g., for use in any method as defined herein, comprising a compound of formula (I), or a pharmaceutically acceptable salt thereof, to be used concomitantly or in sequence with at least one pharmaceutical composition comprising at least another therapeutic agent, preferably selected from anti-diabetic agents, hypolipidemic agents, anti-obesity agents or anti-hypertensive agents. The kit may comprise instructions for its administration.

Similarly, the present invention provides a kit of parts comprising: (i) a pharmaceutical composition of the invention; and (ii) a pharmaceutical composition comprising a compound selected from an anti-diabetic, a hypolipidemic agent, an anti-obesity agent, an anti-hypertensive agent, or a pharmaceutically acceptable salt thereof, in the form of two separate units of the components (i) to (ii).

Likewise, the present invention provides a method as defined above comprising co-administration, e.g., concomitantly or in sequence, of a therapeutically effective amount of a compound of formula (I), or a pharmaceutically acceptable salt thereof, and a second drug substance, said second drug substance being an anti-diabetic, a hypolipidemic agent, an anti-obesity agent or an anti-hypertensive agent, e.g., as indicated above.

Preferably, a compound of the invention is administered to a mammal in need thereof.

Preferably, a compound of the invention is used for the treatment of a disease which responds to modulation of PTPase activity, in particular, PTP-1B and TC PTP activity.

Preferably, the condition associated with PTPase activity, in particular, PTP-1B and TC PTP activity, is selected from insulin resistance, glucose intolerance, type 2 diabetes, renal insufficiency (diabetic and non-diabetic), diabetic nephropathy, glomerulonephritis, glomerular sclerosis, proteinuria of primary renal disease, diabetic retinopathy, obesity, all types of heart failures including acute and chronic congestive heart failure, left ventricular dysfunction and hypertrophic cardiomyopathy, diabetic cardiac myopathy, supraventricular and ventricular arrhythmias, atrial fibrillation and atrial flutter, hypertension, primary and secondary pulmonary hypertension, renal vascular hypertension, dyslipidemia, atherosclerosis, ischemic diseases of the large and small blood vessels, angina pectoris (whether unstable or stable), myocardial infarction and its sequelae, ischemia/reperfusion injury, detrimental vascular remodeling including vascular restenosis, management of other vascular disorders including migraine, peripheral vascular disease and Raynaud's disease, irritable bowel syndrome, pancreatitis, cancer (such as prostate or breast cancer), osteoporosis, multiple sclerosis, stroke, spinal cord injury, neurodegenerative diseases such as Alzheimer's, Parkinson's and polyglutamine disorders such as Huntington's and spinocerebellar ataxia, infectious diseases, and diseases involving inflammation and the immune system and diseases involving muscle degeneration.

Preferably, the condition associated with PTPase activity, in particular, PTP-1B and TC PTP activity, is selected from insulin resistance, glucose intolerance, obesity, diabetes mellitus, hypertension and ischemic diseases of the large and small blood vessels, conditions accompanying type 2 diabetes including dyslipidemia, e.g., hyperlipidemia and hypertriglyceridemia, atherosclerosis, vascular restenosis, irritable bowel syndrome, pancreatitis, adipose cell tumors and carcinomas such as liposarcoma, dyslipidemia, and other disorders where insulin resistance is indicated. In addition, the compounds of the present invention may be employed to treat cancer (such as prostate or breast cancer), osteoporosis, neurodegenerative and infectious diseases, and diseases involving inflammation and the immune system.

Finally, the present invention provides a method or use which comprises administering a compound of formula (I) in combination with a therapeutically effective amount of an anti-diabetic agent, a hypolipidemic agent, an anti-obesity agent or an anti-hypertensive agent.

Ultimately, the present invention provides a method or use which comprises administering a compound of formula (I) in the form of a pharmaceutical composition as described herein.

As used throughout the specification and in the claims, the term "treatment" embraces all the different forms or modes of treatment as known to those of the pertinent art and in particular includes preventive, curative, delay of progression and palliative treatment.

The above-cited properties are demonstrable in vitro and in vivo tests, using advantageously mammals, e.g., mice, rats, dogs, monkeys or isolated organs, tissues and preparations thereof. Said compounds can be applied in vitro in the form of solutions, e.g. preferably aqueous solutions, and in vivo either enterally, parenterally, advantageously intravenously, e.g. as a suspension or in aqueous solution. The dosage in vitro may range between about $10^{-3}$ molar and $10^{-11}$ molar concentrations or between about $10^{-3}$ molar and $10^{-10}$ molar concentrations. A therapeutically effective amount in vivo may range depending on the route of administration, between about 0.1 and 500 mg/kg or between about 1 and 500 mg/kg, preferably between about 5 and 100 mg/kg.

The activity of a compound according to the invention may be assessed by the following methods or by following methods well described in the art (e.g. Peters G. et al. *J. Biol. Chem,* 2000, 275, 18201-09).

For example, the PTP-1B inhibitory activity in vitro may be determined as follows:

Assessment of human PTP-1B (hPTP-1B) activity in the presence of various agents is determined by measuring the amount of inorganic phosphate released from a phosphopeptide substrate using a 96-well microtiter plate format. The assay (100 µL) is performed in an assay buffer comprised of 50 mM TRIS (pH 7.5), 50 mM NaCl, 3 mM DTT at ambient temperature. The assay is typically performed in the presence of 0.4% dimethyl sulfoxide (DMSO). However, concentrations as high as 10% are used with certain poorly soluble compounds. A typical reaction is initiated by the addition of 0.4 pmoles of hPTP-1B (amino acids 1-411) to wells containing assay buffer, 3 nmoles of the synthetic phosphopeptide substrate (GNGDpYMPMSPKS), and the test compound. After 10 min, 180 µL malachite green reagent (0.88 mM malachite green, 8.2 mM ammonium molybdate, aqueous 1 N HCl, and 0.01% Triton X-100) is added to terminate the reaction. Inorganic phosphate, a product of the enzyme reaction, is quantitated after 15 min as the green color resulting from complexing with the Malichite reagent and is determined as an $A_{620}$ using a Molecular Devices (Sunnyvale, Calif.) SpectraMAX Plus spectrophotometer. Test compounds are solubilized in 100% DMSO (Sigma, D-8779) and diluted in DMSO. Activity is defined as the net change in absorbance resulting from the activity of the uninhibited $hPTP-1B_{[1-411]}$ minus that of a tube with acid-inactivated $hPTP-1B_{[1-411]}$.

The $hPTP-1B_{[1-411]}$ is cloned by PCR from a human hippocampal cDNA library (Clonetech) and inserted into a pET 19-b vector (Novagen) at the Nco1 restriction site. *E. coli* strain BL21 (DE3) is transformed with this clone and stored as a stock culture in 20% glycerol at −80° C. For enzyme production, a stock culture is inoculated into Lb/Amp and grown at 37° C. Expression of PTP-1B is initiated by induction with 1 mM IPTG after the culture had reached an $OD_{600}$=0.6. After 4 h, the bacterial pellet is collected by centrifugation. Cells are resuspended in 70 mL lysis buffer (50 mM Tris, 100 mM NaCl, 5 mM DTT, 0.1% Triton X-100, pH7.6), incubated on ice for 30 min then sonicated (4×10 sec bursts at full power). The lysate is centrifuged at 100,000×g for 60 min and the supernatant is buffer exchanged and purified on a cation exchange POROS 20SP column followed by an anion exchange Source 30Q (Pharmacia) column, using linear NaCl gradient elutions. Enzyme is pooled, adjusted to 1 mg/mL and frozen at −80° C.

Alternatively, the assessment of human PTP-1B activity in the presence of various agents may be determined by measuring the hydrolysis products of known competing substrates. For example, cleavage of substrate para-nitrophenylphosphate (pNPP) results in the release of the yellow-colored para-nitrophenol (pNP) which can be monitored in real time using a spectrophotometer. Likewise, the hydrolysis of the fluorogenic substrate 6,8-difluoro-4-methylumbelliferyl phosphate ammonium salt (DiFMUP) results in the release of the fluorescent DiFMU which can be readily followed in a continuous mode with a fluorescence reader (Anal. Biochem. 273, 41, 1999; Anal. Biochem. 338, 32, 2005):

pNPP Assay

Compounds were incubated with 1 nM recombinant human $PTP-1B_{[1-298]}$ or $PTP-1B_{[1-322]}$ in buffer (50 mM Hepes, pH 7.0, 50 mM KCl, 1 mM EDTA, 3 mM DTT, 0.05% NP-40 for 5 min at room temperature. The reaction is initiated by the addition of pNPP (2 mM final concentration) and run for 120 min at room temperature. Reactions are quenched with 5 N NaOH. Absorbance at 405 nm is measured using any standard 384 well plate reader.

DiFMUP Assay

Compounds are incubated with 1 nM recombinant human $PTP-1B_{[1-298]}$ or $PTP-1B_{[1-322]}$ in buffer (50 mM Hepes, pH 7.0, 50 mM KCl, 1 mM EDTA, 3 mM DTT, 0.05% NP-40 (or 0.001% BSA) for 5 min at room temperature. The reaction is initiated by the addition of DiFMUP (6 µM final concentration) and run kinetically on fluorescence plate reader at 355 nm excitation and 460 nm emission wavelengths. Reaction rates over 15 min are used to calculate inhibition.

PTP-1B$_{[1-298]}$ is expressed in *E. coli* BL21(DE3) containing plasmids constructed using pET19b vectors (Novagen). The bacteria is grown in minimal media using an "On Demand" Fed-batch strategy. Typically, a 5.5 liter fermentation is initiated in Fed-batch mode and grown overnight unattended at 37° C. Optical densities varied between 20-24 OD$_{600}$ and the cultures are induced at 30° C. with IPTG to a final concentration of 0.5 mM. The bacterial cells are harvested 8 hours later and yield 200-350 gm (wet weight). The cells are frozen as pellets and stored at −80° C. until use. All steps are performed at 4° C. unless noted. Cells (~15 g) are thawed briefly at 37° C. and resuspended in 50 mL of lysis buffer containing 50 mM Tris-HCl, 150 mM NaCl, 5 mM DTT, pH 8.0 containing one tablet of Complete (EDTA-free) protease cocktail (Boehringer Mannheim), 100 μM PMSF and 100 μg/mL DNase I. The cells are lysed by sonication (4×10 second burst, full power) using a Virsonic 60 (Virtus). The pellet is collected at 35,000×g, resuspended in 25 mL of lysis buffer using a Polytron and collected as before. The two supernatants are combined and centrifuged for 30 min at 100,000×g. The soluble lysate could be stored at this stage at −80° C. or used for further purification. Diafiltration using a 10 kD MWCO membrane is used to buffer exchange the protein and reduce the NaCl concentration prior to cation exchange chromatography. Diafiltration buffer contained 50 mM MES, 75 mM NaCl, 5 mM DTT, pH 6.5. Soluble supernatant is then loaded onto a POROS 20 SP (1×10 cm) column equilibrated with cation exchange buffer (50 mM MES and 75 mM NaCl, pH 6.5) at a rate of 20 mL/min. An analytical column (4.6×100 mm) is run in a similar fashion except the flow rate was reduced to 10 mL/min. Protein is eluted from the column using a linear salt gradient (75-500 mM NaCl in 25 CV). Fractions containing PTP-1B$_{[1-298]}$ are identified and pooled according to SDS-PAGE analyses. Final purification is performed using Sephacryl S-100 HR (Pharmacia). The column (2.6×35 cm) is equilibrated with 50 mM HEPES, 100 mM NaCl, 3 mM DTT, pH 7.5 and run at a flow rate of 2 mL/min. The final protein is pooled and concentrated to ~5 mg/mL using an Ultrafree-15 concentrator (Millipore) with a MWCO 10,000. The concentrated protein is stored at −80° C. until use.

Competitive binding to the active site of the enzyme may be determined as follows:

Ligand binding is detected by acquiring $^1$H-$^{15}$N HSQC spectra on 250 μL of 0.15 mM PTP-1B$_{[1-298]}$ in the presence and absence of added compound (1-2 mM). The binding is determined by the observation of $^{15}$N— or $^1$H-amide chemical shift changes in two dimensional HSQC spectra upon the addition of a compound to $^{15}$N-label protein. Because of the $^{15}$N spectral editing, no signal from the ligand is observed, only protein signals. Thus, binding can be detected at high compound concentrations. Compounds which caused a pattern of chemical shift changes similar to the changes seen with known active site binders are considered positive.

All proteins are expressed in *E. coli* BL21 (DE3) containing plasmids constructed using pET19b vectors (Novagen). Uniformly $^{15}$N-labeled PTP-1B$_{1-298}$ is produced by growth of bacteria on minimal media containing $^{15}$N-labeled ammonium chloride. All purification steps are performed at 4° C. Cells (~15 g) are thawed briefly at 37° C. and resuspended in 50 mL of lysis buffer containing 50 mM Tris-HCl, 150 mM NaCl, 5 mM DTT, pH 8.0 containing one tablet of Complete (EDTA-free) protease cocktail (Boehringer Mannheim), 100 μM PMSF and 100 μg/mL DNase I. The cells are lysed by sonication. The pellet is collected at 35,000×g, resuspended in 25 mL of lysis buffer using a Polytron and collected as before. The two supernatants are combined and centrifuged for 30 min at 100,000×g. Diafiltration using a 10 kD MWCO membrane is used to buffer exchange the protein and reduce the NaCl concentration prior to cation exchange chromatography. Diafiltration buffer contained 50 mM MES, 75 mM NaCl, 5 mM DTT, pH 6.5. Soluble supernatant is then loaded onto a POROS 20 SP (1×10 cm) column equilibrated with cation exchange buffer (50 mM MES and 75 mM NaCl, pH 6.5) at a rate of 20 mL/min. Protein is eluted from the column using a linear salt gradient (75-500 mM NaCl in 25 CV). Fractions containing PTP-1B's are identified and pooled according to SDS-PAGE analyses. PTP-1B$_{1-298}$ is further purified by anion exchange chromatography using a POROS 20 HQ column (1×10 cm). The pool from cation exchange chromatography is concentrated and buffer exchanged in 50 mM Tris-HCl, pH 7.5 containing 75 mM NaCl and 5 mM DTT. Protein is loaded onto column at 20 mL/min and eluted using a linear NaCl gradient (75-500 mM in 25 CV). Final purification is performed using Sephacryl S-100 HR (Pharmacia)(50 mM HEPES, 100 mM NaCl, 3 mM DTT, pH 7.5). The NMR samples are composed of uniformly $^{15}$N-labeled PTP-1B$_{1-298}$ (0.15 mM) and inhibitor (1-2 mM) in a 10% D$_2$O/90% H$_2$O Bis-Tris-d$_{19}$ buffer (50 mM, pH=6.5) solution containing NaCl (50 mM), DL-1,4-Dithiothreitol-d$_{10}$ (5 mM) and Sodium azide (0.02%).

The $^1$H-$^{15}$N HSQC NMR spectra are recorded at 20° C., on Bruker DRX500 or DMX600 NMR spectrometers. In all NMR experiments, pulsed field gradients are applied to afford the suppression of solvent signal. Quadrature detection in the indirectly detected dimensions is accomplished by using the States-TPPI method. The data are processed using Bruker software and analyzed using NMRCompass software (MSI) on Silicon Graphics computers.

The glucose and insulin lowering activity in vivo may be evaluated as follows:

Adult male C57BL ob/ob mice (Jackson Lab, Bar Harbor, Me.) at the age of 11 weeks are housed six per cage in a reversed light cycle room (light on from 6:00 p.m. to 6:00 a.m.) and given access to Purina rodent chow and water ad libitum. On day 1 tail blood samples are taken at 8:00 am and plasma glucose levels are determined. The animals are randomly assigned to the control and compound groups. The means of plasma glucose values of the groups are matched. Animals are then orally dosed with vehicle (0.5% carboxymethyl-cellulose with 0.2% Tween-80) or compounds (at 30 mg/kg) in vehicle. The mice are dosed daily for a total of 3 days. On day 4 basal blood samples are taken. The plasma samples are analyzed for glucose concentrations using a YSI2700 Dual Channel Biochemistry Analyzer (Yellow Springs Instrument Co., Yellow Springs, Ohio) and insulin concentrations using an ELISA assay.

The following Examples are intended to illustrate the invention and are not to be construed as being limitations thereon. Temperatures are given in degrees Centigrade (° C.). If not mentioned otherwise, all evaporations are performed under reduced pressure, preferably between about 15 and 100 mmHg (=20-133 mbar). The structure of final products, intermediates and starting materials is confirmed by standard analytical methods, e.g. microanalysis, melting point (mp) and spectroscopic characteristics (e.g. MS, IR, NMR). In general, abbreviations used are those conventional in the art.

HPLC Methods

Method A: 4.6 mm×5 cm C-8 reverse phase column, 3 μM particle size running a gradient of 10-90% MeCN/water (5

EXAMPLE 1

Methanesulfonic acid 2-[3-fluoro-5-hydroxy-4-(1,1,4-trioxo-1,2,5-thiadiazolidin-2-yl)-benzyl]-4-methylphenyl ester

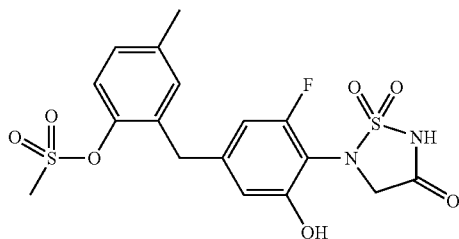

A. 2-Methanesulfonyloxy-5-methylbenzoic acid methyl ester

To a ice cooled suspension of sodium hydride (60%, 1.3 g, 78.3 mmol) in THF (100 mL) is added a solution of 2-hydroxy-5-methylbenzoic acid methyl ester (10 g, 60 mmol) in THF (20 mL) and it is stirred at 0° C. Then a solution of methanesulfonyl chloride (8.2 g, 72 mmol) in THF (20 mL) is added dropwise. The reaction mixture is stirred at RT for 18 h. Then the reaction mixture is cooled in an ice bath and slowly ice is added to quench the reaction. EtOAc is used to extract. Brine is added to the aqueous phase and re-extracted with EtOAc. The combined organic phase is washed with water, brine, dried over NaSO$_4$ and MgSO$_4$, and concentrated to give the title compound as an oil. It is used directly in the next step.

B. Methanesulfonic acid 2-hydroxymethyl-5-methylphenyl ester

To a solution of 2-methanesulfonyloxy-5-methylbenzoic acid methyl ester (15 g, 61.4 mmol) in THF (30 mL) at 0° C. is added portionwise LiBH$_4$ (4.0 g, 184 mmol) and the mixture is stirred for 15 min. Then MeOH (8 mL, 196 mmol) is added dropwise over 30 min. The mixture is stirred under ice cooling for 30 min, then at RT for 18 h. EtOAc is added followed by ice and water. The mixture is acidified slowly with 1N HCl solution and organic phase is separated. The aqueous phase is extracted with EtOAc. The organic phases are combined, and washed with 1N HCl solution, and brine. It is then dried over Na$_2$SO$_4$ and MgSO$_4$, and concentrated to give the title compound as an oil.

C. Methanesulfonic acid 2-iodomethyl-5-methylphenyl ester

To a solution of imidazole (4.5 g, 66.6 mmol) and PPh$_3$ (17.4 g, 66.6 mmol) in DCM (180 mL) is slowly added over a period of 10 min of I$_2$ (16.9 g, 66.6 mmol) and it is stirred at RT for 30 min. Then a solution of methanesulfonic acid 2-hydroxymethyl-5-methylphenyl ester (12.0 g, 55.5 mmol) in DCM (40 mL) is added drop wise and it is stirred at RT for 1 h. The reaction mixture is concentrated to about 70 mL. It is then filtered and washed with DCM. The filtrate is concentrated and purified to give the title compound as a solid.

D. 1-Benzyloxy-3-fluoro-2-nitrobenzene

A mixture of 1,3-difluoro-2-nitrobenzene (1.0 g, 6.29 mmol), benzyl alcohol (0.81 mL, 7.86 mmol) and potassium carbonate (1.74 g, 12.6 mmol) in DMF (5 mL) is heated at 60° C. for 18 h. The reaction mixture is poured into EtOAc, and washed with water and brine. The organic phase is concentrated and purified to give the title compound: $^1$H NMR (CDCl$_3$) $\delta$7.36 (m, 6H), 6.83 (m, 2H), 5.20 (s, 2H).

E. 2-Benzyloxy-6-fluorophenylamine

A mixture of 1-benzyloxy-3-fluoro-2-nitrobenzene (1.32 g, 5.34 mmol), SnCl$_2$ (4.96 g, 26.2 mmol), and 1N HCl (5.5 mL, 5.5 mmol) in EtOH (25 mL) is refluxed for 18 h. The mixture is concentrated and stirred with EtOAc and 1N NaOH solution. Solid NaOH is added until strongly basic. The precipitate is removed by filtration, and the organic phase is separated. It is then dried and concentrated. The residue is purified to give the title compound: MS (M+H)$^+$=218.

F. 2-Benzyloxy-4-bromo-6-fluorophenylamine

To a solution of 2-benzyloxy-6-fluorophenylamine (7.29 g, 33.6 mmol) in MeOH/HOAc (3:1 v/v, 30 mL) at 0° C. is added bromine (2.2 mL, 47 mmol) in MeOH/HOAc (3:1 v/v, 4 mL) drop wise. After it is stirred for 4 h, the reaction is completed by LC/MS. The reaction mixture is concentrated, and the residue is stirred with EtOAc and 1N NaOH to dissolve solid. Additional base is added to make the aqueous alkaline, and then EtOAc layer is separated. The organic phase is washed with brine, dried and filtered. The concentrated residue is purified to give the title compound: $^1$H NMR (CDCl$_3$) $\delta$7.39 (m, 5H), 6.86 (dd, 1H, J=9.8, 2.0 Hz), 6.81 (m, 1H), 5.05 (s, 2H), 3.77 (br s, 2H); MS (M+H)$^+$=296, 298.

G. (2-Benzyloxy-4-bromo-6-fluorophenylamino)-acetic acid methyl ester

To a mixture of 2.6 g (8.78 mmol) of 2-benzyloxy-4-bromo-6-fluoroaniline and 3.03 g (21.96 mmol) of potassium carbonate in 20 mL DMF in an oil bath at 60° C. is added 1.48 g (9.67 mmole) of methyl bromoacetate. The mixture is stirred at 60° C. for 2 h. HPLC analysis indicated that the reaction is 38% complete. Additional methyl bromoacetate equal to the molar amount of unreacted starting material is added and the mixture is stirred at 60° C. for 2 h. This process is repeated until the starting material is nearly consumed. The mixture is allowed to cool then is poured into water. The mixture is extracted with ethyl acetate and the organic phase is washed 3× with water. The organic solution is dried over sodium sulfate and the solvent is removed under reduced pressure. The residual dark oil is purified by flash chromatography using methylene chloride to elute the product as a dark oil. This is used directly in the next step.

H. N-(t-Butoxycarbonylsulfamoyl)-N-(2-benzyloxy-4-bromo-6-fluorophenyl)glycine methyl ester To a solution of 1.25 g (8.83 mmol) of chlorosulfonyl isocyanate in 15 mL of methylene chloride is added dropwise a solution of 650 mg (8.83 mmol) of t-butanol in 5 mL methylene chloride. The solution is stirred at room temperature for 45 min. then a solution of 2.30 g (6.25 mmol) of (2-benzyloxy-4-bromo-6-fluorophenylamino)-acetic acid methyl ester and 1.25 g (12.4 mmol) of triethylamine in 10 mL methylene chloride is added dropwise. The mixture is stirred at room temperature for 3 h then is washed with water. The organic phase is dried over sodium sulfate and the solvent is removed under reduced pressure. The residual oil is purified by flash chromatography using 15% ethyl acetate/methylene chloride to elute the product as an oil: $^1$H NMR (CDCl$_3$): δ 7.46-7.33 (m, 6H), 6.98 (d, J=9.1 Hz, 1H), 6.95 (s, 1H), 5.15 (s, 2H), 4.68 (d, J=18 Hz, 1H), 4.41 (d, J=18 Hz, 1H), 3.64 (s, 3H), 1.45 (s, 9H); MS (M−H)$^-$=547.

I. N-Sulfamoyl-N-(2-benzyloxy-4-bromo-6-fluorophenyl)glycine methyl ester

To a solution of 1.25 g (2.28 mmol) of N-(t-butoxycarbonylsulfamoyl)-N-(2-benzyloxy-4-bromo-6-fluorophenyl) glycine methyl ester in 6 mL of methylene chloride is added 6 mL of TFA. The solution is stirred at room temperature for 20 min. then the solvent is removed under reduced pressure. The residual oil is purified by flash chromatography using 15% ethyl acetate in methylene chloride to elute the product as an oil: $^1$H NMR (CDCl$_3$) δ 7.48-7.36 (m, 5H), 7.02-6.98 (m, 2H), 5.10 (d, J=4.30 Hz, 2H), 4.94 (s, 2H), 4.34 (q, 2H), 3.70 (s, 3H); MS (M−H)$^-$=447.

J. 5-(2-Benzyloxy-4-bromo-6-fluorophenyl)-1,1-dioxo-1,2,6-thiadiazolidin-3-one potassium salt To a solution of 860 mg (1.92 mmol) of N-sulfamoyl-N-(2-benzyloxy-4-bromo-6-fluorophenyl)glycine methyl ester in 15 mL of THF is added dropwise 2.11 mL (2.1 mmol) of potassium tert-butoxide (1.0N in THF). The solution is stirred at RT for 4 h then the solvent is removed under reduced pressure. The residual gum is dissolved in water and lyophilized to give the product as a beige amorphous solid: mp=90-100° C.; $^1$H NMR (DMSO-d$_6$) δ7.49 (d, J=6.8 Hz, 2H), 7.39-7.29 (m, 3H), 7.17 (m, 2H), 5.19 (s, 2H), 3.94 (s, 2H); MS (M−H)$^-$=415.

K. 5-(2-Benzyloxy-6-fluoro-4-iodophenyl)-1,1-dioxo-1,2,5-thiadiazolidin-3-one A mixture of 5-(2-benzyloxy-4-bromo-6-fluorophenyl)-1,1-dioxo-1,2,5-thiadiazolidin-3-one (1.0 g, 2.21 mmol), NaI (1.18 g, 7.87 mmol), CuI (91 mg, 0.48 mmol) and (1R,2R)—N,N'-dimethylcyclohexane-1,2-diamine (136 mg, 0.96 mmol) in dioxane (15.5 mL) is heated at 140° C. for 1.5 h in a microwave. The reaction mixture is filtered through Celite and washed with additional dioxane. It is then concentrated to a smaller volume and used directly in the next step: MS (M−H)$^-$=461.

L. 5-(2-Benzyloxy-6-fluoro-4-iodophenyl)-2-benzyloxymethyl-1,1-dioxo-1,2,5-thiadiazolidin-3-one To the above solution is added chloromethoxymethylbenzene (1.5 equiv.) and it is stirred at RT for 2.5 h. The solvent is removed, and EtOAc and water is added. The organic layer is separated, and aqueous layer is extracted one more time with EtOAc. The combine organic layer is washed with water and brine, dried and concentrated. The residue is purified to give the title compound: $^1$H NMR (CDCl$_3$) δ7.33 (m, 10H), 7.23 (m, 1H), 7.21 (m, 1H), 5.07 (s, 2H), 5.01 (s, 2H), 4.54 (s, 2H), 4.35 (s, 2H); MS (M+18)$^+$=600.

M. Methanesulfonic acid 2-[3-benzyloxy-4-(5-benzyloxymethyl-1,1,4-trioxo-1,2,5-thiadiazolidin-2-yl)-5-fluorobenzyl]-4-methylphenyl ester Zinc dust (200 mg, 3.08 mmol) is added to a flask and heated with a heat gun under high vacuum to remove moisture. DMF (1.0 mL, freshly distilled) is added under argon. 1,2-Dibromoethane (0.02 mL) is added and heated with heat gun until bubbling is observed. After it is cooled to RT, TMSCl (0.02 mL) is added and the mixture is stirred at RT for 20 min. Then a solution of methanesulfonic acid 2-iodomethyl-5-methylphenyl ester (224 mg, 0.688 mmol) in DMF (0.6 mL, freshly distilled) is added and the mixture is heated at 40° C. for 45 min. Then it is cooled to RT. Pd$_2$(dba)$_3$ (20 mg, 0.02 mmol), P(o-tolyl)$_3$ (28.4 mg, 0.10 mmol) is added followed by a solution of 5-(2-benzyloxy-6-fluoro-4-iodophenyl)-2-benzyloxymethyl-1,1-dioxo-1,2,5-thiadiazolidin-3-one (200 mg, 0.344 mmol) in DMF (1.4 mL, freshly distilled). The mixture is stirred at RT for 2 h. ETOAc is added and it is filtered through Celite. The filtrate is then washed with 1N HCl solution, water and brine. It is then dried and concentrated. The residue is purified to give the title compound.

N. Methanesulfonic acid 2-[3-fluoro-5-hydroxy-4-(1,1,4-trioxo-1,2,5-thiadiazolidin-2-yl)-benzyl]-4-methylphenyl ester To a solution of methanesulfonic acid 2-[3-benzyloxy-4-(5-benzyloxymethyl-1,1,4-trioxo-1,2,5-thiadiazolidin-2-yl)-5-fluorobenzyl]-4-methylphenyl ester (85 mg) in EtOH (3 mL) and EtOAc (6 mL) is added 5% Pd/C (75 mg) and the mixture is hydrogenated at 1 atm for 18 h. The catalyst is filtered and washed with EtOH (3×). Solvent is evaporated to near dryness before water and acetonitile is added to form a solution. It is then lyophilized to give the title compound: MS (M−H)$^-$=443.

EXAMPLE 2

Methanesulfonic acid 2-[3-fluoro-5-hydroxy-4-(1,1,4-trioxo-1,2,5-thiadiazolidin-2-yl)-benzyl]-5-methylphenyl ester

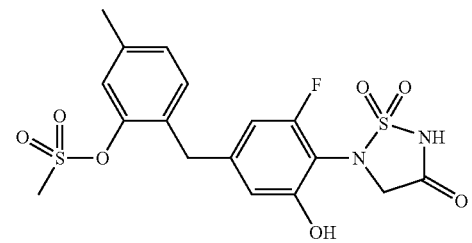

A. Methanesulfonic acid 2-hydroxymethyl-5-methylphenyl ester

The title compound is prepared analogously to Example 1, Steps A and B, starting from 2-hydroxy-4-methylbenzoic acid methyl ester.

B. Methanesulfonic acid 2-bromomethyl-5-methylphenyl ester

To a solution of methanesulfonic acid 2-hydroxymethyl-5-methylphenyl ester (864 mg, 4 mmol) in DCM (45 mL) is added CBr₄ (2.0 g, 6 mmol) and PPh₃ (1.57 g, 6 mmol). The mixture is stirred at RT for 6 h. The solvent is removed and the residue is purified to give the title compound as a solid.

C. 5-[2-Fluoro-6-hydroxy-4-(4,4,5,5-tetramethyl-1,3,2-dioxaborolan-2-yl)-phenyl]-1,1-dioxo-1,2,5-thiadiazolidin-3-one A mixture of 5-(2-benzyloxy-4-bromo-6-fluorophenyl)-1,1-dioxo-1,2,5-thiadiazolidin-3-one potassium salt (453 mg, 1 mmol), 4,4,5,5,4',4',5',5'-octamethyl-2,2'bi[1,3,2-dioxaborolanyl] (508 mg, 2 mmol), PdCl₂(dppt) (82 mg, 0.1 mmol), KOAc (294 mg, 3 mmol) in DME (2 mL) is heated at 120° C. for 20 min. in a microwave. The solvent is removed, and ice with NaHCO₃ (5%, 50 mL) is added. It is washed with Et₂O (50 mL×2). The aqueous layer is acidified with concentrated HCl, and extracted with EtOAc (50 mL). It is then dried over MgSO₄, decolorized with charcoal and concentrated to give the title compound: MS (M–H)⁻=461.

D. Methanesulfonic acid 2-[3-benzyloxy-5-fluoro-4-(1,1,4-trioxo-1,2,5-thiadiazolidin-2-yl)-benzyl]-5-methylphenyl ester A mixture of 5-[2-fluoro-6-hydroxy-4-(4,4,5,5-tetramethyl-1,3,2-dioxaborolan-2-yl)-phenyl]-1,1-dioxo-1,2,5-thiadiazolidin-3-one (150 mg, 0.325 mmol) and Pd(PPh₃)₄ (38 mg, 0.0325 mmol) in DME (2 mL) is heated at 60° C. under argon for 1 h. Then methanesulfonic acid 2-bromomethyl-5-methylphenyl ester (181 mg, 0.65 mmol) and Na₂CO₃ (2N solution, 0.81 mL) is added. The mixture is heated at 120° C. in a microwave for 20 min. 1N HCl is added and the reaction mixture is extracted with EtOAc. The organic layer is washed with brine, dried over MgSO₄ and filtered. The filtrate is concentrated to give the title compound and it is used directly in the next step: MS (M–H)⁻=533.

E. Methanesulfonic acid 2-[3-fluoro-5-hydroxy-4-(1,1,4-trioxo-1,2,5-thiadiazolidin-2-yl)-benzyl]-5-methylphenyl ester potassium salt The title compound is prepared analogously to Example 1, Step N: ¹H NMR (CDCl₃) δ2.30 (s, 3H), 3.44 (s, 3h), 3.81 (s, 2H), 3.92 (s, 2H), 6.24-6.33 (m, 2H), 7.09-7.20 (m, 3H); MS (M–H)⁻=443.

EXAMPLE 3

Methanesulfonic acid 2-[3-fluoro-5-hydroxy-4-(1,1,4-trioxo-1,2,5-thiadiazolidin-2-yl)-benzyl]-6-methylphenyl ester

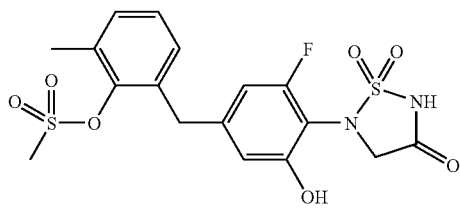

The title compound is prepared analogously to Example 1, Steps A to N, from 2-hydroxy-3-methylbenzoic acid methyl ester.

EXAMPLE 4

Methanesulfonic acid 2-[3-fluoro-5-hydroxy-4-(1,1,4-trioxo-1,2,5-thiadiazolidin-2-yl)-benzyl]-phenyl ester

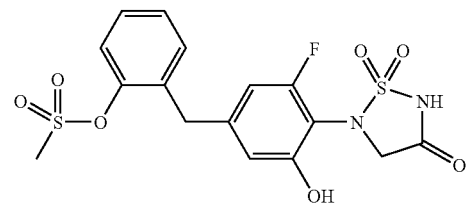

The title compound is prepared analogously to Example 1, Steps A to N, from 2-hydroxybenzoic acid methyl ester: MS (M–H)⁻=429.

EXAMPLE 5

N-{2-[3-Fluoro-5-hydroxy-4-(1,1,4-trioxo-1,2,5-thiadiazolidin-2-yl)-benzyl]-5-methylphenyl}-methanesulfonamide

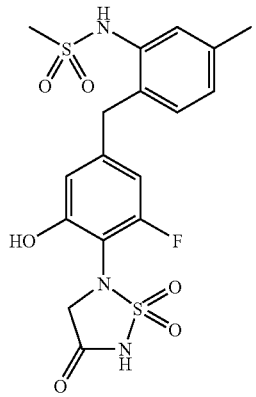

A. (2-Amino-4-methylphenyl)-methanol

To a solution of 2-amino-4-methylbenzoic acid (1.0 g, 6.62 mmol) in THF (10 mL) is added drop wise BH₃ THF (1.0 M, 16.6 mL, 16.6 mmol) and the mixture is stirred at RT for 3 days. Excess BH₃ is quenched with 1N HCl at 0° C. The solvent is evaporated to obtain a white solid. The solid is washed with water, and then hexane to remove the water. The solid is then dried in an oven to obtain the title compound).

B. (2-Hydroxymethyl-5-methylphenyl)-carbamic acid tert-butyl ester

To a solution of (2-amino-4-methylphenyl)-methanol (3.2 g, 23.4 mmol) in THF (40 mL) is added di-tert-butyl dicarbonate (6.54 g, 28.0 mmol) and the solution is stirred at 60° C. for 5 h. The solvent is evaporated, and water is added. It is then extracted with EtOAc, washed with water, dried with MgSO$_4$ and concentrated. The residue is purified to give the title compound.

C. (2-Iodomethyl-5-methylphenyl)-carbamic acid tert-butyl ester

The title compound is prepared analogously to Example 1, Step C, from (2-hydroxymethyl-5-methylphenyl)-carbamic acid tert-butyl ester.

D. {2-[3-Benzyloxy-4-(5-benzyloxymethyl-1,1,4-trioxo-1,2,5-thiadiazolidin-2-yl)-5-fluorobenzyl]-5-methylphenyl}-carbamic acid tert-butyl ester The title compound is prepared analogously to Example 1, Step M, with (2-iodomethyl-5-methylphenyl)-carbamic acid tert-butyl ester and 5-(2-benzyloxy-6-fluoro-4-iodophenyl)-2-benzyloxymethyl-1,1-dioxo-1,2,5-thiadiazolidin-3-one.

E. 5-[4-(2-Amino-4-methylbenzyl)-2-benzyloxy-6-fluorophenyl]-2-benzyloxymethyl-1,1-dioxo-1,2,5-thiadiazolidin-3-one The title compound is prepared analogously to Example 1, Step I.

F. N-{2-[3-Benzyloxy-4-(5-benzyloxymethyl-1,1,4-trioxo-1,2,5-thiadiazolidin-2-yl)-5-fluorobenzyl]-5-methylphenyl}-methanesulfonamide To a solution of 5-[4-(2-amino-4-methylbenzyl)-2-benzyloxy-6-fluorophenyl]-2-benzyloxymethyl-1,1-dioxo-1,2,5-thiadiazolidin-3-one (240 mg, 0.42 mmol) in pyridine (5 mL) is added methanesulfonyl chloride (0.064 mL, 0.84 mmol) and the solution is stirred at RT for 2 h. The mixture is then diluted in EtOAc, and it is washed with 1N HCl, brine and water. The organic layer is dried with MgSO$_4$, and concentrated. The residue is purified to give the title compound.

G. N-{2-[3-Fluoro-5-hydroxy-4-(1,1,4-trioxo-1,2,5-thiadiazolidin-2-yl)-benzyl]-5-methylphenyl}-methanesulfonamide The title compound is prepared analogously to Example 1, Step N: MS (M−H)$^-$=442.

EXAMPLE 6

N-{2-[3-Fluoro-5-hydroxy-4-(1,1,4-trioxo-1,2,5-thiadiazolidin-2-yl)-benzyl]-4-methylphenyl}-methanesulfonamide

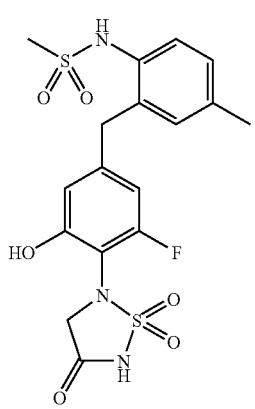

The title compound is prepared analogously to Example 5, Steps A to G, starting from 2-amino-5-methylbenzoic acid: MS (M−H)$^-$=442.

EXAMPLE 7

N-{2-[3-Fluoro-5-hydroxy-4-(1,1,4-trioxo-1,2,5-thiadiazolidin-2-yl)-benzyl]-phenyl}-methanesulfonamide

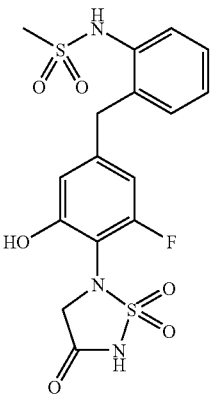

The title compound is prepared analogously to Example 5, Steps B to G, starting from 2-aminophenylmethanol: MS (M−H)$^-$=428.

EXAMPLE 8

5-(4-Benzyl-2-fluoro-6-hydroxy-phenyl)-1,1-dioxo-1,2,5-thiadiazolidin-3-one

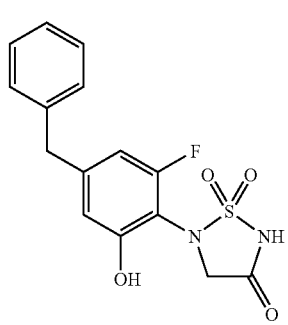

A. 5-(4-Benzyl-2-benzyloxy-6-fluorophenyl)-1,1-dioxo-1,2,5-thiadiazolidin-3-one potassium salt To a microwave vial is added 90 mg (0.199 mmole) of 5-(2-benzyloxy-4-bromo-6-fluorophenyl)-1,1-dioxo-1,2,5-thiadiazolidin-3-one potassium salt (intermediate from 1) and 60 mg of polystyrene-tetrakis(triphenylphosphine)palladium (0) (0.1 mmol/g) followed by 4.5 mL DME. To this is added 84 mg (0.396 mmole) of benzyl-9-BBN (0.78 mL of a 1.0 M solution in THF) followed by 84 mg (0.79 mmol) of sodium carbonate (0.39 mL of a 2.0 M aqueous solution). The mixture is heated in a microwave apparatus at 100° C. for 10 min. The resin is filtered and the solvent is removed under reduced pressure. Water is added to the residue and the solution is washed with MTBE. The aqueous phase is used directly in the next step.

B. 5-(4-Bromo-2-fluoro-6-hydroxyphenyl)-1,1-dioxo-1,2,5-thiadiazolidin-3-one potassium salt The above solution and 100 mg of 10% Pd/C is hydrogenated at 1 atm for 6 h. The catalyst is filtered and the filtrate is lyophilized to give a powder. This is purified by preparative HPLC using a gradient of 10% MeCN/water—100% MeCN to give 23 mg of product as a white amorphous solid. This is converted to the potassium salt with 1 equiv of potassium bicarbonate: mp>260° C.; $^1$H NMR (DMSO-d$_6$) δ7.32-7.14 (m, 5H), 6.35 (s, 1H), 6.26 (s, broad, 1H), 3.93, (s, 2H), 3.76 (s, 2H); MS (M–H)$^-$=335.

EXAMPLE 9

5-(2-Fluoro-6-hydroxy-4-methylphenyl)-1,1-dioxo-1,2,5-thiadiazolidin-3-one

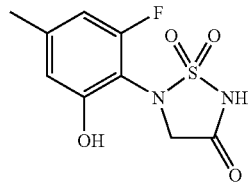

A. 5-(2-Benzyloxy-6-fluoro-4-methylphenyl)-1,1-dioxo-1,2,5-thiadiazolidin-3-one To a microwave vial is added 150 mg (0.33 mmol) of 5-(2-benzyloxy-4-bromo-6-fluorophenyl)-1,1-dioxo-1,2,5-thiadiazolidin-3-one potassium salt and 125 mg of polystyrene-tetrakis(triphenylphosphine)palladium(0) (0.1 mmol/g) followed by 4.5 mL DME. To this is added 80 mg (1.33 mmole) of methylboronic acid followed by 1.3 mL of a 2.0 M aqueous solution of sodium carbonate. The mixture is heated in a microwave apparatus at 120° C. for 30 min. The resin is filtered and the solvent is removed under reduced pressure. Water is added to the residue and the solution is washed with MTBE. The aqueous phase is used directly in the next step.

B. 5-(2-Fluoro-6-hydroxy-4-methylphenyl)-1,1-dioxo-1,2,5-thiadiazolidin-3-one The above solution and 100 mg of 10% Pd/C is hydrogenated at 1 atm for 18 h. The catalyst is filtered and the filtrate is lyophilized to give a powder. This is purified by preparative HPLC using a gradient of 2% MeCN/water—50% MeCN/water to give the product as a white amorphous solid: mp=164-166° C.; $^1$H NMR (DMSO-d$_6$) δ 10.13 (s, 1H), 6.57 (s, 1H), 6.55 (s, 1H), 4.30 (s, 1H), 2.23 (s, 3H); MS (M–H)$^-$=259.

EXAMPLE 10

Benzoic acid 5-benzyl-3-fluoro-2-(1,1,4-trioxo-1,2,5-thiadiazolidin-2-yl)-phenyl ester

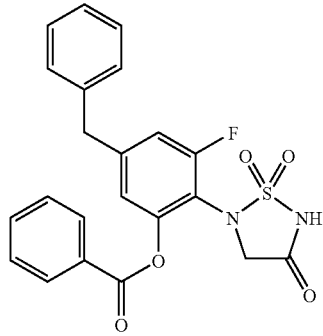

To a solution of 37 mg (0.1 mmol) of 5-(4-bromo-2-fluoro-6-hydroxyphenyl)-1,1-dioxo-1,2,5-thiadiazolidin-3-one potassium salt (Example 8) in 5 mL DMF at 0° C. is added dropwise 0.1 mL of a 1.0 M solution of potassium t-butoxide in THF. The mixture is stirred at 0° C. for 1 min. then 14 mg (0.1 mmol) of benzoyl chloride is added. The mixture is stirred at 0° C. for 5 min. The cloudy solution is clarified by addition of a couple of drops of water and the solution is purified directly by preparative HPLC using a gradient of 10% MeCN/water to 75% MeCN/water to elute the product. Lyophilization provides the product as a white amorphous solid: mp=90-95° C.; MS (M–H)$^-$=439. This is converted to its potassium salt with one equivalent of potassium bicarbonate: $^1$H NMR (DMSO-d$_6$) δ 8.10 (d, J=8.1 Hz, 2H), 7.71 (t, 1H), 7.56 (t, 1H), 7.33-7.28 (m, 4H), 7.25-7.19 (m, 1H), 7.13 (d, J=11.4 Hz, 1H), 7.08 (s, 1H), 3.98 (s, 2H), 3.81 (s, 2H).

EXAMPLE 11

Benzoic acid 3-fluoro-5-methyl-2-(1,1,4-trioxo-1,2,5-thiadiazolidin-2-yl)-phenyl ester

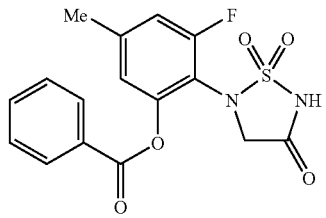

To a solution of 36 mg (0.12 mmol) of 5-(2-fluoro-6-hydroxy-4-methylphenyl)-1,1-dioxo-1,2,5-thiadiazolidin-3-one potassium salt (Example 9) in 0.7 mL of DMF at 0° C. is added 0.12 mL of a 1.0 M solution of potassium t-butoxide in THF dropwise. The mixture is stirred at 0° C. for 1 min. then 17 mg, (0.12 mmole) of benzoyl chloride is added. The mixture is stirred at 0° C. for 10 min. The cloudy solution is clarified by addition of a few drops of water and the solution is purified directly by preparative HPLC using a gradient of 10% MeCN/water to 75% MeCN/water to elute the product. Lyophilization provides the product as a white amorphous solid: mp=88-92° C. This is converted to its potassium salt with one equivalent of potassium bicarbonate: $^1$H NMR (DMSO-d$_6$) δ 8.11 (d, J=7.1 Hz, 2H), 7.72 (t, 1H), 7.6 (t, 2H), 7.08 (d, J=11.6 Hz, 1H), 7.03 (s, 1H), 3.82, (s, 2H), 2.35 (s, 3H); MS (M–H)$^-$=363.

EXAMPLE 12

5-(4-Cyclobutylmethyl-2-fluoro-6-hydroxyphenyl)-1,1-dioxo-1,2,5-thiadiazolidin-3-one potassium salt

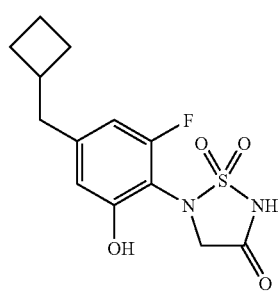

This compound is prepared from 5-(2-benzyloxy-4-bromo-6-fluorophenyl)-1,1-dioxo-1,2,5-thiadiazolidin-3-one potassium salt and cyclobutylmethyl-9-BBN similar to Example 8, Steps A and B, to give the product as a white amorphous solid: mp=138-141° C. This is converted to its potassium salt with one equivalent of potassium bicarbonate: $^1$H NMR (DMSO-d$_6$) δ6.40-6.20 (m, 2H), 3.93 (s, 2H), 1.98 (m, 2H), 1.85-1.32 (m, 7H); MS (M−H)$^-$=313.

EXAMPLE 13

5-(4-Cyclohexylmethyl-2-fluoro-6-hydroxyphenyl)-1,1-dioxo-1,2,5-thiadiazolidin-3-one

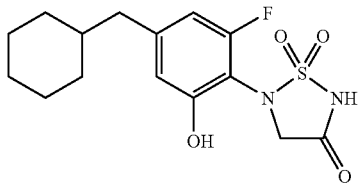

A. Cyclohexylmethyl-9-BBN

To a solution of methylenecyclohexane (287 mg, 3.0 mmol) in THF (7.5 mL) is added 9-BBN (0.4 M, 7.5 mL, 3.0 mmol) at RT and it is stirred for 72 h. The solvent is removed via vacuum to give the title compound and it is used directly in the next step.

B. 5-(4-Cyclohexylmethyl-2-fluoro-6-hydroxyphenyl)-1,1-dioxo-1,2,5-thiadiazolidin-3-one This compound is prepared from 5-(2-benzyloxy-4-bromo-6-fluorophenyl)-1,1-dioxo-1,2,5-thiadiazolidin-3-one potassium salt and cyclohexaylmethyl-9-BBN similar to Example 8, Steps A and B, to give the product as a white amorphous solid: Retention time: 0.26 min (method A). MS (M−H)$^-$=341.

EXAMPLE 14

7-[2-Fluoro-4-hydroxy-3-(1,1,4-trioxo-1,2,5-thiadiazolidin-2-yl)-phenyl]-2,2-dimethylheptanenitrile

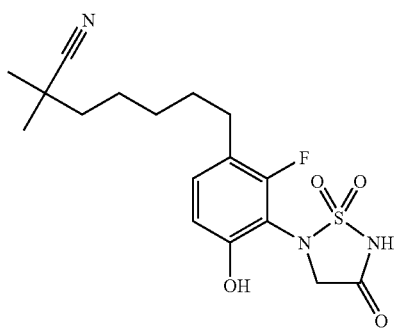

A. 2-Benzyloxy-6-fluorobenzoic acid benzyl ester

To a mixture of 2.6 g (16.7 mmol) of 2-fluoro-6-hydroxybenzoic acid and 6.90 g (50 mmol) of potassium carbonate in 15 mL DMF is slowly added 8.5 g (50 mmol) of benzyl bromide. The mixture is stirred at room temperature for 5 h. Another 1 g of benzyl bromide is added and the mixture is stirred at RT for 18 h. The mixture is poured into water and is extracted with ethyl acetate. The organic phase is washed (3×) with water and 1× with saturated NaCl. The solution is dried over sodium sulfate and the solvent removed under vacuum. The residual oil is purified by flash chromatography to give the product. This is used directly in the next step.

B. 2-Benzyloxy-6-fluorobenzoic acid

To a solution of 7.3 g (21.7 mmol) of 2-benzyloxy-6-fluorobenzoic acid benzyl ester in 75 mL of methanol is added 20 mL of 1.0N NaOH. The mixture is stirred at 50° C. for 24 h. Another 10 mL of 1.0N NaOH is added and the mixture is stirred at RT for 18 h. The solvent is removed under reduced pressure and water is added to the residue. The solution is washed with MTBE and the aqueous phase is acidified with 1N HCl. The mixture is extracted with ethyl acetate (2×) and the organic solution is dried over sodium sulfate. The solvent is removed under reduced pressure to give the product as an oil: $^1$H NMR (CDCl$_3$) δ 7.44-7.31 (m, 6H), 6.84-6.79 (m, 2H), 5.22 (s, 2H).

C. (2-Benzyloxy-6-fluorophenyl)-carbamic acid tert-butyl ester

To a solution of 3.2 g (13.0 mmol) of 2-benzyloxy-6-fluorobenzoic acid in 20 mL of tert-butanol/toluene (1:1) is added 2.0 g (19.8 mmol) of triethylamine followed by dropwise addition of 4.6 g (16.7 mmole) of DPPA. The solution is stirred at RT for 15 min. then at 100° C. for 18 h. The mixture is allowed to cool and then is poured into water. The mixture is extracted with ethyl acetate and the solvent from the organic phase is removed under reduced pressure. Methylene chloride is added to the residue and any insoluble material is filtered. The organic solution is passed through a pad of silica gel using methylene chloride to elute the product. The solvent is removed under reduced pressure to give the product as a white solid: mp=103-106° C.; $^1$H NMR (CDCl$_3$) δ 7.43-7.32 (m, 6H), 7.13-7.06 (m, 1H), 6.78-6.73 (m, 2H), 5.10 (s, 2H), 1.48 (s, 9H).

D. (6-Benzyloxy-3-bromo-2-fluorophenyl)-carbamic acid tert-butyl ester

To a solution of (2-benzyloxy-6-fluorophenyl)-carbamic acid tert-butyl ester (2.35 g, 7.41 mmol) in DMF (20 mL) at 0° C. is added NBS (1.45 g, 8.15 mmol). The mixture is stirred at 0° C. for 30 min., and then at RT for 18 h. It is then poured into water, extracted with EtOAc, washed with water and brine, and dried with MgSO$_4$. The solvent is removed to give the title compound and it is used in the next step.

E. [(6-Benzyloxy-3-bromo-2-fluorophenyl)-tert-butoxycarbonylamino]-acetic acid methyl ester The title compound is prepared analogously to Example 1, Step G.

F. (6-Benzyloxy-3-bromo-2-fluorophenylamino)-acetic acid methyl ester

The title compound is prepared analogously to Example 1, Step I.

G. 5-(6-Benzyloxy-3-bromo-2-fluorophenyl)-1,1-dioxo-1,2,5-thiadiazolidin-3-one The title compound is prepared analogously to Example 1, Steps H to J.

H. (Z)-7-[4-Benzyloxy-2-fluoro-3-(1,1,4-trioxo-1,2,5-thiadiazolidin-2-yl)-phenyl]-2,2-dimethylhept-6-enenitrile A mixture of 5-(6-benzyloxy-3-bromo-2-fluorophenyl)-1,1-dioxo-1,2,5-thiadiazolidin-3-one (1.0 g, 2.4 mmol), 2,2-dimethylhept-6-enenitrile (493 mg, 3.6 mmol), Pd(OAc)$_2$ (108 mg, 0.48 mmol), triethylamine (1.67 mL, 12 mmol) and 2-(di-t-butylphosphino)biphenyl (286 mg, 0.96 mmol) in acetonitrile (15 mL) is stirred in a microwave apparatus at 100° C. for 10 min. It is then filtered and the solvent is removed to give the title compound as a red liquid. The material is used in the next step without purification.

I. 7-[2-Fluoro-4-hydroxy-3-(1,1,4-trioxo-1,2,5-thiadiazolidin-2-yl)-phenyl]-2,2-dimethylheptanenitrile The title compound is prepared analogously to Example 8, Step B: Retention time: 1.34 min (method A). MS (M–H)$^-$= 382.

EXAMPLE 15

5-(2,4-Difluoro-6-hydroxyphenyl)-1,1-dioxo-1,2,5-thiadiazolidin-3-one

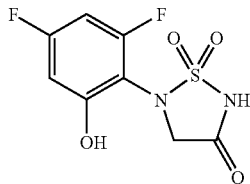

A. 3,5-Difluoro-2-nitrophenol

To a yellow solution of 3,5-difluorophenol (1.50 g, 11.5 mmol) in dichloromethane (20 mL) under a blanket of nitrogen is added ammonium nickel sulfate (4.56 g, 11.54 mmol) with vigorous stirring, followed by the addition of nitric acid (69%, 0.74 mL, 11.54 mmol). The resulting heterogeneous mixture is then stirred at ambient temperature vigorously for 30 minutes. It is filtered and dichloromethane is removed under reduced pressure. The residue is purified by column chromatography to afforded a yellow solid as the title compound.

B. 2-Benzyloxy-4,6-difluoronitrobenzene

The title compound is prepared analogously to Example 14, step A.

C. 2-Benzyloxy-4,6-difluoroaniline

2-Benzyloxy-4,6-difluoronitrobenzene (1.0 g, 3.77 mmol) is reduced in EtOAc (18 mL) and 100 mg of 5% platinum on carbon under a hydrogen balloon for 6 h. The mixture is filtered through Celite and solvent removed under reduced pressure. The residue is purified by column chromatography to give a yellow liquid as the title compound.

D. Methyl (2-benzyloxy-4,6-difluoroanilino)acetate

The title compound is prepared analogously to Example 1, step G.

E. N-(t-Butoxycarbonylsulfamoyl)-N-(2-benzyloxy-4,6-difluorophenyl)glycine methyl ester The title compound is prepared analogously to Example 1, step H.

F. 5-(2,4-Difluoro-6-hydroxyphenyl)-1,1-dioxo-1,2,5-thiadiazolidin-3-one

The title compound is prepared analogously to Example 1, steps I to J and then step N, Retention time: 0.6 min (method A). (M–H)$^-$=263.

EXAMPLE 16

5-(1-Fluoro-3-hydroxy-7-methylnaphthalen-2-yl)-1,1-dioxo-1,2,5-thiadiazolidin-3-one

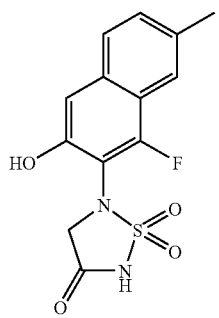

A. (3-Benzyloxy-7-bromonaphthalen-2-yl)-carbamic acid tert-butyl ester

The title compound is prepared analogously to Example 14, Steps A to C, from 7-bromo-3-hydroxy-2-naphthoic acid.

B. [(3-Benzyloxy-7-bromonaphthalen-2-yl)-tert-butoxycarbonyl-amino]-acetic acid methyl ester The title compound is prepared analogously to Example 14, Step E, using sodium hydride to replace potassium carbonate.

C. (3-Benzyloxy-7-bromonaphthalen-2-ylamino)-acetic acid methyl ester

The title compound is prepared analogously to Example 14, Step F.

D. (3-Benzyloxy-7-bromo-1-fluoronaphthalen-2-ylamino)-acetic acid methyl ester To a solution of (3-benzyloxy-7-bromonaphthalen-2-ylamino)-acetic acid methyl ester (5.0 g, 12.5 mmol) in acetonitrile (200 mL) is added SelectFluoro (6.6 g, 18.7 mmol).

The mixture is stirred at RT for 18 h. The solvent is evaporated and the residue is extracted between EtOAc and sat. NaHCO$_3$. The organic layer is washed twice with water, then dried over Na$_2$SO$_4$. The solvent is evaporated to give a brown oil. The oil is then purified by Biotage reverse phase, eluting with 60-80% actonitrile/water to give the title compound.

E. 5-(3-Benzyloxy-7-bromo-1-fluoronaphthalen-2-yl)-1,1-dioxo-1,2,5-thiadiazolidin-3-one The title compound is prepared analogously to Example 1, Steps H to J, from (3-benzyloxy-7-bromo-1-fluoronaphthalen-2-ylamino)-acetic acid methyl ester.

F. 5-(1-Fluoro-3-hydroxy-7-methylnaphthalen-2-yl)-1,1-dioxo-1,2,5-thiadiazolidin-3-one The title compound is prepared analogously to Example 9, Steps A and B, from 5-(3-benzyloxy-7-bromo-1-fluoronaphthalen-2-yl)-1,1-dioxo-1,2,5-thiadiazolidin-3-one: MS (M–H)$^-$=309.

EXAMPLE 17

5-(1-Fluoro-3-hydroxynaphthalen-2-yl)-1,1-dioxo-1,2,5-thiadiazolidin-3-one

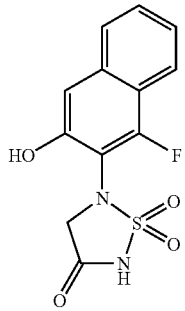

The title compound is obtained as a by product from Example 16: MS (M–H)$^-$=295.

EXAMPLE 18

5-(7-Ethyl-1-fluoro-3-hydroxy-5,6,7,8-tetrahydronaphthalen-2-yl)-1,1-dioxo-1,2,5-thiadiazolidin-3-one

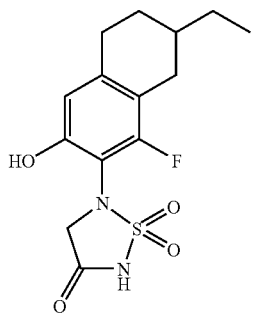

A. 5-(3-Benzyloxy-1-fluoro-7-vinylnaphthalen-2-yl)-1,1-dioxo-1,2,5-thiadiazolidin-3-one To a microwave vial is added 5-(3-benzyloxy-7-bromo-1-fluoronaphthalen-2-yl)-1,1-dioxo-1,2,5-thiadiazolidin-3-one (340 mg, 0.73 mmol) (intermediate from preparing Example 16), 4,4,5,5-tetramethyl-2-vinyl-1,3,2-dioxaborolane (0.24 mL, 1.46 mmol), polystyrene tetrakis(triphenylphosphine)palladium(0) (0.1 mmole/g) (365 mg, 0.0365 mmol), Na$_2$CO$_3$ (2 M, 1.83 mL, 3.65 mmol) and DME (2.5 mL). The mixture is then heated in a microwave at 110° C. for 30 min. The resin is then filtered and the residue is purified quickly by Biotage reverse phase, eluting with 10-90% EtOH/water to give fractions containing the title compound: MS (M+H)$^+$=413. The fractions are combined and used in the next step without concentration.

B. 5-(7-Ethyl-1-fluoro-3-hydroxynaphthalen-2-yl)-1,1-dioxo-1,2,5-thiadiazolidin-3-one To the above solution is added 10% Pd/C (50 mg) and it is stirred under a hydrogen balloon for 18 h. The Pd/C is then filtered and concentrated to give the title compound: MS (M–H)$^-$=323. This is converted to a potassium salt with 1 equiv. of potassium bicarbonate.

C. 5-(7-Ethyl-1-fluoro-3-hydroxy-5,6,7,8-tetrahydronaphthalen-2-yl)-1,1-dioxo-1,2,5-thiadiazolidin-3-one To the above potassium salt in AcOH (1 mL) is added 10% Pd/C (450 mg) and the mixture is vigorously stirred under hydrogen (1 atm) for 72 h. Pd/C is filtered and the filtrate is concentrated. The residue is then dissolved in water, and washed with ether. The water layer is lyophilized to give a solid. The solid is then purified by HPLC to give the title compound: $^1$H NMR (CD$_3$OD) δ 0.86 (t, J=8 Hz, 3H), 1.15-1.32 (m, 3H), 1.38-1.45 (m, 1H), 1.75-1.85 (m, 1H), 1.97 (dd, J=16, 8 Hz, 1H), 2.52-2.78 (m, 3H), 4.26 (s, 2H), 6.34 (s, 1H); MS (M–H)$^-$=327.

EXAMPLE 19

5-[1-Fluoro-3-hydroxy-7-(5-hydroxy-4,4-dimethylpentyl)-naphthalen-2-yl]-1,1-dioxo-1,2,5-thiadiazolidin-3-one

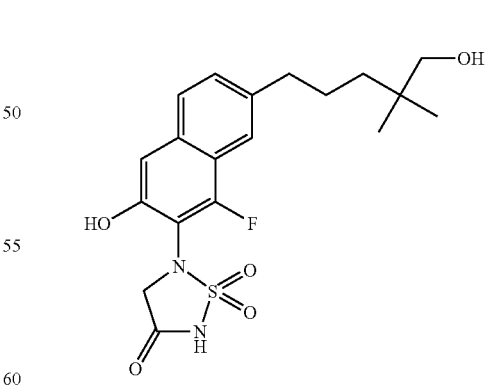

A. (E)-2,2-Dimethyl-5-(4,4,5,5-tetramethyl-1,3,2-dioxaborolan-2-yl)-pent-4-en-1-ol To a solution of 2,2-dimethylpent-4-en-1-ol (4.9 g, 42.9 mmol) in DCM (500 mL) is added 4,4,5,5-tetramethyl-2- vinyl-1,3,2-dioxaborolane (22 mL, 128 mmol) and Grubbs catalyst (3.53 g, 4.29 mmol), and the mixture is heated at 40° C. for 18 h. The mixture is concentrated and washed with sat. NaHCO$_3$ and purified to give the title compound as a greenish crystalline.

B. 5-[1-Fluoro-3-hydroxy-7-(5-hydroxy-4,4-dimethylpentyl)-naphthalen-2-yl]-1,1-dioxo-1,2,5-thiadiazolidin-3-one The title compound is prepared analogously to Example 9, Steps A and B, starting from 5-(3-benzyloxy-7-bromo-1-fluoronaphthalen-2-yl)-1,1-dioxo-1,2,5-thiadiazolidin-3-one and (E)-2,2-dimethyl-5-(4,4,5,5-tetramethyl-1,3,2-dioxaborolan-2-yl)-pent-4-en-1-ol, Retention time=1.16 min (Method A); MS (M−H)$^-$=409.

EXAMPLE 20

5-[8-Fluoro-6-hydroxy-7-(1,1,4-trioxo-1,2,5-thiadiazolidin-2-yl)-naphthalen-2-yl]-2,2-dimethyl-pentanoic acid

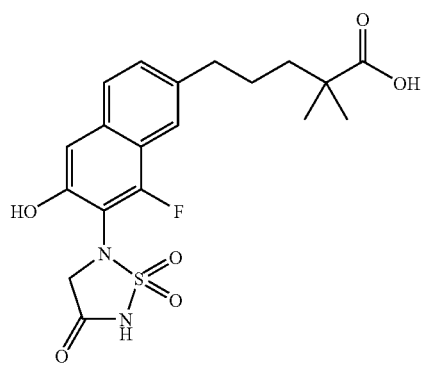

A. 2,2-Dimethyl-pent-4-enoic acid-9-BBN

To a solution of 2,2-dimethyl-pent-4-enoic acid (500 mg, 3.0 mmol) in THF (4 mL) is added 9-BBN (0.5M, 17 mL, 3.0 mmol) at 0° C. and it is stirred at 0° C. for 2 h. The solvent is removed via vacuum to give the title compound and it is used directly in the next step.

B. 5-[8-Fluoro-6-hydroxy-7-(1,1,4-trioxo-1,2,5-thiadiazolidin-2-yl)-naphthalen-2-yl]-2,2-dimethyl-pentanoic acid This compound is prepared from 5-(3-benzyloxy-7-bromo-1-fluoronaphthalen-2-yl)-1,1-dioxo-1,2,5-thiadiazolidin-3-one and 2,2-dimethyl-pent-4-enoic acid-9-BBN similar to Example 8, Steps A and B, except in Step B, Pd(OH)$_2$ is used to replace 10% Pd/C: Retention time=0.98 min (Method A); MS (M−H)$^-$=423.

EXAMPLE 21

The following examples are prepared using appropriate starting materials and general procedures described in Example 10.

| Example | Chemical Name | MS (m/z) |
| --- | --- | --- |
| 21-1 | Benzoic acid 4-fluoro-6-methyl-3-(1,1,4-trioxo-1,2,5-thiadiazolidin-2-yl)-naphthalen-2-yl ester | (M − H)$^-$ = 413 |
| 21-2 | Benzoic acid 6-ethyl-4-fluoro-3-(1,1,4-trioxo-1,2,5-thiadiazolidin-2-yl)-5,6,7,8-tetrahydronaphthalen-2-yl ester | (M − H)$^-$ = 431 |
| 21-3 | Benzoic acid 4-fluoro-3-(1,1,4-trioxo-1,2,5-thiadiazolidin-2-yl)-naphthalen-2-yl ester | (M − H)$^-$ = 399 |
| 21-4 | Benzoic acid 4-fluoro-6-(5-hydroxy-4,4-dimethylpentyl)-3-(1,1,4-trioxo-1,2,5-thiadiazolidin-2-yl)-naphthalen-2-yl ester | (M − H)$^-$ = 513 |
| 21-5 | Benzoic acid 3-fluoro-5-(2-methanesulfonyloxy-5-methylbenzyl)-2-(1,1,4-trioxo-1,2,5-thiadiazolidin-2-yl)-phenyl ester | (M − H)$^-$ = 547 |
| 21-6 | Benzoic acid 3-fluoro-5-(2-methanesulfonyloxy-4-methylbenzyl)-2-(1,1,4-trioxo-1,2,5-thiadiazolidin-2-yl)-phenyl ester | (M − H)$^-$ = 547 |
| 21-7 | Benzoic acid 4-(6-cyano-6,6-dimethylhexyl)-3-fluoro-2-(1,1,4-trioxo-1,2,5-thiadiazolidin-2-yl)-phenyl ester | (M − H)$^-$ = 486 |
| 21-8 | Benzoic acid 3-fluoro-5-(2-methanesulfonylamino-5-methylbenzyl)-2-(1,1,4-trioxo-1,2,5-thiadiazolidin-2-yl)-phenyl ester | (M − H)$^-$ = 546 |
| 21-9 | Benzoic acid 3-fluoro-5-(2-methanesulfonylamino-4-methylbenzyl)-2-(1,1,4-trioxo-1,2,5-thiadiazolidin-2-yl)-phenyl ester | (M − H)$^-$ = 546 |
| 21-10 | Benzoic acid 3-fluoro-5-(2-methanesulfonyloxy-3-methylbenzyl)-2-(1,1,4-trioxo-1,2,5-thiadiazolidin-2-yl)-phenyl ester | (M − H)$^-$ = 547 |

| Example | NMR | Retention time (min) (Method) |
|---|---|---|
| 21-1 | | |
| 21-2 | 1H NMR (CD3OD) δ 1.05 (t, J = 8 Hz, 3H), 1.35-1.52 (m, 3H), 1.57-1.69 (m, 1H), 1.95-2.05 (m, 1H), 2.26 (dd, J = 16, 8 Hz, 1H), 2.82-3.02 (m, 3H), 4.40 (s, 2H), 6.95 (s, 1H), 7.53 (t, J = 8 Hz, 2H), 7.68 (t, J = 8 Hz, 1H), 8.18 (d, J = 8 Hz, 2H) | |
| 21-7 | NMR (DMSO-d6): 8.13-8.11 (m, 2H), 7.74-7.70 (m, 1H), 7.59-7.55 (t, J = 8.09 Hz, 2H), 7.39-7.31 (m, 1H), 7.17-7.12 (m, 1H), 3.86 (s, 2H), 2.67-2.62 (t, J = 7.58 Hz, 1H), 2.51-2.49 (t, J = 2.23 Hz, 1H), 1.64-1.59 (m, 2H), 1.54-1.36 (m, 6H), 1.29-1.25 (m, 6H). | 1.34 (A) |

EXAMPLE 22

5-(4-Ethyl-2-fluoro-6-hydroxyphenyl)-1,1-dioxo-1-[1,2,5]thiadiazolidin-3-one

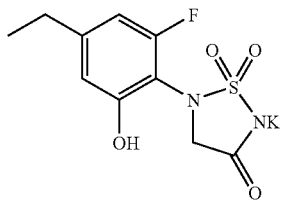

A. 5-(2-Benzyloxy-6-fluoro-4-vinylphenyl)-1,1-dioxo-1-[1,2,5]thiadiazolidin-3-one A mixture of 5-(2-benzyloxy-4-bromo-6-fluoro-phenyl)-1,1-dioxo-1-[1,2,5]thiadiazolidin-3-one (300 mg, 0.72 mmol), 4,4,5,5-tetramethyl-2-vinyl-[1,3,2]dioxaborolane (166 mg, 1.08 mmol), PS-Ph3-Pd (150 mg, 50% wt) and K2CO3 (2N, 1.44 mL) in DME (8 mL) is heated at 130° C. in a microwave apparatus for 3 h. The suspension is filtered and the solvent removed under reduced pressure to afford the crude product as a red oil.

B. 5-(4-Ethyl-2-fluoro-6-hydroxyphenyl)-1,1-dioxo-1-[1,2,5]thiadiazolidin-3-one To a stirred solution of 5-(2-benzyloxy-6-fluoro-4-vinyl-phenyl)-1,1-dioxo-1-[1,2,5]thiadiazolidin-3-one (350 mg, 0.97 mmol) in 10 mL of EtOH/H2O (1:1) is added K2CO3 (138 mg, 1.0 mmol) and Pd/C (100 mg) and then is hydrogenated at 1 atm at RT for 2 h. The suspension is filtered through Celite and solvent is removed by lyophilization. The residue is purified by preparative HPLC to afford the product as a white solid. MS (M−H)⁻=273.

C. 5-(4-Ethyl-2-fluoro-6-hydroxy-phenyl)-1,1-dioxo-1-[1,2,5]thiadiazolidin-3-one Potassium Salt To a solution of 5-(4-ethyl-2-fluoro-6-hydroxy-phenyl)-1,1-dioxo-1-[1,2,5]thiadiazolidin-3-one (35 mg, 0.13 mmol) in 5 mL of water is added KHCO3 (0.5 N, 0.26 mL) and the solution is stirred at RT for 20 min. The solvent is removed by lyophilization to afford the product as a white solid. NMR (methanol-d4): 6.58 (s, 1H), 6.54-6.51 (dd, J=11.12 Hz, 1.52 Hz, 1H), 4.25 (s, 2H), 2.60-2.55 (q, J=7.58 Hz, 2H), 1.23-1.19 (t, J=7.58 Hz, 3H). MS (M−H)⁻=273.

EXAMPLE 23

5-(4-Cyclopentylmethyl-2-fluoro-6-hydroxyphenyl)-1,1-dioxo-1-[1,2,5]thiadiazolidin-3-one

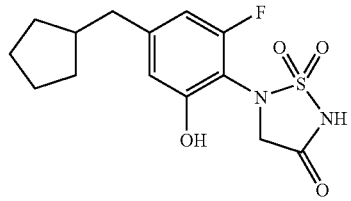

This compound is prepared from 5-(2-benzyloxy-4-bromo-6-fluorophenyl)-1,1-dioxo-1,2,5-thiadiazolidin-3-one potassium salt and cyclopentaylmethyl-9-BBN similar to Example 8, Steps A and B, to give the product as a white amorphous solid: NMR (DMSO-d6): 9.24 (s, 1H), 6.49-6.46 (m, 2H), 3.95 (s, 2H), 2.37-2.35 (d, J=7.33 Hz, 2H), 1.66-1.59 (m, 4H), 1.49-1.43 (m, 1H), 1.19-1.13 (m, 2H), 0.94-0.89 (m, 2H). MS (M−H)⁻=327.

EXAMPLE 24

5-(2,3-Difluoro-6-hydroxy-4-methylphenyl)-1,1-dioxo-1,2,5]thiadiazolidin-3-one

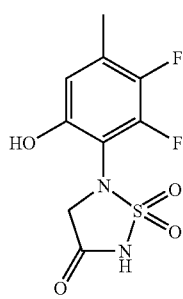

A. 6-Bromo-3,4-difluoro-2-nitrophenol

To a round bottom flask containing 2-bromo-4,5-difluorophenol (2.7 g, 12.9 mmol) and ammonium nickel sulfate (2.6 g, 6.46 mmol) is added dichloromethane (15 mL) at RT. A solution of 70% nitric acid (1.2 ml) is added dropwise and the slurry is stirred for 20 to 30 min. The mixture is then quenched with excess MgSO$_4$, filtered and concentrated. The product is used in the next step without purification.

B. 2-Amino-3,4-difluorophenol

The title compound is prepared analogously to example 9, step B, starting from 6-Bromo-3,4-difluoro-2-nitrophenol, the product is used directly in the next step without purification.

C. N,N-(2,3-Difluoro-6-hydroxyphenyl)-acetamide

A round bottom flask containing 2-Amino-3,4-difluorophenol (1.0 g, 6.96 mmol), THF (10 mL) and saturated aqueous sodium bicarbonate solution (10 mL) is cooled in an ice bath. Acetyl chloride (0.52 mL, 7.31 mmol) is added slowly over 5 min and stirred for an additional 15 min. The mixture is then concentrated, and partitioned between DCM and sodium bicarbonate. The combined organic portion is dried with MgSO$_4$ and concentrated. The residue is purified to give the title compound: MS (M–H)$^-$=186.

D. N-(6-Benzyloxy-2,3-difluorophenyl)-acetamide

The title compound is prepared analogously to example 14, step A, starting from N,N-(2,3-difluoro-6-hydroxyphenyl)-acetamide: MS (M–H)$^-$=276.

E. 6-Benzyloxy-2,3-difluorophenylamine

A round bottom flask containing N-(6-benzyloxy-2,3-difluorophenyl)-acetamide (1.0 g), potassium hydroxide (1.0 g), water (2 mL) and ethanol (10 mL) are heated at 90° C. for 10 h. The mixture is then concentrated and extracted twice with EtOAc and water. The combined organic layers are dried over MgSO$_4$, filtered and concentrated. The product is used directly in the next step.

F. 6-Benzyloxy-4-bromo-2,3-difluoro-phenylamine

A round bottom flask containing N-bromosuccinimide (0.52 mg, 2.93 mmol), and dichloromethane (5 mL) is stirred in an ice bath. A solution of the 6-benzyloxy-2,3-difluorophenylamine (0.69 mg, 2.93 mmol) in 10 mL of dichloromethane is added quickly in one portion. The resulting mixture is stirred for 20 min then water is added and the resulting mixture is extracted twice with DCM. The organic portion is dried over MgSO$_4$, filtered and concentrated to afford the title compound, which is used directly in the next step without purification.

G. 5-(6-Benzyloxy-4-bromo-2,3-difluoro-phenyl)-1,1-dioxo-1,2,5]thiadiazolidin-3-one The title compound is prepared analogously to example 1, steps G, H, I and J, starting from 6-benzyloxy-4-bromo-2,3-difluorophenylamine. The resulting potassium salt is then neutralized with 1N HCl upon work-up to afford the title compound: MS (M–H)$^-$=432.

H. 5-(2,3-Difluoro-6-hydroxy-4-methyl-phenyl)-1,1-dioxo-1,2,5]thiadiazolidin-3-one The title compound is prepared analogously to example 9, steps A and B, starting from 5-(6-benzyloxy-4-bromo-2,3-difluorophenyl)-1,1-dioxo-1,2,5]thiadiazolidin-3-one: Retention time=0.85 min (Method A); MS (M–H)$^-$=277.

EXAMPLE 25

5-(2,3-Difluoro-6-hydroxyphenyl)-1,1-dioxo-1,2,5]thiadiazolidin-3-one

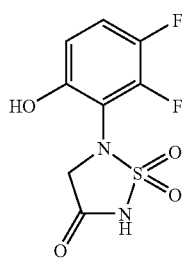

A. 5-(6-Benzyloxy-4-bromo-2,3-difluorophenyl)-1,1-dioxo-1,2,5]thiadiazolidin-3-one The title compound is prepared analogously to example 1, steps G, H, I and J, starting from 6-benzyloxy-4-bromo-2,3-difluorophenylamine, the resulting potassium salt is then neutralized with 1N HCl upon work-up to afford the title compound: MS (M–H)$^-$=432.

B. 5-(2,3-Difluoro-6-hydroxyphenyl)-1,1-dioxo-1,2,5]thiadiazolidin-3-one

The title compound is prepared analogously to example 9, step B, starting from 5-(6-benzyloxy-4-bromo-2,3-difluorophenyl)-1,1-dioxo-1,2,5]thiadiazolidin-3-one, to afford the title compound: Retention time=0.65 min (Method A); MS (M–H)$^-$=263.

EXAMPLE 26

1,1-Dioxo-5-(2,3,6-trifluoro-6-hydroxy-phenyl)-1,2,5]thiadiazolidin-3-one potassium salt

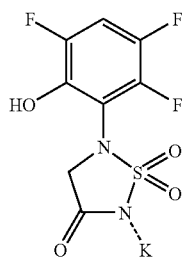

A. 3,4,6-Trifluoro-2-nitrophenol

The title compound is prepared analogously to Example 24, step A, starting with 2,4,5-trifluorophenol, to afford the product which is used directly in the next step.

B. 2-Benzyloxy-1,4,5-trifluoro-3-nitrobenzene

The title compound is prepared analogously to Example 14, step A, starting from 3,4,6-trifluoro-2-nitrophenol, the crude is then purified With column chromatography to afford the product: MS (M−H)⁻=282.

C. 2-Benzyloxy-3,5,6-trifluorophenylamine

A round bottom flask containing 2-benzyloxy-1,4,5-trifluoro-3-nitrobenzene (0.44 g, 1.54 mmol), zinc dust (0.50 g, 7.71 mmol) and solid ammonium chloride (0.17 g, 3.08 mmol) is added a mixture of ethanol and water (2:1 ratio, 15 mL total). The resulting slurry is heated at 60° C. for 90 min. The mixture is filtered, washed with methanol and the filtrate is concentrated. The residue is extracted twice with EtOAc and water, dried over MgSO$_4$ and concentrated. The crude product is used directly in the next step without purification.

D. 5-(2-Benzyloxy-3,5,6-trifluoro-phenyl)-1,1-dioxo-1,2,5]thiadiazolidin-3-one The title compound is prepared analogously to Example 1, steps G, H, I and J, starting from 2-benzyloxy-3,5,6-trifluorophenylamine, the resulting potassium salt is neutralized with aqueous HCl during work-up to afford the desire product: MS (M−H)⁻=371.

E. 1,1-Dioxo-5-(2,3,5-trifluoro-6-hydroxy-phenyl)-1,2,5]thiadiazolidin-3-one The title compound is prepared analogously to Example 8, step B, starting from 5-(2-benzyloxy-3,5,6-trifluorophenyl)-1,1-dioxo-1,2,5]thiadiazolidin-3-one, to afford the desired potassium salt: Retention time=0.60 min (Method A); MS (M−H)⁻=281.

EXAMPLE 27

5-(2-Fluoro-6-hydroxyphenyl)-1,1-dioxo-[1,2,5]thiadiazolidin-3-one potassium salt

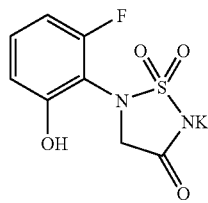

A. Methyl 2-(2-Benzyloxy-6-fluoroanilino)-acetate

A mixture of 2-benzyloxy-6-fluoroaniline (950 mg, 4.37 mmol), methyl bromoacetate (456 μL, 737 mg, 4.82 mmol), and potassium carbonate (1.21 g, 8.76 mmols) in DMF (10 mL) is heated at 60° C. for 18 h. The mixture is poured into ethyl acetate and extracted once with water and five times with brine. The organic layer is dried, filtered, and the solvent removed under reduced pressure to afford a crude oil that is chromatographed on an Isco Companion (80 g silica gel, 0-30% gradient of hexane/ethyl acetate) to afford methyl 2-(2-benzyloxy-6-fluoroanilino)-acetate as an oil. MS (M+1)⁺=290; NMR (CDCl$_3$): δ 7.39 (m, 5H), 6.67 (m, 3H), 5.10 (s, 2H), 4.57 (br s, 1H), 4.11 (m, 2H), 3.72 (s, 3H).

B. N-(t-Butoxycarbonylsulfamoyl)-N-(2-benzyloxy-6-fluorophenyl)glycine methyl ester Chlorosulfonylisocyanate (379 μL, 616 mg, 4.36 mmol) is dissolved in dichloromethane (5 mL) cooled in an ice bath. To this is added a solution of tert.-butanol (416 μL, 322 mg, 4.35 mmol) in dichloromethane (2 mL) dropwise then the mixture is stirred cold for 5 min then 15 min at RT. To the rechilled solution is added dropwise a solution of methyl 2-(2-benzyloxy-6-fluoroanilino)-acetate (840 mg, 2.90 mmol) and Hunig's base (859 μL, 637 mg, 4.93 mmol) in dichloromethane and the resulting solution allowed to warm to RT. After 4 h LC/MS showed the reaction to be complete. The solution is extracted with water, and the organic layer dried, filtered, and solvent removed under reduced pressure. The residual material is chromatographed on an Isco Companion (80 g silica gel, 20-50% gradient of hexane/ethyl acetate) to afford N-(t-butoxycarbonylsulfamoyl)-N-(2-benzyloxy-6-fluorophenyl)glycine methyl ester as an oil. MS (M−1)⁻=467; NMR (CDCl$_3$): δ 7.51 (br s, 1H), 7.40 (m, 5H), 7.24 (m, 2H), 6.78 (m, 2H), 5.16 (s, 2H), 4.60 (dd, J=101 and 18 Hz, 2H), 3.64 (s, 3H), 1.46 (s, 9H).

C. N-Sulfamoyl-N-(2-benzyloxy-6-fluorophenyl)glycine methyl ester

A solution of N-(t-butoxycarbonylsulfamoyl)-N-(2-benzyloxy-6-fluorophenyl)glycine methyl ester (980 mg, 2.09 mmol) 10 mL of trifluoroacetic acid:dichloromethane(1:1) is stirred at RT for 15 min. The solvent is removed under reduced pressure and the residue chromatographed on an Isco Companion (80 g silica gel cartridge, 30-60% gradient of hexane/ethyl acetate) to give N-sulfamoyl-N-(2-benzyloxy-6-fluorophenyl)glycine methyl ester. MS (M−1)⁻: 367 NMR (CDCl$_3$): δ 7.41 (m, 5H), 7.25 (m, 1H), 2.21 (m, 2H), 5.13 (d, 2H, J=5.0 Hz), 5.02 (br s, 2H), 4.39 (dd, J=32 and 19 Hz, 2H), 3.70 (s, 3H).

D. 5-(2-Fluoro-6-hydroxyphenyl)-1,1-dioxo-[1,2,5]thiadiazolidin-3-one potassium salt To a solution of N-sulfamoyl-N-(2-benzyloxy-6-fluorophenyl)glycine methyl ester (455 mg, 1.24 mmol) in THF (3 mL) is added 1.25 mL of 1 M potassium tert.-butoxide (1.25 mmol) and the mixture is stirred at RT for 18 h. An additional 200 μL of potassium tert.-butoxide is added and the solution stirred a further 4.5 h, at which time the starting ester was shown by LC/MS to have been consumed. The solvent is removed under reduced pressure and the residue dissolved in water, and extracted with ether. To the aqueous phase is added ethanol (2 mL) followed by 90 mg of 10% palladium on carbon and the mixture is hydrogenated at 1 atm. The catalyst is then filtered off through Celite, followed by a filter disk, and the filtrate is concentrated, frozen, and lyophilized to give the title compound as an amorphous, hygroscopic material. Retention time=0.44 min (Method A). MS (M−1)⁻=245. HR-MS: (M−1)⁻=245.0029 (theory=245.0032.) NMR (DMSO-d$_6$): δ 7.10 (m, 1H), 6.65 (m, 2H), 3.96 (s, 2H).

EXAMPLE 28

2-(4-{3-[3-Fluoro-5-hydroxy-4-(1,1,4-trioxo-1-[1,2,5]thiadiazolidin-2-yl)-phenyl]-propionylamino}-butoxy)-6-hydroxy-benzoic acid methyl ester potassium salt

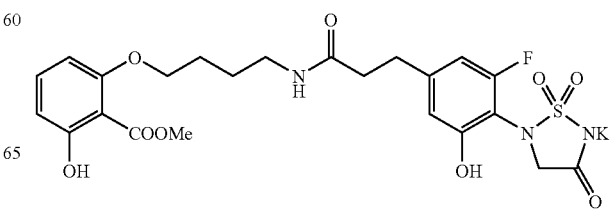

A. 2-(4-tert-Butoxycarbonylaminobutoxy)-6-hydroxybenzoic acid methyl ester

To a solution of methyl 2,6-dihydroxybenzoate (1.0 g, 5.95 mmol) and 4-(Boc-amino)-1-butanol (1.1 mL, 5.95 mmol) in 60 mL of THF is added PPh$_3$ (1.7 g, 6.5 mmol) and DEAD (2.97 mL, 6.5 mmol). The solution is stirred at RT for 18 h then the solvent is removed under reduced pressure. The residue is purified by flash chromatography using a gradient of hexane/EtOAc (5:1 to 2:1) to give the product as a colorless liquid.

B. 2-Benzyloxy-6-(4-tert-butoxycarbonylamino-butoxy)-benzoic acid methyl ester To a solution of 2-(4-tert-butoxycarbonylamino-butoxy)-6-hydroxy-benzoic acid methyl ester (1.5 g, 4.4 mmol) in 20 mL of DMF is added benzyl bromide (0.56 mL, 4.6 mmol) and K$_2$CO$_3$ (1.8 g, 13.0 mmol) and the suspension is stirred at RT for 3 h. The mixture is poured into water and extracted with EtOAc. The organic layer is dried, filtered, and the solvent is removed under reduced pressure to give an oil that is purified by flash chromatography using a gradient of hexane/EtOAc (5:1 to 1:1) to give the product as a colorless liquid.

C. 2-(4-Aminobutoxy)-6-benzyloxybenzoic acid methyl ester

A solution of 2-benzyloxy-6-(4-tert-butoxycarbonylamino-butoxy)-benzoic acid methyl ester (1.6 g, 3.7 mmol) in 30 mL of CH$_2$Cl$_2$/TFA (2:1) is stirred at RT for 20 min. The solvent is removed under reduced pressure and the residue is re-dissolved in CH$_2$Cl$_2$. The solution is washed with sat. NaHCO$_3$, brine, and dried over sodium sulfate. The solvent is removed under reduced pressure to give the crude product as a colorless liquid. This is used directly in the next step.

D. 3-[3-Benzyloxy-5-fluoro-4-(1,1,4-trioxo-1-[1,2,5]thiadiazolidin-2-yl)-phenyl]-acrylic acid tert-butyl ester To a stirred solution of 5-(2-benzyloxy-4-bromo-6-fluorophenyl)-1,1-dioxo-1-[1,2,5]thiadiazolidin-3-one potassium salt (Example 1, step J) (300 mg, 0.72 mmol), tert-butyl acrylate (0.18 mL, 1.08 mmol) and triethylamine (1.0 mL, 7.2 mmol) in MeCN (10 mL) is added Pd(OAc)$_2$ (15 mg, 5% wt). The suspension is stirred at 100° C. for 18 h, filtered and the solvent removed under reduced pressure to give the product as a red oil.

E. 3-[3-Benzyloxy-5-fluoro-4-(1,1,4-trioxo-1-[1,2,5]thiadiazolidin-2-yl)-phenyl]-acrylic acid A solution of 3-[3-benzyloxy-5-fluoro-4-(1,1,4-trioxo-1-[1,2,5]thiadiazolidin-2-yl)-phenyl]-acrylic acid tert-butyl ester (300 mg, 0.65 mmol) in 4 mL of TFA/CH$_2$Cl$_2$ (1:1) is stirred at RT for 30 min. The solvent is removed under reduced pressure, then re-dissolved in CH$_2$Cl$_2$ and re-stripped (4×) to afford the product as a red oil.

F. 2-Benzyloxy-6-(4-{3-[3-benzyloxy-5-fluoro-4-(1,1,4-trioxo-1-[1,2,5]thiadiazolidin-2-yl)-phenyl]-acryloylamino}-butoxy)-benzoic acid methyl ester To a solution of 3-[3-benzyloxy-5-fluoro-4-(1,1,4-trioxo-1-[1,2,5]thiadiazolidin-2-yl)-phenyl]-acrylic acid (250 mg, 0.61 mmol) in DMF (10 mL) is added DIPEA (0.12 mL, 0.67 mmol) and HATU (255 mg, 0.67 mmol) and the mixture is stirred at RT for 10 min. To this is added a solution of 2-(4-aminobutoxy)-6-benzyloxy-benzoic acid methyl ester (302 mg, 0.92 mmol) in DMF (2 mL) and stirring is continued at RT for 18 h. The solvent is removed under reduced pressure to give the crude product as a yellow oil.

G. 2-(4-{3-[3-Fluoro-5-hydroxy-4-(1,1,4-trioxo-1-[1,2,5]thiadiazolidin-2-yl)-phenyl]-propionylamino}-butoxy)-6-hydroxy-benzoic acid methyl ester To a solution of 2-benzyloxy-6-(4-{3-[3-benzyloxy-5-fluoro-4-(1,1,4-trioxo-1-[1,2,5]thiadiazolidin-2-yl)-phenyl]-acryloylamino}-butoxy)-benzoic acid methyl ester (300 mg, 0.42 mmol) in 10 mL of EtOH/H$_2$O (1:1) is added K$_2$CO$_3$ (138 mg, 1 mmol) and 100 mg of 10% Pd/C. The mixture is hydrogenated at 1 atm for 2 h then the catalyst is filtered through Celite. The solvent is removed by lyophilization and the residue is purified by preparative HPLC to afford the product as a white solid. MS (M–H)$^-$=536.

H. 2-(4-{3-[3-Fluoro-5-hydroxy-4-(1,1,4-trioxo-1-[1,2,5]thiadiazolidin-2-yl)-phenyl]-propionylamino}-butoxy)-6-hydroxy-benzoic acid methyl ester potassium salt To a mixture of 2-(4-{3-[3-fluoro-5-hydroxy-4-(1,1,4-trioxo-1-[1,2,5]thiadiazolidin-2-yl)-phenyl]-propionylamino}-butoxy)-6-hydroxy-benzoic acid methyl ester (80 mg, 0.15 mmol) in water (5 mL) is added KHCO$_3$ (0.5 N, 0.30 mL) and the solution is stirred at RT for 20 min. The water is removed by lyophilization to afford the product as a pale yellow solid. Retention time: 0.95 min (method A). MS (M–H)$^-$=536

EXAMPLE 29

7-[2-Fluoro-4-hydroxy-3-(1,1,4-trioxo-1-[1,2,5]thiadiazolidin-2-yl)-phenyl]-2,2-dimethylheptanoic acid dipotassium salt

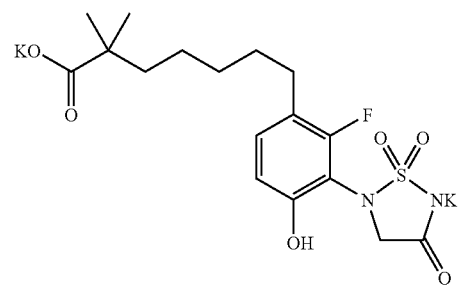

A. 2,2-Dimethyl-hept-6-enoic acid ethyl ester

To a stirred solution of LDA (2M, 5 mL) in THF (5 mL), at –78° C., is added a solution of isobutyric acid ethyl ester (1.16 g, 10 mmol) in THF (3 mL) dropwise. After the addition, the solution is slowly warmed to RT and stirred for 20 min. The temperature is then reduced to –78° C. and a solution of 5-bromo-pent-1-ene (5 mL, 10 mmol) in THF (3 mL) is added dropwise. The solution is warmed to RT and stirred for 18 h.

The mixture is poured into water and extracted with EtOAc. The organic layer is dried, filtered and the solvent is removed under reduced pressure. The residue is purified by flash chromatography using(hexane/EtOAc (10:1) as eluent to give the product as a colorless oil.

B. 2,2-Dimethyl-hept-6-enoic acid

To a solution of 2,2-dimethyl-hept-6-enoic acid ethyl ester (600 mg, 3.3 mmol) in MeOH (10 mL) is added 6N NaOH (5 mL) and the suspension is stirred at RT for 18 h. The solution is acidified with 1N HCl and extracted with EtOAc. The organic layer is dried, filtered and the solvent is removed under reduced pressure to afford the product which is used directly in the next step.

C. 2-Benzyloxy-6-fluorophenylamine

To a solution of 1-benzyloxy-3-fluoro-2-nitrobenzene (10.0 g, 40.5 mmol) in 100 mL of EtOH and 50 mL of 1N HCl is added $SnCl_2$ (38.3 g, 202.5 mmol) and the solution is refluxed for 2 h. After cooling the mixture to RT, it is adjusted to PH>7 with solid $K_2CO_3$ and extracted with EtOAc. The organic layer is washed with water and brine, and dried over sodium sulfate. The solvent is removed under reduced pressure to give the product as a yellow liquid.

D. (2-Benzyloxy-6-fluorophenyl)-carbamic acid tert-butyl ester

To a solution of 2-benzyloxy-6-fluorophenylamine (217 mg, 1.0 mmol) in $CH_2Cl_2$ (10 mL) is added $(Boc)_2O$ (426 mg, 2.0 mmol) and DMAP (24 mg, 0.2 mmol) and the mixture is stirred at RT for 18 h. The solvent is removed under reduced pressure and the residue is purified by flash chromatography using hexane/ethyl acetate (5:1) as eluent to afford the product as a white solid.

E. 7-[2-Fluoro-4-hydroxy-3-(1,1,4-trioxo-1-[1,2,5]thiadiazolidin-2-yl)-phenyl]-2,2-dimethyl-heptanoic acid potassium salt The title compound is prepared from 5-(6-benzyloxy-3-bromo-2-fluorophenyl)-1,1-dioxo-1,2,5-thiadiazolidin-3-one (Example 14, step G) and 2,2-dimethyl-hept-6-enoic acid analogous to Example 14, steps H and I. Retention time: 1.13 min (method A). MS (M−H)⁻=401.

EXAMPLE 30

5-(7-Bromo-1-fluoro-3,6-dihydroxynaphthalen-2-yl)-1,1-dioxo-[1,2,5]thiadiazolidin-3-one

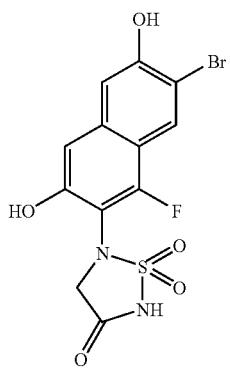

A. 2,7-Bis-benzyloxy-3,6-dibromonaphthalene

To a solution of 3,6-dibromonaphthalene-2,7-diol (67.64 g, 212.7 mmol) in DMF (400 mL) is added $K_2CO_3$ (64.7 g, 468.0 mmol). Benzylbromide (56.0 mL, 468 mmol) is added to the reaction (slight exotherm) and the mixture is stirred at RT for 2 days. The solid is filtered washing with 1:4 DMF/$H_2O$ and set aside for further extraction. The filtrate is extracted 3× with EtOAc and washed with brine. The EtOAc extracts are concentrated under reduced pressure, dissolved in minimum methylene chloride and triturated into hexanes to give product. The filtered solids are washed with hexanes to give additional material which is combined with the triturated solid to give the title compound.

B. (3,6-Bis-benzyloxy-7-bromonaphthalen-2-ylamino)-acetic acid

To a solution of glycine (10 g, 132.2 mmol) in MeCN (100 mL) is added tetrabutylammonium hydroxide (97 mL, 146.5 mmol) and the mixture is stirred at RT until the solution becomes clear. The majority of solvent is removed under reduced pressure to give a slurry containing a white crystalline solid. MeCN is added and removed 7× on vacuum to facilitate the removal of water. This slurry is diluted with up to 130 mL with MeCN to produce a 1.0M solution. Into each of three 20 mL microwave vials is placed 2,7-bis-benzyloxy-3,6-dibrom-naphthalene (3.33 g, 6.66 mmol) and 16.7 mL of the 1.0M slurry described above. The mixtures are bubbled with nitrogen for 15 min then CuI (127 mg, 0.666 mmol) is added to each vessel, and the containers are sealed under nitrogen by 3 purge fill cycles followed by a positive purge and exit needle. The reactions are each heated under microwave irradiation at 150° C. for 30 min. The reaction mixtures are combined and the MeCN is removed under reduced pressure. Saturated $NH_4Cl$ is added and the mixture is extracted 3× with EtOAc. To the aqueous is added 6M NaOH (pH=10) and the mixture is extracted 3× with EtOAc. The EtOac extract is concentrated under reduced pressure and to the residue is added 50 mL of 4:1 $H_2O$/MeOH. To this is added $NaHCO_3$ (210 mg, 20 mmol) (pH=1) allowing the 2,7-bis-benzyloxy-3,6-dibromonaphthalene starting material to be filtered off. The aqueous solution is concentrated to give the title compound which is used without further purification.

C. (3,6-Bis-benzyloxy-7-bromo-naphthalen-2-ylamino)-acetic acid ethyl ester

To a solution of 3,6-bis-benzyloxy-7-bromonaphthalen-2-ylamino)-acetic acid (5.81 g, 1.18 mmol) in 100 mL of ethanol is added conc. HCl (5 mL) and the mixture is stirred at 50° C. for 4 h. The reaction is quenched with saturated ammonium carbonate, extracted 3× with EtOAc, dried over $Na_2SO_4$ and washed with brine. The organic layer is concentrated on vacuum and purified on silica (5-40% EtOAc/hexanes) to give the title compound.

D. (3,6-Bis-benzyloxy-7-bromo-1-fluoronaphthalen-2-ylamino)-acetic acid ethyl ester A suspension of 3,6-bis-benzyloxy-7-bromonaphthalen-2-ylamino)-acetic acid ethyl ester (2.36 g, 4.53 mmol) and 1-fluoro-1,4,6-trimethyl pyridinium tetrafluoro borate (1.13 g, 4.98 mmol) in acetonitrile (20 mL) is heated at under microwave irradiation at 100° C. for 10 min to give a dark purple solution. The solution is poured into brine and extracted 3 times with EtOAc, dried over Na$_2$SO$_4$ and washed with brine. The organic layer is concentrated under reduced pressure and purified on silica (0-20% EtOAc/hexanes) to give the title compound.

E. 5-(3,6-Bis-benzyloxy-7-bromo-1-fluoronaphthalen-2-yl)-1,1-dioxo-[1,2,5]thiadiazolidin-3-one The title compound is prepared from (3,6-bis-benzyloxy-7-bromo-1-fluoronaphthalen-2-ylamino)-acetic acid ethyl ester analogous to Example 1, Steps H to J.

F. 5-(7-Bromo-1-fluoro-3,6-dihydroxynaphthalen-2-yl)-1,1-dioxo-[1,2,5]thiadiazolidin-3-one To a solution of 5-(3,6-bis-benzyloxy-7-bromo-1-fluoronaphthalen-2-yl)-1,1-dioxo-[1,2,5]thiadiazolidin-3-one (232 mg, 0.406 mmol) in CH$_2$Cl$_2$ (3 mL) at 0° C. under nitrogen is added BBr$_3$ (0.731 mL, 0.731 mmol). The reaction is stirred at 0° C. for 5 min then the mixture is quenched with 1N HCl (50 mL) and is extracted 3 times with EtOAc, dried over Na$_2$SO$_4$ and washed with brine. The organic layer is concentrated under reduced pressure and purified on reverse phase HPLC using a gradient of 10-20% MeCN/water (0.1% TFA).

The fractions are concentrated with added methanol to "consume" excess TFA to give the title compound. MS (M+H)$^+$=391. Retention time=1.01 min (Method A).

EXAMPLE 31

5-[8-Fluoro-6-hydroxy-7-(1,1,4-trioxo-1-[1,2,5]thiadiazolidin-2-yl)-naphthalen-2-yl]-2,2-dimethylpentanoic acid isopropyl ester potassium salt

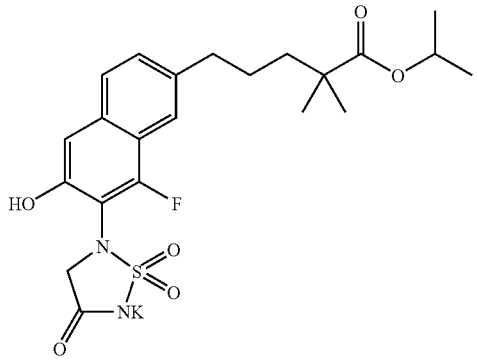

A. 2,2-Dimethyl-pent-4-ynoic acid isopropyl ester

To a solution of LDA (2M in THF, 5 mL) in THF (5 mL), at -78° C. is added a solution of isobutyric acid isopropyl ester (1.3 g, 10 mmol) in THF (3 mL) dropwise. After the addition is complete, the solution is slowly warmed to 0° C. and stirred there for 1 h. The temperature is reduced to -78° C. and a solution of 3-bromo-propyne (1.2 g, 10 mmol) in THF (3 mL) is added dropwise then the solution is allowed to warm to RT and stirred for 18 h. The mixture is poured into water and extracted with EtOAc. The organic layer is dried, filtered and the solvent is removed under reduced pressure. The residue is purified by flash chromatography using hexane/EtOAc (10:1) as eluent to give the product as a colorless liquid.

B. 2,2-Dimethyl-5-(4,4,5,6-tetramethyl-[1,3,2]dioxaborolan-2-yl)-pent-4-enoic acid isopropyl ester To a solution of 2,2-dimethyl-pent-4-ynoic acid isopropyl ester (504 mg, 3.0 mmol) in CH$_2$Cl$_2$ (8 mL) at 0° C., is added 4,4,5,5-tetramethyl-[1,3,2]dioxaborolane (0.48 mL, 3.3 mmol) dropwise and the solution is stirred at 0° C. for 10 min. The solution is transferred to a flask which contains bis(cyclopentadienyl)-zirconium(IV) chloride hydride (38.7 mg, 0.15 mmol) through a cannula and the suspension is stirred at RT for 18 h. The mixture is poured into water and the organic layer is dried, filtered and the solvent is removed under reduced pressure. The residue is purified by flash chromatography using hexanes/EtOAc (9:1) to give the product as a yellow liquid.

C. 5-[6-Benzyloxy-8-fluoro-7-(1,1,4-trioxo-1-[1,2,5]thiadiazolidin-2-yl)-naphthalen-2-yl]-2,2-dimethyl-pent-4-enoic acid isopropyl ester A mixture of 5-(3-benzyloxy-7-bromo-1-fluoro-naphthalen-2-yl)-1,1-dioxo-1-[1,2,5]thiadiazolidin-3-one (Example 16, step E) (400 mg, 0.86 mmol), 2,2-dimethyl-5-(4,4,5,5-tetramethyl-[1,3,2]dioxaborolan-2-yl)-pent-4-enoic acid isopropyl ester (509 mg, 1.72 mmol), PS-Ph$_3$-Pd (200 mg, 50% wt) and 2N K$_2$CO$_3$ (1.72 mL) in DME (8 mL) is heated at 120° C. in a microwave apparatus for 15 min. The suspension is filtered and the solvent removed under reduced pressure to afford the crude product as a red oil.

D. 5-[8-Fluoro-6-hydroxy-7-(1,1,4-trioxo-1-[1,2,5]thiadiazolidin-2-yl)-naphthalen-2-yl]-2,2-dimethyl-pentanoic acid isopropyl ester To a solution of 5-[6-benzyloxy-8-fluoro-7-(1,1,4-trioxo-1-[1,2,5]thiadiazolidin-2-yl)-naphthalen-2-yl]-2,2-dimethyl-pent-4-enoic acid isopropyl ester (400 mg, 0.86 mmol) in 10 mL of EtOH/H$_2$O (1:1) is added K$_2$CO$_3$ (138 mg, 1 mmol) and 10% Pd/C (100 mg). The mixture is hydrogenated at 1 atm for 2 h and the catalyst is filtered through Celite. The solvent is removed by lyophilization and the residue is purified by preparative HPLC to afford the product as a white solid. MS (M-H)$^-$=465.

F. 5-[8-Fluoro-6-hydroxy-7-(1,1,4-trioxo-1-[1,2,5]thiadiazolidin-2-yl)-naphthalen-2-yl]-2,2-dimethyl-pentanoic acid isopropyl ester potassium salt To 5-[8-fluoro-6-hydroxy-7-(1,1,4-trioxo-1-[1,2,5]thiadiazolidin-2-yl)-naphthalen-2yl]-2,2-dimethyl-pentanoic acid isopropyl ester (110 mg, 0.24 mmol) in water (5 mL) is added KHCO$_3$ (0.5 N, 0.48 mL) and the solution is stirred at RT for 20 min. The solvent is removed by lyophilization to afford the product as a white solid. NMR (DMSO-d6): δ 9.54 (s, 1H), 7.66-7.64 (d, J=8.59 Hz, 1H), 7.61 (s, 1H), 7.31-7.29 (d, J=8.59 Hz, 1H), 7.02 (s, 1H), 4.87-4.80 (m, 1H), 4.07 (s, 2H), 2.70-2.67 (t, J=6.32 Hz, 2H), 1.58-1.49 (m, 4H), 1.13-1.11 (d, J=6.32 Hz, 6H), 1.06 (s, 6H). MS (M−H)⁻=465.

EXAMPLE 32

5-(7-Bromo-1-fluoro-3-hydroxy-naphthalen-2-yl)-1,1-dioxo-[1,2,5]thiadiazolidin-3-one To a 0° C. solution of 5-(7-Bromo-1-fluoro-3-hydroxy-naphthalen-2-yl)-1,1-dioxo-[1,2,5]thiadiazolidin-3-one (100 mg, 0.215 mmol) in dichloromethane (1 mL) is added 1N boron tribromide in dichloromethane (0.387 mL, 0.387 mmol). The reaction is stirred for 15 minutes, then quenched by addition of sodium bicarbonate and extracted with 3 portions of ethyl acetate. The organic layer is dried over sodium sulfate, filtered and the solvent removed under reduced pressure. The crude product is purified by preparative HPLC to afford the product. MS (M−H)⁻=374.

EXAMPLE 33

The following examples are prepared using appropriate starting materials and general procedures described in Example 31.

| Example | Chemical Name | MS (m/z) |
|---|---|---|
| 33-1 | 5-[8-Fluoro-6-hydroxy-7-(1,1,4-trioxo-[1,2,5]thiadiazolidin-2-yl)-naphthalen-2-yl]-2,2-dimethyl-pentanoic acid methyl ester | (M − H)⁻ = 437 |
| 33-2 | 5-[8-Fluoro-6-hydroxy-7-(1,1,4-trioxo-[1,2,5]thiadiazolidin-2-yl)-naphthalen-2-yl]-2,2-dimethyl-pentanoic acid ethyl ester | (M − H)⁻ = 451 |
| 33-3 | 5-[8-Fluoro-6-hydroxy-7-(1,1,4-trioxo-[1,2,5]thiadiazolidin-2-yl)-naphthalen-2-yl]-2,2-dimethyl-pentanoic acid butyl ester | (M − H)⁻ = 479 |

| Example | NMR | Retention time RT (min) (Method) |
|---|---|---|
| 33-1 | | 1.27 min (Method A) |
| 33-2 | | 1.31 min (Method A) |
| 33-3 | NMR (DMSO-d6): 9.56 (s, 1H), 7.63-7.59 (m, 2H), 7.29-7.27 (d, J = 7.83 Hz, 1H), 6.98 (s, 1H), 4.09 (s, 2H), 3.99-3.96 (t, J = 6.57 Hz, 2H), 2.69-2.66 (t, J = 5.05 Hz, 2H), 1.51-1.49 (m, 6H), 1.31-1.25 (m, 2H), 1.08 (s, 6H), 0.87-0.83 (t, J = 7.33 Hz, 3H). | |

EXAMPLE 34

The following examples are prepared using appropriate starting materials and general procedures described in Example 20 with the following exception. For 34-6 and 34-7, after step A of Example 9, the material is esterified similarly to 35-1, except that HCl is substituted for H₂SO₄.

| Example | Chemical Name | MS (m/z) |
|---|---|---|
| 34-1 | (S)-5-[8-Fluoro-6-hydroxy-7-(1,1,4-trioxo-[1,2,5]thiadiazolidin-2-yl)-naphthalen-2-yl]-2-methyl-pentanoic acid | (M − H)⁻ = 409 |
| 34-2 | (R)-5-[8-Fluoro-6-hydroxy-7-(1,1,4-trioxo-[1,2,5]thiadiazolidin-2-yl)-naphthalen-2-yl]-2-methyl-pentanoic acid | (M − H)⁻ = 409 |
| 34-3 | 5-[1-Fluoro-3-hydroxy-7-(4-hydroxy-4-methyl-pentyl)-naphthalen-2-yl]-1,1-dioxo-[1,2,5]thiadiazolidin-3-one | (M − H)⁻ = 395 |
| 34-4 | 5-[8-Fluoro-6-hydroxy-7-(1,1,4-trioxo-[1,2,5]thiadiazolidin-2-yl)-naphthalen-2-yl]-pentanoic acid | (M − H)⁻ = 395 |
| 34-5 | 4-[8-Fluoro-6-hydroxy-7-(1,1,4-trioxo-[1,2,5]thiadiazolidin-2-yl)-naphthalen-2-yl]-butyric acid | (M − H)⁻ = 381 |
| 34-6 | 5-[8-Fluoro-6-hydroxy-7-(1,1,4-trioxo-[1,2,5]thiadiazolidin-2-yl)-naphthalen-2-yl]-pentanoic acid ethyl ester | (M − H)⁻ = 423 |
| 34-7 | 5-[8-Fluoro-6-hydroxy-7-(1,1,4-trioxo-[1,2,5]thiadiazolidin-2-yl)-naphthalen-2-yl]-pentanoic acid methyl ester | (M − H)⁻ = 409 |
| 34-8 | 5-[7-(4,4-Dimethyl-pentyl)-1-fluoro-3-hydroxy-naphthalen-2-yl]-1,1-dioxo-[1,2,5]thiadiazolidin-3-one | (M − H)⁻ = 393 |

| Example | NMR | Retention time RT (min)(Method) |
|---|---|---|
| 34-1 | | 0.99 min (Method A) |
| 34-2 | | 0.96 min (Method A) |
| 34-3 | | 1.11 min (Method A) |
| 34-4 | | 0.93 min (Method A) |
| 34-5 | | 0.77 min (Method A) |
| 34-6 | | 1.19 min (Method A) |
| 34-7 | | 1.12 (Method A) |
| 34-8 | | 1.49 min (Method A) |

| Example | NMR | RT (min) (Method) |
|---|---|---|
| 35-1 | | 1.32 min (Method A) |
| 35-2 | | 0.98 min (Method A) |
| 35-3 | | 1.30 min (Method A) |
| 35-4 | | 0.78 min (Method A) |

EXAMPLE 35

The following examples are prepared using appropriate starting materials and general procedures described in Example 16 and Example 9 with the following exceptions. For 35-1, after step A of Example 9, the material is esterified by stirring 100 mg of 3-{3-[6-Benzyloxy-8-fluoro-7-(1,1,4-trioxo-[1,2,5]thiadiazolidin-2-yl)-naphthalen-2-yl]-phenyl}-propionic acid with 10 mL Ethanol and 0.2 mL $H_2SO_4$ for 3.5 hours. Ethyl acetate is added followed by evaporation of ethanol. The material is then extracted between ethyl acetate and water, and the organic layer is dried over sodium sulfate, filtered, concentrated to afford 3-{3-[6-Benzyloxy-8-fluoro-7-(1,1,4-trioxo-[1,2,5]thiadiazolidin-2-yl)-naphthalen-2-yl]-phenyl}-propionic acid ethyl ester and used in the next step, analogous to Example 9 step B, without purification. For 35-4, after step A of Example 9, the ester, 3-[6-Benzyloxy-8-fluoro-7-(1,1,4-trioxo-[1,2,5]thiadiazolidin-2-yl)-naphthalen-2-yl]-benzoic acid ethyl ester is hydrolyzed by addition of 0.84 mL of 1 M NaOH and heated in by microwave irradition for 30 min at 120° C. The aqueous layer is filtered and extracted with 1:1 ether hexanes. The aqueous layer is acidified and extracted 3 times with EtOAc, and the combined organic layers are dried over $Mg_2SO_4$, filtered and concentrated to afford 3-[6-Benzyloxy-8-fluoro-7-(1,1,4-trioxo-[1,2,5]thiadiazolidin-2-yl)-naphthalen-2-yl]-benzoic acid which is used in the next step without purification.

EXAMPLE 36

5-[1-Fluoro-3-hydroxy-7-(4-formyl-4-methyl-pentyl)-naphthalen-2-yl]-1,1-dioxo-[1,2,5]thiadiazolidin-3-one

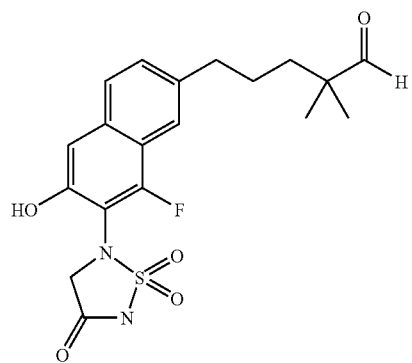

To a stirred solution of 5-[1-fluoro-3-hydroxy-7-(5-hydroxy-4,4-dimethylpentyl)-naphthalen-2-yl]-1,1-dioxo-1,2,5-thiadiazolidin-3-one (1.00 g, 2.23 mmol) in anhydrous DMSO (10 ml) at room temperature was added triethylamine (2.17 mL, 15.6 mmol) followed by a slow addition of a solution of sulfur trioxide pyridine complex (1.28 g, 8.02 mmol) in anhydrous DMSO (12 mL). The reaction mixture was stirred for 30 min and cold water (70 mL) was slowly added. The above content was acidified with 3 N HCl to pH 2.5, extracted twice with EtOAc, washed with brine, dried

| Example | Chemical Name | MS (m/z) |
|---|---|---|
| 35-1 | 3-{3-[8-Fluoro-6-hydroxy-7-(1,1,4-trioxo-[1,2,5]thiadiazolidin-2-yl)-naphthalen-2-yl]-phenyl}-propionic acid ethyl ester | $(M - H)^- = 471$ |
| 35-2 | 3-{3-[8-Fluoro-6-hydroxy-7-(1,1,4-trioxo-[1,2,5]thiadiazolidin-2-yl)-naphthalen-2-yl]-phenyl}-propionic acid | $(M - H)^- = 443$ |
| 35-3 | 3-[8-Fluoro-6-hydroxy-7-(1,1,4-trioxo-[1,2,5]thiadiazolidin-2-yl)-naphthalen-2-yl]-benzonitrile | $(M - H)^- = 396$ |
| 35-4 | 3-[8-Fluoro-6-hydroxy-7-(1,1,4-trioxo-[1,2,5]thiadiazolidin-2-yl)-naphthalen-2-yl]-benzoic acid | $(M - H)^- = 415$ | over MgSO$_4$, and concentrated to yield the title compound as a light brown solid. Retention time=1.22 min (Method A); MS (M−H)$^-$=407.

The table below shows the inhibitory activity (IC50 values) of two representative compounds of the invention to human PTP-1B.

| Compound | IC50 (nM) |
| --- | --- |
| Example No. 26 | 158 nM |
| Example No. 13 | 104 nM |

These examples are not limitative.

What is claimed is:

1. A compound of the formula

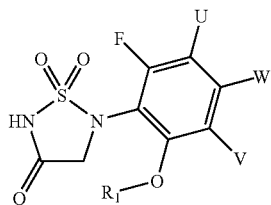

(I)

wherein

R$_1$ is hydrogen, —C(O)R$_2$, —C(O)NR$_3$R$_4$ or —C(O)OR$_5$ in which

R$_2$ and R$_3$ are, independently from each other, hydrogen, cycloalkyl, aryl, heterocyclyl, aralkyl, heteroaralkyl or alkyl optionally substituted with one to four substituents selected from the group consisting of halogen, cycloalkyl, cycloalkoxy, alkoxy, alkyloxyalkoxy, amino, alkylamino, dialkylamino, aryl, aryloxy and heterocyclyl;

R$_4$ and R$_5$ are, independently from each other, cycloalkyl, aryl, heterocyclyl, aralkyl, heteroaralkyl or alkyl optionally substituted with one to four substituents selected from the group consisting of halogen, cycloalkyl, cycloalkoxy, alkoxy, alkyloxyalkoxy, amino, alkylamino, dialkylamino, aryl, aryloxy and heterocyclyl;

U, W and V are, independently from each other, hydrogen, hydroxy, halogen, cyano, nitro, alkoxy, alkylthio, alkylthiono, sulfonyl, free or esterified carboxy, carbamoyl, sulfamoyl, optionally substituted amino, cycloalkyl, aryl, aryloxy, arylthio, heterocyclyl, heterocycloyloxy, alkenyl, alkynyl or (C$_{1-8}$)alkyl optionally substituted with one to four substituents selected from the group consisting of halogen, hydroxy, cycloalkyl, cycloalkoxy, acyl, acyloxy, alkoxy, alkyloxyalkoxy, amino, alkylamino, dialkylamino, acylamino, carbamoyl, thiol, alkylthio, alkylthiono, sulfonyl, sulfonamido, sulfamoyl, nitro, cyano, free or esterified carboxy, aryl, aryloxy, arylthio, alkenyl, alkynyl, aralkoxy, heteroaralkoxy, heterocyclyl and heterocyclyloxy; or U and W combined together with the carbon atoms to which they are attached form an optionally substituted aromatic, or a partially or fully saturated nonaromatic 5- to 8-membered carbocyclic; or W and V combined together with the carbon atoms to which they are attached form an optionally substituted aromatic, or partially or fully saturated nonaromatic 5- to 8-membered carbocyclic or heterocyclic ring;

or a pharmaceutically acceptable salt thereof.

2. The compound according to claim 1, wherein

U and W combined together with the carbon atoms to which they are attached form an optionally substituted aromatic, or a partially or fully saturated nonaromatic 5- to 8-membered carbocyclic;

V is hydrogen;

or a pharmaceutically acceptable salt thereof.

3. The compound according to claim 2 of the formula

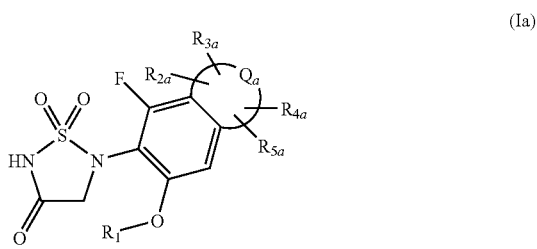

(Ia)

wherein

R$_1$ is hydrogen, —C(O)R$_2$, —C(O)NR$_3$R$_4$ or —C(O)OR$_5$ in which

R$_2$ and R$_3$ are, independently from each other, hydrogen, cycloalkyl, aryl, heterocyclyl, aralkyl, heteroaralkyl or alkyl optionally substituted with one to four substituents selected from the group consisting of halogen, cycloalkyl, cycloalkoxy, alkoxy, alkyloxyalkoxy, amino, alkylamino, dialkylamino, aryl, aryloxy and heterocyclyl;

R$_4$ and R$_5$ are, independently from each other, cycloalkyl, aryl, heterocyclyl, aralkyl, heteroaralkyl or alkyl optionally substituted with one to four substituents selected from the group consisting of halogen, cycloalkyl, cycloalkoxy, alkoxy, alkyloxyalkoxy, amino, alkylamino, dialkylamino, aryl, aryloxy and heterocyclyl;

Q$_a$ combined together with the carbon atoms to which it is attached form an aromatic, or a partially or fully saturated nonaromatic 5- to 8-membered carbocyclic;

R$_{2a}$, R$_{3a}$, R$_{4a}$ and R$_{5a}$ are, independently from each other, hydrogen, hydroxy, halogen, cyano, nitro, alkoxy, alkylthio, alkylthiono, sulfonyl, free or esterified carboxy, carbamoyl, sulfamoyl, optionally substituted amino, cycloalkyl, aryl, heterocyclyl, alkenyl, alkynyl or (C$_{1-8}$) alkyl optionally substituted with one to four substituents selected from the group consisting of halogen, hydroxy, cycloalkyl, cycloalkoxy, acyl, acyloxy, alkoxy, alkyloxyalkoxy, amino, alkylamino, dialkylamino, acylamino, carbamoyl, thiol, alkylthio, alkylthiono, sulfonyl, sulfonamido, sulfamoyl, nitro, cyano, free or esterified carboxy, aryl, aryloxy, arylthio, alkenyl, alkynyl, aralkoxy, heteroaralkoxy, heterocyclyl and heterocyclyloxy; or R$_{2a}$ and R$_{3a}$ combined are alkylene which together with the ring atoms to which they are attached form a 3- to 7-membered fused ring; or R$_{2a}$ and R$_{3a}$ combined are alkylene which together with the carbon atom to which they are attached form a 3- to 7-membered spirocyclic ring;

or a pharmaceutically acceptable salt thereof.

4. The compound according to claim 3, wherein
Q$_a$ combined together with the carbon atoms to which it is attached form an aromatic, or a partially or fully saturated 5- to 6-membered carbocyclic ring;
or a pharmaceutically acceptable salt thereof.

5. The compound according to claim 4 of the formula

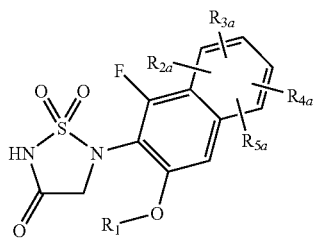

(Ia$_1$)

wherein

R$_1$ is hydrogen, —C(O)R$_2$, —C(O)NR$_3$R$_4$ or —C(O)OR$_5$ in which

R$_2$ and R$_3$ are, independently from each other, hydrogen, cycloalkyl, aryl, heterocyclyl, aralkyl, heteroaralkyl or alkyl optionally substituted with one to four substituents selected from the group consisting of halogen, cycloalkyl, cycloalkoxy, alkoxy, alkyloxyalkoxy, amino, alkylamino, dialkylamino, aryl, aryloxy and heterocyclyl;

R$_4$ and R$_5$ are, independently from each other, cycloalkyl, aryl, heterocyclyl, aralkyl, heteroaralkyl or alkyl optionally substituted with one to four substituents selected from the group consisting of halogen, cycloalkyl, cycloalkoxy, alkoxy, alkyloxyalkoxy, amino, alkylamino, dialkylamino, aryl, aryloxy and heterocyclyl;

R$_{2a}$, R$_{3a}$, R$_{4a}$ and R$_{5a}$ are, independently from each other, hydrogen, hydroxy, halogen, cyano, nitro, alkoxy, alkylthio, alkylthiono, sulfonyl, free or esterified carboxy, carbamoyl, sulfamoyl, optionally substituted amino, cycloalkyl, aryl, heterocyclyl, alkenyl, alkynyl or (C$_{1-8}$) alkyl optionally substituted with one to four substituents selected from the group consisting of halogen, hydroxy, cycloalkyl, cycloalkoxy, acyl, acyloxy, alkoxy, alkyloxyalkoxy, amino, alkylamino, dialkylamino, acylamino, carbamoyl, thiol, alkylthio, alkylthiono, sulfonyl, sulfonamido, sulfamoyl, nitro, cyano, free or esterified carboxy, aryl, aryloxy, arylthio, alkenyl, alkynyl, aralkoxy, heteroaralkoxy, heterocyclyl and heterocyclyloxy; or R$_{2a}$ and R$_{3a}$ combined are alkylene which together with the ring atoms to which they are attached form a 5- to 7-membered fused ring; or or a pharmaceutically acceptable salt thereof.

6. The compound according to claim 5, wherein

R$_{4a}$ and R$_{5a}$ are hydrogen;

or a pharmaceutically acceptable salt thereof.

7. The compound according to claim 6 of the formula

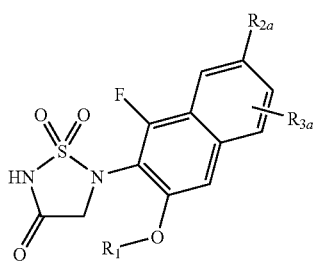

(Ia$_2$)

wherein

R$_1$ is hydrogen, —C(O)R$_2$, —C(O)NR$_3$R$_4$ or —C(O)OR$_5$ in which

R$_2$ and R$_3$ are, independently from each other, hydrogen, cycloalkyl, aryl, heterocyclyl, aralkyl, heteroaralkyl or alkyl optionally substituted with one to four substituents selected from the group consisting of halogen, cycloalkyl, cycloalkoxy, alkoxy, alkyloxyalkoxy, amino, alkylamino, dialkylamino, aryl, aryloxy and heterocyclyl;

R$_4$ and R$_5$ are, independently from each other, cycloalkyl, aryl, heterocyclyl, aralkyl, heteroaralkyl or alkyl optionally substituted with one to four substituents selected from the group consisting of halogen, cycloalkyl, cycloalkoxy, alkoxy, alkyloxyalkoxy, amino, alkylamino, dialkylamino, aryl, aryloxy and heterocyclyl;

R$_{2a}$ and R$_{3a}$ are, independently from each other, hydrogen, hydroxy, halogen, cyano, nitro, alkoxy, alkylthio, alkylthiono, sulfonyl, free or esterified carboxy, carbamoyl, sulfamoyl, optionally substituted amino, cycloalkyl, aryl, heterocyclyl, alkenyl, alkynyl or (C$_{1-8}$)alkyl optionally substituted with one to four substituents selected from the group consisting of halogen, hydroxy, cycloalkyl, cycloalkoxy, acyl, acyloxy, alkoxy, alkyloxyalkoxy, amino, alkylamino, dialkylamino, acylamino, carbamoyl, thiol, alkylthio, alkylthiono, sulfonyl, sulfonamido, sulfamoyl, nitro, cyano, free or esterified carboxy, aryl, aryloxy, arylthio, alkenyl, alkynyl, aralkoxy, heteroaralkoxy, heterocyclyl and heterocyclyloxy;

or a pharmaceutically acceptable salt thereof.

8. The compound according to claim 7, wherein

R$_{2a}$ is —Y$_a$—(CH$_2$)$_n$—CR$_{6a}$R$_{7a}$—(CH$_2$)$_m$—X$_a$ in which

Y$_a$ is oxygen or S(O)$_q$ in which q is zero or an integer of 1 or 2; or

Y$_a$ is trans CH=CH; or

Y$_a$ is absent;

n is an integer from 1 to 6;

R$_{6a}$ and R$_{7a}$ are, independently from each other, hydrogen or lower alkyl; or R$_{6a}$ and R$_{7a}$ combined are alkylene which together with the carbon atom to which they are attached form a 3- to 7-membered ring;

m is zero or an integer of 1 or 2;

X$_a$ is hydroxy, alkoxy, cycloalkyl, cycloalkoxy, acyl, acyloxy, carbamoyl, cyano, trifluoromethyl, free or esterified carboxy, monocyclic aryl or heterocyclyl;

or a pharmaceutically acceptable salt thereof.

9. The compound according to claim 4 of the formula (Ia₃)

wherein

R₁ is hydrogen, —C(O)R₂, —C(O)NR₃R₄ or —C(O)OR₅ in which

R₂ and R₃ are, independently from each other, hydrogen, cycloalkyl, aryl, heterocyclyl, aralkyl, heteroaralkyl or alkyl optionally substituted with one to four substituents selected from the group consisting of halogen, cycloalkyl, cycloalkoxy, alkoxy, alkyloxyalkoxy, amino, alkylamino, dialkylamino, aryl, aryloxy and heterocyclyl;

R₄ and R₅ are, independently from each other, cycloalkyl, aryl, heterocyclyl, aralkyl, heteroaralkyl or alkyl optionally substituted with one to four substituents selected from the group consisting of halogen, cycloalkyl, cycloalkoxy, alkoxy, alkyloxyalkoxy, amino, alkylamino, dialkylamino, aryl, aryloxy and heterocyclyl;

$R_{2a}$, $R_{3a}$, $R_{4a}$ and $R_{5a}$ are, independently from each other, hydrogen, hydroxy, halogen, cyano, nitro, alkoxy, alkylthio, alkylthiono, sulfonyl, free or esterified carboxy, carbamoyl, sulfamoyl, optionally substituted amino, cycloalkyl, aryl, heterocyclyl, alkenyl, alkynyl or ($C_{1-8}$) alkyl optionally substituted with one to four substituents selected from the group consisting of halogen, hydroxy, cycloalkyl, cycloalkoxy, acyl, acyloxy, alkoxy, alkyloxyalkoxy, amino, alkylamino, dialkylamino, acylamino, carbamoyl, thiol, alkylthio, alkylthiono, sulfonyl, sulfonamido, sulfamoyl, nitro, cyano, free or esterified carboxy, aryl, aryloxy, arylthio, alkenyl, alkynyl, aralkoxy, heteroaralkoxy, heterocyclyl and heterocyclyloxy; or $R_{2a}$ and $R_{3a}$ combined are alkylene which together with the ring atoms to which they are attached form a 3- to 7-membered fused ring; or $R_{2a}$ and $R_{3a}$ combined are alkylene which together with the carbon atom to which they are attached form a 3- to 7-membered spirocyclic ring;

p is zero or 1;

or a pharmaceutically acceptable salt thereof.

10. The compound according to claim 9, wherein $R_{4a}$ and $R_{5a}$ are hydrogen;

or a pharmaceutically acceptable salt thereof.

11. The compound according to claim 9, wherein $R_{2a}$ and $R_{3a}$ are, independently from each other, hydrogen, halogen or ($C_{1-4}$)alkyl optionally substituted by at least one halogen;

or a pharmaceutically acceptable salt thereof.

12. The compound according to claim 9 of the formula (Ia₄)

wherein

R₁ is hydrogen, —C(O)R₂, —C(O)NR₃R₄ or —C(O)OR₅ in which

R₂ and R₃ are, independently from each other, hydrogen, cycloalkyl, aryl, heterocyclyl, aralkyl, heteroaralkyl or alkyl optionally substituted with one to four substituents selected from the group consisting of halogen, cycloalkyl, cycloalkoxy, alkoxy, alkyloxyalkoxy, amino, alkylamino, dialkylamino, aryl, aryloxy and heterocyclyl;

R₄ and R₅ are, independently from each other, cycloalkyl, aryl, heterocyclyl, aralkyl, heteroaralkyl or alkyl optionally substituted with one to four substituents selected from the group consisting of halogen, cycloalkyl, cycloalkoxy, alkoxy, alkyloxyalkoxy, amino, alkylamino, dialkylamino, aryl, aryloxy and heterocyclyl;

$R_{2a}$, $R_{3a}$, $R_{4a}$ and $R_{5a}$ are, independently from each other, hydrogen, hydroxy, halogen, cyano, nitro, alkoxy, alkylthio, alkylthiono, sulfonyl, free or esterified carboxy, carbamoyl, sulfamoyl, optionally substituted amino, cycloalkyl, aryl, heterocyclyl, alkenyl, alkynyl or ($C_{1-8}$) alkyl optionally substituted with one to four substituents selected from the group consisting of halogen, hydroxy, cycloalkyl, cycloalkoxy, acyl, acyloxy, alkoxy, alkyloxyalkoxy, amino, alkylamino, dialkylamino, acylamino, carbamoyl, thiol, alkylthio, alkylthiono, sulfonyl, sulfonamido, sulfamoyl, nitro, cyano, free or esterified carboxy, aryl, aryloxy, arylthio, alkenyl, alkynyl, aralkoxy, heteroaralkoxy, heterocyclyl and heterocyclyloxy; or $R_{2a}$ and $R_{3a}$ combined are alkylene which together with the carbon atom to which they are attached form a 3- to 7-membered spirocyclic ring;

or a pharmaceutically acceptable salt thereof.

13. The compound according to claim 12, wherein $R_{4a}$ and $R_{5a}$ are hydrogen;

or a pharmaceutically acceptable salt thereof.

14. The compound according to claim 12, wherein $R_{2a}$ and $R_{3a}$ are, independently from each other, hydrogen, halogen or ($C_{1-4}$)alkyl optionally substituted by at least one halogen;

or a pharmaceutically acceptable salt thereof.

15. The compound according to claim 12, wherein $R_{2a}$ and $R_{3a}$ combined are alkylene which together with the carbon atom to which they are attached form a 3- to 5-membered spirocyclic ring;

or a pharmaceutically acceptable salt thereof.

16. The compound according to claim 12, wherein $R_{2a}$ is —$Y_a$—$(CH_2)_n$—$CR_{6a}R_{7a}$—$(CH_2)_m$—$X_a$ in which $Y_a$ is oxygen or $S(O)_q$ in which q is zero or an integer of 1 or 2; or $Y_a$ is trans CH=CH; or $Y_a$ is absent;

n is an integer from 1 to 6;

$R_{6a}$ and $R_{7a}$ are, independently from each other, hydrogen or lower alkyl; or $R_{6a}$ and $R_{7a}$ combined are alkylene which together with the carbon atom to which they are attached form a 3- to 7-membered ring;

m is zero or an integer of 1 or 2;

$X_a$ is hydroxy, alkoxy, cycloalkyl, cycloalkoxy, acyl, acyloxy, carbamoyl, cyano, trifluoromethyl, free or esterified carboxy, monocyclic aryl or heterocyclyl;

or a pharmaceutically acceptable salt thereof.

17. The compound according to claim 16, wherein $R_{3a}$ is hydrogen;

or a pharmaceutically acceptable salt thereof.

18. The compound according to claim 16, wherein n is an integer of 2 or 3;

$R_{6a}$ and $R_{7a}$ are, independently from each other, hydrogen or lower alkyl;

m is zero or 1;

$X_a$ is hydroxy, carbamoyl, cyano, trifluoromethyl, free or esterified carboxy, monocyclic aryl or heterocyclyl;

or a pharmaceutically acceptable salt thereof.

19. The compound according to claim 16, wherein $Y_a$ is absent;

or a pharmaceutically acceptable salt thereof.

20. The compound according to claim 16, wherein n is 3;

$R_{6a}$ and $R_{7a}$ are lower alkyl;

m is zero or 1;

$X_a$ is hydroxy, cyano or free or esterified carboxy;

or a pharmaceutically acceptable salt thereof.

21. The compound according to claim 20, wherein $R_{6a}$ and $R_{7a}$ are methyl;

or a pharmaceutically acceptable salt thereof.

22. The compound according to claim 1 of the formula

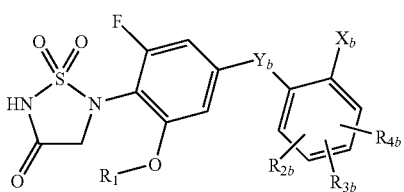

(Ib)

wherein $R_1$ is hydrogen, —C(O)$R_2$, —C(O)NR$_3$R$_4$ or —C(O)OR$_5$ in which $R_2$ and $R_3$ are, independently from each other, hydrogen, cycloalkyl, aryl, heterocyclyl, aralkyl, heteroaralkyl or alkyl optionally substituted with one to four substituents selected from the group consisting of halogen, cycloalkyl, cycloalkoxy, alkoxy, alkyloxyalkoxy, amino, alkylamino, dialkylamino, aryl, aryloxy and heterocyclyl;

$R_4$ and $R_5$ are, independently from each other, cycloalkyl, aryl, heterocyclyl, aralkyl, heteroaralkyl or alkyl optionally substituted with one to four substituents selected from the group consisting of halogen, cycloalkyl, cycloalkoxy, alkoxy, alkyloxyalkoxy, amino, alkylamino, dialkylamino, aryl, aryloxy and heterocyclyl;

$R_{2b}$, $R_{3b}$ and $R_{4b}$ are, independently from each other, hydrogen, hydroxy, halogen, cyano, nitro, alkoxy, alkylthio, alkylthiono, sulfonyl, free or esterified carboxy, carbamoyl, sulfamoyl, optionally substituted amino, cycloalkyl, aryl, heterocyclyl, alkenyl, alkynyl or $(C_{1-8})$ alkyl optionally substituted with one to four substituents selected from the group consisting of halogen, hydroxy, cycloalkyl, cycloalkoxy, acyl, acyloxy, alkoxy, alkyloxyalkoxy, amino, alkylamino, dialkylamino, acylamino, carbamoyl, thiol, alkylthio, alkylthiono, sulfonyl, sulfonamido, sulfamoyl, nitro, cyano, free or esterified carboxy, aryl, aryloxy, arylthio, alkenyl, alkynyl, aralkoxy, heteroaralkoxy, heterocyclyl and heterocyclyloxy; or $R_{2b}$ and $R_{3b}$ combined are alkylene which together with the ring atoms to which they are attached form a 5- to 7-membered fused ring provided $R_2$ and $R_3$ are attached to carbon atoms adjacent to each other; or $R_{2b}$ and $R_{3b}$ combined together with the carbon atom to which they are attached form a fused 5- to 6-membered aromatic or heteroaromatic ring provided $R_2$ and $R_3$ are attached to carbon atoms adjacent to each other;

$X_b$ is hydrogen, fluoro, cyano, or free or esterified carboxy; or $X_b$ is —NR$_{5b}$C(O)R$_{6b}$, —NR$_{5b}$C(O)OR$_{7b}$, —NR$_{5b}$S(O)$_2$R$_{8b}$, —(CH$_2$)$_r$S(O)$_2$R$_{9b}$, —OS(O)$_2$R$_{10b}$ or —O$_s$C(O)NR$_{11b}$R$_{12b}$ in which $R_{5b}$ is hydrogen, lower alkyl, acyl, alkoxycarbonyl or sulfonyl;

$R_{6b}$, $R_{7b}$, $R_{8b}$, $R_{9b}$ and $R_{10b}$ are, independently from each other, cycloalkyl, aryl, heterocyclyl, aralkyl, heteroaralkyl or $(C_{1-8})$alkyl optionally substituted with one to four substituents selected from the group consisting of halogen, hydroxy, cycloalkyl, cycloalkoxy, acyl, acyloxy, alkoxy, alkyloxyalkoxy, amino, alkylamino, dialkylamino, acylamino, carbamoyl, thiol, alkylthio, alkylthiono, sulfonyl, sulfonamido, sulfamoyl, nitro, cyano, free or esterified carboxy, aryl, aryloxy, arylthio, alkenyl, alkynyl, aralkoxy, heteroaralkoxy, heterocyclyl and heterocyclyloxy; or $R_{6b}$, $R_{8b}$ and $R_{9b}$ are, independently from each other, —NR$_{13b}$R$_{14b}$ in which $R_{13b}$ and $R_{14b}$ are, independently from each other, hydrogen, alkyl, cycloalkyl, aralkyl, aryl or heterocyclyl; or $R_{13b}$ and $R_{14b}$ combined are alkylene which together with the nitrogen atom to which they are attached form a 4- to 7-membered ring;

$R_{11b}$ and $R_{12b}$ are, independently from each other, hydrogen, alkyl, cycloalkyl, aralkyl, aryl or heterocyclyl; or $R_{11b}$ and $R_{12b}$ combined are alkylene which together with the nitrogen atom to which they are attached form a 4- to 7-membered ring;

r and s are, independently from each other, zero or an integer of 1; or

C—$X_b$ is replaced by nitrogen;

$Y_b$ is O, S or CH$_2$;

or a pharmaceutically acceptable salt thereof.

23. The compound according to claim 22 of the formula

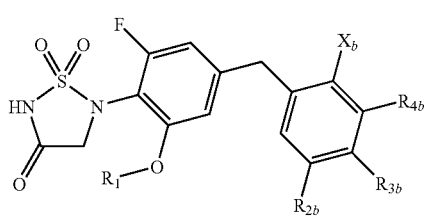

(Ib₁)

wherein
- R₁ is hydrogen, —C(O)R₂, —C(O)NR₃R₄ or —C(O)OR₅ in which
  - R₂ and R₃ are, independently from each other, hydrogen, cycloalkyl, aryl, heterocyclyl, aralkyl, heteroaralkyl or alkyl optionally substituted with one to four substituents selected from the group consisting of halogen, cycloalkyl, cycloalkoxy, alkoxy, alkyloxyalkoxy, amino, alkylamino, dialkylamino, aryl, aryloxy and heterocyclyl;
  - R₄ and R₅ are, independently from each other, cycloalkyl, aryl, heterocyclyl, aralkyl, heteroaralkyl or alkyl optionally substituted with one to four substituents selected from the group consisting of halogen, cycloalkyl, cycloalkoxy, alkoxy, alkyloxyalkoxy, amino, alkylamino, dialkylamino, aryl, aryloxy and heterocyclyl;
- R₂ᵦ, R₃ᵦ and R₄ᵦ are, independently from each other, hydrogen, hydroxy, halogen, cyano, nitro, alkoxy, alkylthio, alkylthiono, sulfonyl, free or esterified carboxy, carbamoyl, sulfamoyl, optionally substituted amino, cycloalkyl, aryl, heterocyclyl, alkenyl, alkynyl or (C₁₋₈) alkyl optionally substituted with one to four substituents selected from the group consisting of halogen, hydroxy, cycloalkyl, cycloalkoxy, acyl, acyloxy, alkoxy, alkyloxyalkoxy, amino, alkylamino, dialkylamino, acylamino, carbamoyl, thiol, alkylthio, alkylthiono, sulfonyl, sulfonamido, sulfamoyl, nitro, cyano, free or esterified carboxy, aryl, aryloxy, arylthio, alkenyl, alkynyl, aralkoxy, heteroaralkoxy, heterocyclyl and heterocyclyloxy; or
- R₂ᵦ and R₃ᵦ combined are alkylene which together with the ring atoms to which they are attached form a 5- to 7-membered fused ring; or
- R₂ᵦ and R₃ᵦ combined together with the carbon atom to which they are attached form a fused 5- to 6-membered aromatic or heteroaromatic ring;
- Xᵦ is cyano; or
- Xᵦ is —NR₅ᵦC(O)R₆ᵦ, —NR₅ᵦC(O)OR₇ᵦ, —NR₅ᵦS(O)₂R₈ᵦ, —(CH₂)ᵣS(O)₂R₉ᵦ or —OS(O)₂R₁₀ᵦ in which R₅ᵦ is hydrogen or lower alkyl;
  - R₆ᵦ, R₇ᵦ, R₈ᵦ, R₁₃ and R₁₀ᵦ are, independently from each other, cycloalkyl, aryl, heterocyclyl, aralkyl, heteroaralkyl or (C₁₋₈)alkyl optionally substituted with one to four substituents selected from the group consisting of halogen, hydroxy, cycloalkyl, cycloalkoxy, acyl, acyloxy, alkoxy, alkyloxyalkoxy, amino, alkylamino, dialkylamino, acylamino, carbamoyl, thiol, alkylthio, alkylthiono, sulfonyl, sulfonamido, sulfamoyl, nitro, cyano, free or esterified carboxy, aryl, aryloxy, arylthio, alkenyl, alkynyl, aralkoxy, heteroaralkoxy, heterocyclyl and heterocyclyloxy; or
  - R₆ᵦ, R₈ᵦ and R₉ᵦ are, independently from each other, —NR₁₃ᵦR₁₄ᵦ in which
    - R₁₃ᵦ and R₁₄ᵦ are, independently from each other, hydrogen, alkyl, cycloalkyl, aralkyl, aryl or heterocyclyl; or
    - R₁₃ᵦ and R₁₄ᵦ combined are alkylene which together with the nitrogen atom to which they are attached form a 4- to 7-membered ring;
  - r is zero; or
- C—Xᵦ is replaced by nitrogen;

or a pharmaceutically acceptable salt thereof.

24. The compound according to claim 1, wherein
- R₁ is hydrogen, —C(O)R₂, —C(O)NR₃R₄ or —C(O)OR₅ in which
  - R₂ and R₃ are, independently from each other, hydrogen, cycloalkyl, aryl, heterocyclyl, aralkyl, heteroaralkyl or alkyl optionally substituted with one to four substituents selected from the group consisting of halogen, cycloalkyl, cycloalkoxy, alkoxy, alkyloxyalkoxy, amino, alkylamino, dialkylamino, aryl, aryloxy and heterocyclyl;
  - R₄ and R₅ are, independently from each other, cycloalkyl, aryl, heterocyclyl, aralkyl, heteroaralkyl or alkyl optionally substituted with one to four substituents selected from the group consisting of halogen, cycloalkyl, cycloalkoxy, alkoxy, alkyloxyalkoxy, amino, alkylamino, dialkylamino, aryl, aryloxy and heterocyclyl;
- U is alkoxy, alkylthio, alkylthiono, sulfonyl, cycloalkyl, aryl, aryloxy, heterocyclyl, alkenyl, alkynyl or (C₁₋₈) alkyl optionally substituted with one to four substituents selected from the group consisting of halogen, hydroxy, cycloalkyl, cycloalkoxy, acyl, acyloxy, alkoxy, alkyloxyalkoxy, optionally substituted amino, carbamoyl, thiol, alkylthio, alkylthiono, sulfonyl, sulfamoyl, nitro, cyano, free or esterified carboxy, aryl, aryloxy, arylthio, alkenyl, alkynyl, aralkoxy, heteroaralkoxy, heterocyclyl and heterocyclyloxy;
- W and V are, independently from each other, hydrogen, halogen, (C₁₋₃)alkyl or (C₁₋₃)alkoxy;

or a pharmaceutically acceptable salt thereof.

25. The compound according to claim 24, wherein
- U is —Y_c—(CH₂)_p—CR₂_cR₃_c—(CH₂)_t—X_c in which
  - Y_c is oxygen or S(O)_v in which v is zero or an integer of 1 or 2; or
  - Y_c is C≡C; or
  - Y_c is absent;
  - p and t are, independently from each other, zero or an integer from 1 to 8;
  - R₂_c and R₃_c are, independently from each other, hydrogen or lower alkyl; or
  - R₂_c and R₃_c combined are alkylene which together with the carbon atom to which they are attached form a 3- to 7-membered ring;
  - X_c is hydroxy, alkoxy, cycloalkyl, cycloalkoxy, acyl, acyloxy, carbamoyl, optionally substituted amino, cyano, trifluoromethyl, free or esterified carboxy, heterocyclyl, monocyclic aryl or monocyclic aryloxy;

or a pharmaceutically acceptable salt thereof.

26. The compound according to claim 24, wherein
i) U is monocyclic aryl or 5- to 6-membered heterocyclic ring, or
ii) X_c is monocyclic aryl or 5- to 6-membered heterocyclic ring, or a pharmaceutically acceptable salt thereof.

27. The compound according to claim 26 of the formula

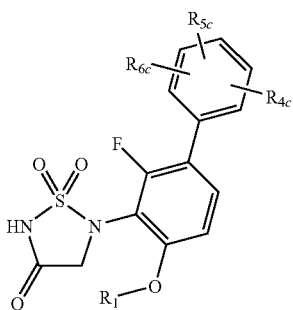

(Ic)

wherein
R₁ is hydrogen, —C(O)R₂, —C(O)NR₃R₄ or —C(O)OR₅ in which
R₂ and R₃ are, independently from each other, hydrogen, cycloalkyl, aryl, heterocyclyl, aralkyl, heteroaralkyl or alkyl optionally substituted with one to four substituents selected from the group consisting of halogen, cycloalkyl, cycloalkoxy, alkoxy, alkyloxyalkoxy, amino, alkylamino, dialkylamino, aryl, aryloxy and heterocyclyl;
R₄ and R₅ are, independently from each other, cycloalkyl, aryl, heterocyclyl, aralkyl, heteroaralkyl or alkyl optionally substituted with one to four substituents selected from the group consisting of halogen, cycloalkyl, cycloalkoxy, alkoxy, alkyloxyalkoxy, amino, alkylamino, dialkylamino, aryl, aryloxy and heterocyclyl;
R₄c, R₅c and R₆c are, independently from each other, hydrogen, hydroxy, halogen, cyano, nitro, alkoxy, alkylthio, alkylthiono, sulfonyl, free or esterified carboxy, carbamoyl, sulfamoyl, optionally substituted amino, cycloalkyl, aryl, heterocyclyl, alkenyl, alkynyl or (C₁₋₈) alkyl optionally substituted with one to four substituents selected from the group consisting of halogen, hydroxy, cycloalkyl, cycloalkoxy, acyl, acyloxy, alkoxy, alkyloxyalkoxy, optionally substituted amino, carbamoyl, thiol, alkylthio, alkylthiono, sulfonyl, sulfamoyl, nitro, cyano, free or esterified carboxy, aryl, aryloxy, arylthio, alkenyl, alkynyl, aralkoxy, heteroaralkoxy, heterocyclyl and heterocyclyloxy; or
C—R₄c, C—R₅c and C—R₆c are, independently from each other, replaced by nitrogen;
or a pharmaceutically acceptable salt thereof.

28. The compound according to claim 1 selected from the group consisting of:
Methanesulfonic acid 2-[3-fluoro-5-hydroxy-4-(1,1,4-trioxo-1,2,5-thiadiazolidin-2-yl)-benzyl]-4-methylphenyl ester;
Methanesulfonic acid 2-[3-fluoro-5-hydroxy-4-(1,1,4-trioxo-1,2,5-thiadiazolidin-2-yl)-benzyl]-5-methylphenyl ester;
Methanesulfonic acid 2-[3-fluoro-5-hydroxy-4-(1,1,4-trioxo-1,2,5-thiadiazolidin-2-yl)-benzyl]-6-methylphenyl ester;
Methanesulfonic acid 2-[3-fluoro-5-hydroxy-4-(1,1,4-trioxo-1,2,5-thiadiazolidin-2-yl)-benzyl]-phenyl ester;
N-{2-[3-Fluoro-5-hydroxy-4-(1,1,4-trioxo-1,2,5-thiadiazolidin-2-yl)-benzyl]-5-methylphenyl}-methanesulfonamide;
N-{2-[3-Fluoro-5-hydroxy-4-(1,1,4-trioxo-1,2,5-thiadiazolidin-2-yl)-benzyl]-4-methylphenyl}-methanesulfonamide;
N-{2-[3-Fluoro-5-hydroxy-4-(1,1,4-trioxo-1,2,5-thiadiazolidin-2-yl)-benzyl]-phenyl}-methanesulfonamide;
5-(4-Benzyl-2-fluoro-6-hydroxy-phenyl)-1,1-dioxo-1,2,5-thiadiazolidin-3-one;
5-(2-Fluoro-6-hydroxy-4-methylphenyl)-1,1-dioxo-1,2,5-thiadiazolidin-3-one;
Benzoic acid 5-benzyl-3-fluoro-2-(1,1,4-trioxo-1,2,5-thiadiazolidin-2-yl)-phenyl ester;
Benzoic acid 3-fluoro-5-methyl-2-(1,1,4-trioxo-1,2,5-thiadiazolidin-2-yl)-phenyl ester;
5-(4-Cyclobutylmethyl-2-fluoro-6-hydroxyphenyl)-1,1-dioxo-1,2,5-thiadiazolidin-3-one potassium salt;
5-(4-Cyclohexylmethyl-2-fluoro-6-hydroxyphenyl)-1,1-dioxo-1,2,5-thiadiazolidin-3-one;
7-[2-Fluoro-4-hydroxy-3-(1,1,4-trioxo-1,2,5-thiadiazolidin-2-yl)-phenyl]-2,2-dimethylheptanenitrile;
5-(2,4-Difluoro-6-hydroxyphenyl)-1,1-dioxo-1,2,5-thiadiazolidin-3-one;
5-(1-Fluoro-3-hydroxy-7-methylnaphthalen-2-yl)-1,1-dioxo-1,2,5-thiadiazolidin-3-one;
5-(1-Fluoro-3-hydroxynaphthalen-2-yl)-1,1-dioxo-1,2,5-thiadiazolidin-3-one;
5-(7-Ethyl-1-fluoro-3-hydroxy-5,6,7,8-tetrahydronaphthalen-2-yl)-1,1-dioxo-1,2,5-thiadiazolidin-3-one;
5-[1-Fluoro-3-hydroxy-7-(5-hydroxy-4,4-dimethylpentyl)-naphthalen-2-yl]-1,1-dioxo-1,2,5-thiadiazolidin-3-one;
5-[8-Fluoro-6-hydroxy-7-(1,1,4-trioxo-1,2,5-thiadiazolidin-2-yl)-naphthalen-2-yl]-2,2-dimethyl-pentanoic acid;
Benzoic acid 4-fluoro-6-methyl-3-(1,1,4-trioxo-1,2,5-thiadiazolidin-2-yl)-naphthalen-2-yl ester;
Benzoic acid 6-ethyl-4-fluoro-3-(1,1,4-trioxo-1,2,5-thiadiazolidin-2-yl)-5,6,7,8-tetrahydronaphthalen-2-yl ester;
Benzoic acid 4-fluoro-3-(1,1,4-trioxo-1,2,5-thiadiazolidin-2-yl)-naphthalen-2-yl ester;
Benzoic acid 4-fluoro-6-(5-hydroxy-4,4-dimethylpentyl)-3-(1,1,4-trioxo-1,2,5-thiadiazolidin-2-yl)-naphthalen-2-yl ester;
Benzoic acid 3-fluoro-5-(2-methanesulfonyloxy-5-methylbenzyl)-2-(1,1,4-trioxo-1,2,5-thiadiazolidin-2-yl)-phenyl ester;
Benzoic acid 3-fluoro-5-(2-methanesulfonyloxy-4-methylbenzyl)-2-(1,1,4-trioxo-1,2,5-thiadiazolidin-2-yl)-phenyl ester;
Benzoic acid 4-(6-cyano-6,6-dimethylhexyl)-3-fluoro-2-(1,1,4-trioxo-1,2,5-thiadiazolidin-2-yl)-phenyl ester;
Benzoic acid 3-fluoro-5-(2-methanesulfonylamino-5-methylbenzyl)-2-(1,1,4-trioxo-1,2,5-thiadiazolidin-2-yl)-phenyl ester;
Benzoic acid 3-fluoro-5-(2-methanesulfonylamino-4-methylbenzyl)-2-(1,1,4-trioxo-1,2,5-thiadiazolidin-2-yl)-phenyl ester;
Benzoic acid 3-fluoro-5-(2-methanesulfonyloxy-3-methylbenzyl)-2-(1,1,4-trioxo-1,2,5-thiadiazolidin-2-yl)-phenyl ester;
5-(4-Ethyl-2-fluoro-6-hydroxyphenyl)-1,1-dioxo-1-[1,2,5]thiadiazolidin-3-one;
5-(4-Cyclopentylmethyl-2-fluoro-6-hydroxyphenyl)-1,1-dioxo-1-[1,2,5]thiadiazolidin-3-one;
5-(2,3-Difluoro-6-hydroxy-4-methylphenyl)-1,1-dioxo-1,2,5]thiadiazolidin-3-one;

5-(2,3-Difluoro-6-hydroxyphenyl)-1,1-dioxo-1,2,5]thiadiazolidin-3-one;

1,1-Dioxo-5-(2,3,5-trifluoro-6-hydroxy-phenyl)-1,2,5]thiadiazolidin-3-one potassium salt;

1,1-Dioxo-5-(2,3,5-trifluoro-6-hydroxy-phenyl)-1,2,5]thiadiazolidin-3-one;

5-(2-Fluoro-6-hydroxyphenyl)-1,1-dioxo-[1,2,5]thiadiazolidin-3-one potassium salt;

5-(2-Fluoro-6-hydroxyphenyl)-1,1-dioxo-[1,2,5]thiadiazolidin-3-one;

2-(4-{3-[3-Fluoro-5-hydroxy-4-(1,1,4-trioxo-1-[1,2,5]thiadiazolidin-2-yl)-phenyl]-propionylamino}-butoxy)-6-hydroxy-benzoic acid methyl ester potassium salt;

2-(4-{3-[3-Fluoro-5-hydroxy-4-(1,1,4-trioxo-1-[1,2,5]thiadiazolidin-2-yl)-phenyl]-propionylamino}-butoxy)-6-hydroxy-benzoic acid methyl ester;

7-[2-Fluoro-4-hydroxy-3-(1,1,4-trioxo-1-[1,2,5]thiadiazolidin-2-yl)-phenyl]-2,2-dimethylheptanoic acid dipotassium salt;

7-[2-Fluoro-4-hydroxy-3-(1,1,4-trioxo-1-[1,2,5]thiadiazolidin-2-yl)-phenyl]-2,2-dimethylheptanoic acid;

5-(7-Bromo-1-fluoro-3,6-dihydroxynaphthalen-2-yl)-1,1-dioxo-[1,2,5]thiadiazolidin-3-one;

5-[8-Fluoro-6-hydroxy-7-(1,1,4-trioxo-1-[1,2,5]thiadiazolidin-2-yl)-naphthalen-2-yl]-2,2-dimethylpentanoic acid isopropyl ester potassium salt;

5-[8-Fluoro-6-hydroxy-7-(1,1,4-trioxo-1-[1,2,5]thiadiazolidin-2-yl)-naphthalen-2-yl]-2,2-dimethylpentanoic acid isopropyl ester;

5-[8-Fluoro-6-hydroxy-7-(1,1,4-trioxo-[1,2,5]thiadiazolidin-2-yl)-naphthalen-2-yl]-2,2-dimethyl-pentanoic acid methyl ester;

5-[8-Fluoro-6-hydroxy-7-(1,1,4-trioxo-[1,2,5]thiadiazolidin-2-yl)-naphthalen-2-yl]-2,2-dimethyl-pentanoic acid ethyl ester;

5-[8-Fluoro-6-hydroxy-7-(1,1,4-trioxo-[1,2,5]thiadiazolidin-2-yl)-naphthalen-2-yl]-2,2-dimethyl-pentanoic acid butyl ester;

(S)-5-[8-Fluoro-6-hydroxy-7-(1,1,4-trioxo-[1,2,5]thiadiazolidin-2-yl)-naphthalen-2-yl]-2-methyl-pentanoic acid;

(R)-5-[8-Fluoro-6-hydroxy-7-(1,1,4-trioxo-[1,2,5]thiadiazolidin-2-yl)-naphthalen-2-yl]-2-methyl-pentanoic acid;

5-[1-Fluoro-3-hydroxy-7-(4-hydroxy-4-methyl-pentyl)-naphthalen-2-yl]-1,1-dioxo-[1,2,5]thiadiazolidin-3-one;

5-[8-Fluoro-6-hydroxy-7-(1,1,4-trioxo-[1,2,5]thiadiazolidin-2-yl)-naphthalen-2-yl]-pentanoic acid;

4-[8-Fluoro-6-hydroxy-7-(1,1,4-trioxo-[1,2,5]thiadiazolidin-2-yl)-naphthalen-2-yl]-butyric acid;

5-[8-Fluoro-6-hydroxy-7-(1,1,4-trioxo-[1,2,5]thiadiazolidin-2-yl)-naphthalen-2-yl]-pentanoic acid ethyl ester;

3-{3-[8-Fluoro-6-hydroxy-7-(1,1,4-trioxo-[1,2,5]thiadiazolidin-2-yl)-naphthalen-2-yl]-phenyl}-propionic acid ethyl ester;

3-{3-[8-Fluoro-6-hydroxy-7-(1,1,4-trioxo-[1,2,5]thiadiazolidin-2-yl)-naphthalen-2-yl]-phenyl}-propionic acid;

3-[8-Fluoro-6-hydroxy-7-(1,1,4-trioxo-[1,2,5]thiadiazolidin-2-yl)-naphthalen-2-yl]-benzonitrile;

3-[8-Fluoro-6-hydroxy-7-(1,1,4-trioxo-[1,2,5]thiadiazolidin-2-yl)-naphthalen-2-yl]-benzoic acid; and 5-[1-Fluoro-3-hydroxy-7-(4-formyl-4-methyl-pentyl)-naphthalen-2-yl]-1,1-dioxo-[1,2,5]thiadiazolidin-3-one;

or a pharmaceutically acceptable salt thereof.

29. A method for the treatment of diabietes, comprising:
administering to a mammal in need thereof a therapeutically effective amount of the compound of claim 1.

30. A pharmaceutical composition, comprising:
a therapeutically effective amount of a compound according to claim 1 in combination with one or more pharmaceutically acceptable carriers.

* * * * *